US012207950B2

(12) United States Patent
Catani et al.

(10) Patent No.: US 12,207,950 B2
(45) Date of Patent: Jan. 28, 2025

(54) PREDICTIVE MONITORING OF THE GLUCOSE-INSULIN ENDOCRINE METABOLIC REGULATORY SYSTEM

(71) Applicant: UnitedHealth Group Incorporated, Minnetonka, MN (US)

(72) Inventors: Steven Catani, Athens, GA (US); Yinglong Guo, Roseville, MN (US); Benjamin W. Ehlert, Wayzata, MN (US); Cody James Lensing, Maple Grove, MN (US); Stephen Rushton Garth, Maplewood, MN (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 698 days.

(21) Appl. No.: 16/985,745

(22) Filed: Aug. 5, 2020

(65) Prior Publication Data
US 2022/0039757 A1    Feb. 10, 2022

(51) Int. Cl.
*A61B 5/00*    (2006.01)
*A61B 5/145*   (2006.01)
*G06N 3/047*   (2023.01)
*G06N 3/048*   (2023.01)
*G06N 20/00*   (2019.01)
*G16H 50/20*   (2018.01)

(52) U.S. Cl.
CPC ........ *A61B 5/7275* (2013.01); *A61B 5/14532* (2013.01); *A61B 5/746* (2013.01); *G06N 3/047* (2023.01); *G06N 3/048* (2023.01); *G06N 20/00* (2019.01); *G16H 50/20* (2018.01)

(58) Field of Classification Search
CPC ... A61B 5/7275; A61B 5/14532; A61B 5/746; A61B 5/1112; A61B 5/4839; A61B 5/7221; A61B 5/7267; A61B 5/0022; G06N 3/047; G06N 3/048; G06N 20/00; G06N 3/044; G06N 3/045; G06N 3/08; G16H 50/20
See application file for complete search history.

(56) References Cited

U.S. PATENT DOCUMENTS

| 2011/0098548 A1 | 4/2011  | Budiman et al.   |
| 2013/0211220 A1 | 8/2013  | Cobelli et al.   |
| 2019/0252079 A1 | 8/2019  | Constantin et al.|
| 2020/0245913 A1 | 8/2020  | Dalal et al.     |
| 2022/0346676 A1 | 11/2022 | Pecchia et al.   |
| 2023/0080876 A1 | 3/2023  | Miyamoto         |

FOREIGN PATENT DOCUMENTS

| EP | 3395252 A1 | 10/2018 |
| GB | 2586788 A  | 3/2021  |

OTHER PUBLICATIONS

Kölle, K., Biester, T., Christiansen, S., Fougner, A. L., & Stavdahl, Ø. (2019). Pattern recognition reveals characteristic postprandial glucose changes: Non-individualized meal detection in diabetes mellitus type 1. IEEE journal of biomedical and health informatics, 24(2), 594-602. (Year: 2019).*
Cappon, G.; Facchinetti, A.; Sparacino, G.; Georgiou, P.; Herrero, P. Classification of Postprandial Glycemic Status with Application to Insulin Dosing in Type 1 Diabetes—An In Silico Proof-of-Concept. Sensors 2019, 19, 3168. https://doi.org/10.3390/s19143168 (Year: 2019).*
Ajmera, I. et al. "The Impact Of Mathematical Modeling On The Understanding of Diabetes and Related Complications," CPT: Pharmacometrics & Systems Pharmacology, vol. 2, No. 7, Jul. 10, 2013, pp. 1-14. DOI: 10.1038/psp.2013.30.
Bergman, R.N. et al. "The Evolution of B-Cell Dysfunction and Insulin Resistance In Type 2 Diabetes," European Journal of Clinical Investigation, vol. 32, Suppl. 3, (2002), pp. 35-45.
Cappon, Giacomo et al. "A Neural-Network-Based Approach to Personalize Insulin Bolus Calculation Using Continuous Glucose Monitoring," Journal of Diabetes Science and Technology, (2018), vol. 12, Issue 2, pp. 265-272. DOI: 10.1177/1932296818759558.
De Gaetano, Andrea et al. "Routine OGTT: A Robust Model Including Incretin Effect For Precise Identification of Insulin Sensitivity and Secretion In A Single Individual," PLoS One, vol. 8, No. 8. e70875. DOI: 10.1371/journal.pone.0070875.
Ferrannini, Ele et al. "How To Measure Insulin Sensitivity," Journal of Hypertension, vol. 16, No. 7, (1998), pp. 895-906.
Hethcote, Herbert W. "The Mathematics Of Infectious Diseases," SIAM review, vol. 42, No. 4, Dec. 2000, pp. 599-653. [Retrieved from the Internet Aug. 20, 2020] URL: http://www.maths.usyd.edu.au/u/marym/populations/hethcote.pdf.
Lanzas, Cristina et al. "Complex System Modelling For Veterinary Epidemiology," Preventive Veterinary Medicine, vol. 118, Issues 2-3, Feb. 1, 2015, pp. 207-214. DOI: 10.1016/j.prevetmed.2014.09.012.
Li, Jiaxu et al. "Analysis Of IVGTT Glucose-Insulin Interaction Models With Time Delay," Discrete and Continuous Dynamical Systems—Series B, vol. 1, No. 1, Feb. 2001, pp. 103-124.
Li, Jiaxu et al. "Modeling The Glucose-Insulin Regulatory System and Ultradian Insulin Secretory Oscillations With Two Explicit Time Delays," Journal of Theoretical Biology, vol. 242, (2006), pp. 722-735.
Li, Jiaxu et al. "The Range Of Time Delay and The Global Stability Of The Equilibrium For An IVGTT Model," Mathematical Biosciences, vol. 235, (2012), pp. 128-137.
Li, Steven Cheng-Xian et al. "A Scalable End-To-End Gaussian Process Adapter For Irregularly Sampled Time Series Classification," In Advances In Neural Information Processing Systems (NIPS), (2016), pp. 1804-1812.

(Continued)

*Primary Examiner* — Kaitlyn L Minchella
*Assistant Examiner* — Nidhi Dharithreesan
(74) *Attorney, Agent, or Firm* — Alston & Bird LLP

(57) ABSTRACT

There is a need for more effective and efficient predictive data analysis, such as more effective and efficient data analysis solutions for performing predictive monitoring of the glucose-insulin endocrine metabolic regulatory system. Certain embodiments utilize systems, methods, and computer program products that perform predictive data analysis by utilizing at least one of glucose surge excursion detections, steady-state glucose-insulin machine learning models, and parameter space refinement machine learning models.

15 Claims, 16 Drawing Sheets

(56) References Cited

OTHER PUBLICATIONS

McCallum, Hamish et al. "How Should Pathogen Transmission Be Modelled?," Trends In Ecology & Evolution, vol. 16, No. 6, Jun. 2001, pp. 295-300.

Pacini, Giovanni et al. "MINMOD: A Computer Program To Calculate Insulin Sensitivity and Pancreatic Responsivity From The Frequently Sampled Intravenous Glucose Tolerance Test," Computer Methods and Programs In Biomedicine, vol. 23, (1986), pp. 113-122.

Steil, Garry M. et al. "Determination of Plasma Glucose During Rapid Glucose Excursions With A Subcutaneous Glucose Sensor," Diabetes Technology & Therapeutics, vol. 5, No. 1, Jan. 2003, pp. 27-31.

Sun, Qingnan et al. "Reinforcement Learning-Based Adaptive Insulin Advisor For Individuals With Type 1 Diabetes Patients Under Multiple Daily Injections Therapy," In 2019 41st Annual International Conference of the IEEE Engineering In Medicine and Biology Society (EMBC), Jul. 23-27, 2019, pp. 3609-3612, IEEE.

González-Rodríguez, Maria et al. "Postprandial Glycemic Response In A Non-Diabetic Adult Population: The Effect Of Nutrients Is Different Between Men and Women," Nutrition & Metabolism, vol. 16, No. 46, Jul. 17, 2019, pp. 1-9, DOI: 10.1186/s12986-019-0368-1.

NonFinal Office Action for U.S. Appl. No. 16/985,755, dated May 26, 2023, (19 pages), United States Patent and Trademark Office, US.

Brenner, Michael et al. "Estimation of Insulin Secretion, Glucose Uptake By Tissues, and Liver Handling Of Glucose Using A Mathematical Model Of Glucose-Insulin Homeostasis In Lean and Obese Mice," Heliyon, vol. 3, Issue 6, Jun. 2017, e00310, DOI: 10.1016/j.heliyon.2017.e00310.

Cobelli, Claudio et al. "Diabetes: Models, Signals, and Control," IEEE Reviews In Biomedical Engineering, vol. 2, pp. 54-96, Dec. 22, 2009 (ePub: Jan. 1, 2009), DOI: 10.1109/RBME.2009.2036073.

Huard, Benoit et al. "Investigation of Stability In A Two-Delay Model Of The Ultradian Oscillations In Glucose-Insulin Regulation," Communications In Nonlinear Science and Numerical Simulation, vol. 26, Issues 1-3, Sep. 2015, pp. 211-222, DOI: 10.1016/j.cnsns.2015.02.017.

NonFinal Office Action for U.S. Appl. No. 16/985,765, dated May 2, 2023, (16 pages), United States Patent and Trademark Office, US.

Percival, Matthew W. et al. "Modeling The Effects Of Subcutaneous Insulin Administration and Carbohydrate Consumption On Blood Glucose," Journal of Diabetes Science and Technology, vol. 4, Issue 5, Sep. 2010, pp. 1214-1228.

Singal, Pooja et al. "Simple Modeling Allows Prediction Of Steady-State Glucose Disposal Rate From Early Data In Hyperinsulinemic Glucose Clamps," American Journal of Physiology-Endocrinology and Metabolism, vol. 298, No. 2, pp. E229-E236, (Year: 2010), (First Published: Nov. 17, 2009), DOI: 10-1152/ajpendo.00603. 2009.

Woldaregay, Ashenafi Zebene et al. "Data-Driven Modeling and Prediction of Blood Glucose Dynamics: Machine Learning Applications In Type 1 Diabetes," Artificial Intelligence In Medicine, vol. 98, Jul. 19, 2019, pp. 109-134, DOI: 10.1016/j.artmed.2019.07.007.

Final Office Action for U.S. Appl. No. 16/985,759, dated Nov. 16, 2023, (16 pages), United States Patent and Trademark Office, US.

Hall H, Perelman D, Breschi A, et al. Glucotypes reveal new patterns of glucose dysregulation. PLoS Biol. 2018;16(7):e2005143. Published Jul. 24, 2018. doi:10.1371/journal.pbio.2005143 (Year: 2018).

Michele Schiavon, Chiara Dalia Man, Yogish C. Kudva, Ananda Basu, Claudio Cobelli; Quantitative Estimation of Insulin Sensitivity in Type 1 Diabetic SubjectsWearing a Sensor-Augmented Insulin Pump. Diabetes Care May 1, 2014; 37 (5): 1216-1223. https://doi.org/10.2337/dc13-1120 (Year: 2014).

Non-Final Rejection Mailed on Mar. 27, 2024 for U.S. Appl. No. 16/985,755, 23 page(s).

Advisory Action for U.S. Appl. No. 16/985,765, dated Nov. 3, 2023, (3 pages), United States Patent and Trademark Office, US.

Farmer, Jr. Terry G. et al. "Effectiveness Of Intravenous Infusion Algorithms For Glucose Control In Diabetic Patients Using Different Simulation Models," Industrial & Engineering Chemistry Research, vol. 48, No. 9, pp. 4402-4414, Mar. 24, 2009, (Year: 2009), DOI: 10.1021/ie800871t.

Final Office Action for U.S. Appl. No. 16/985,765, dated Aug. 18, 2023, (21 pages), United States Patent and Trademark Office, US.

Hall, Heather et al. " Glucotypes Reveal New Patterns Of Glucose Dysregulation," PLoS Biology, vol. 16, No. 7: e2005143, pp. 1-23, Jul. 24, 2018, (Year: 2018), DOI: 10.1371/journaal.pbio.2005143.

NonFinal Office Action for U.S. Appl. No. 16/985,759, dated Aug. 10, 2023, (12 pages), United States Patent and Trademark Office, US.

Notice of Allowance and Fees Due (PTOL-85) Mailed on Sep. 12, 2024 for U.S. Appl. No. 16/985,765, 2 page (s).

\* cited by examiner

PREDICTIVE MONITORING OF THE GLUCOSE-INSULIN ENDOCRINE METABOLIC REGULATORY SYSTEM

BACKGROUND

Various embodiments of the present invention address technical challenges related to performing predictive data analysis, such as performing predictive data analysis to facilitate intelligent monitoring of the glucose-insulin endocrine metabolic regulatory system. Various embodiments of the present invention disclose innovative techniques for performing glucose-insulin predictive data analysis.

BRIEF SUMMARY

In general, embodiments of the present invention provide methods, apparatus, systems, computing devices, computing entities, and/or the like for predictive data analysis. Certain embodiments utilize systems, methods, and computer program products that perform predictive data analysis by utilizing at least one of glucose surge excursion detections, steady-state glucose-insulin machine learning models, and parameter space refinement machine learning models.

In accordance with one aspect, a method is provided. In one embodiment, the method comprises: for each temporal unit of a plurality of temporal units, determining an excursion initiation probability based at least in part on at least one of: (i) whether a neighboring CGM moving average for the temporal unit exceeds a neighboring CGM moving average threshold; (ii) whether a CGM first derivative approximation for the temporal unit exceeds a CGM first derivative approximation threshold; or (iii) whether a CGM z-score for the temporal unit exceeds a CGM z-score threshold; determining an excursion start time from the plurality of temporal units based at least in part on each excursion initiation probability for a temporal unit of the plurality of temporal units; for each temporal unit in a selected subset of the plurality of temporal units that occur after a predefined time interval following the excursion start time, determining an excursion termination probability for the temporal unit based at least in part on at least one of: (i) whether the neighboring CGM moving average for the temporal unit fails to exceed the neighboring CGM moving average threshold; (ii) whether the CGM first derivative approximation for the temporal unit fails to exceed the CGM first derivative approximation threshold; or (iii) whether the CGM z-score for the temporal unit fails to exceed the CGM z-score threshold; determining an excursion end time based at least in part on each excursion initiation probability for a temporal unit in the selected subset; determining the glucose surge excursion based at least in part on the excursion start time and the excursion end time; generating one or more glucose-insulin predictions based at least in part on the glucose surge prediction; and performing one or more prediction-based actions based at least in part on the glucose-insulin prediction.

In accordance with one aspect, a method is provided. In one embodiment, the method comprises: determining, based at least in part on the glucose monitoring data, a steady-state glucose concentration measurement associated with the glucose surge excursion, wherein (i) the steady-state glucose concentration measurement is associated with a steady-state time interval within the glucose surge excursion; and (ii) the steady-state time interval is estimated to be associated with absence of temporal glucose changes and with absence of exogenous glucose infusion; processing the steady-state glucose concentration measurement in accordance with a steady-state glucose-insulin prediction machine learning model to generate one or more target parameter values of the steady-state glucose-insulin prediction machine learning model, wherein the steady-state glucose-insulin prediction machine learning model is generated by removing glucose-insulin temporal derivative factors and an exogenous glucose infusion rate factor from a glucose-biased glucose-insulin prediction machine learning model; generating an insulin sensitivity prediction based at least in part on the one or more estimated target parameter values; and performing one or more prediction-based actions based at least in part on the insulin sensitivity prediction.

In accordance with one aspect, a method is provided. In one embodiment, the method comprises: determining, based at least in part on the glucose monitoring data, a steady-state glucose concentration measurement associated with the glucose surge excursion, wherein (i) the steady-state glucose concentration measurement is associated with a steady-state time interval within the glucose surge excursion; and (ii) the steady-state time interval is estimated to be associated with absence of temporal glucose changes and with absence of exogenous glucose infusion; processing the steady-state glucose concentration measurement in accordance with a steady-state glucose-insulin prediction machine learning model to generate one or more target parameter values of the steady-state glucose-insulin prediction machine learning model, wherein the steady-state glucose-insulin prediction machine learning model is generated by removing glucose-insulin temporal derivative factors and an exogenous glucose infusion rate factor from a glucose-biased glucose-insulin prediction machine learning model; generating a beta cell capacity prediction based at least in part on the one or more estimated target parameter values; and performing one or more prediction-based actions based at least in part on the beta cell capacity prediction.

In accordance with one aspect, a method is provided. In one embodiment, the method comprises: identifying a model utility data object associated with a non-optimized machine learning model, wherein (i) the model utility data object maps each parameter value combination of one or more parameter value combinations associated with the non-optimized machine learning model to a utility measurement of one or more utility measurements; and (ii) each parameter value combination of the one or more parameter value combinations comprises a parameter value for each optimizable parameter of one or more optimizable parameters associated with the non-optimized machine learning model; processing the model utility data object in accordance with a parameter space refinement machine learning model to generate an optimum parameter space for the non-optimized machine learning model, wherein the optimum parameter space comprises a respective range for each optimizable parameter of the one or more optimizable parameters; determining an estimated optimum utility measurement for the non-optimized machine learning model based at least in part on each intra-region optimum utility measurement of an intra-region utility measurement subset of the one or more utility measurements that are each associated with a parameter value combination of the one or more parameter value combinations that falls within the optimum parameter space; updating the non-optimized learning model in accordance with a parameter value combination of the one or more parameter value combinations that is associated with the estimated global optimum utility measurement to generate an optimized machine learning model; and providing access to the optimized machine learning model for performing predictive data analysis tasks to generate predictive data analysis outputs and for performing prediction-based actions based at least in part on the predictive data analysis outputs.

BRIEF DESCRIPTION OF THE DRAWINGS

Figure 1:
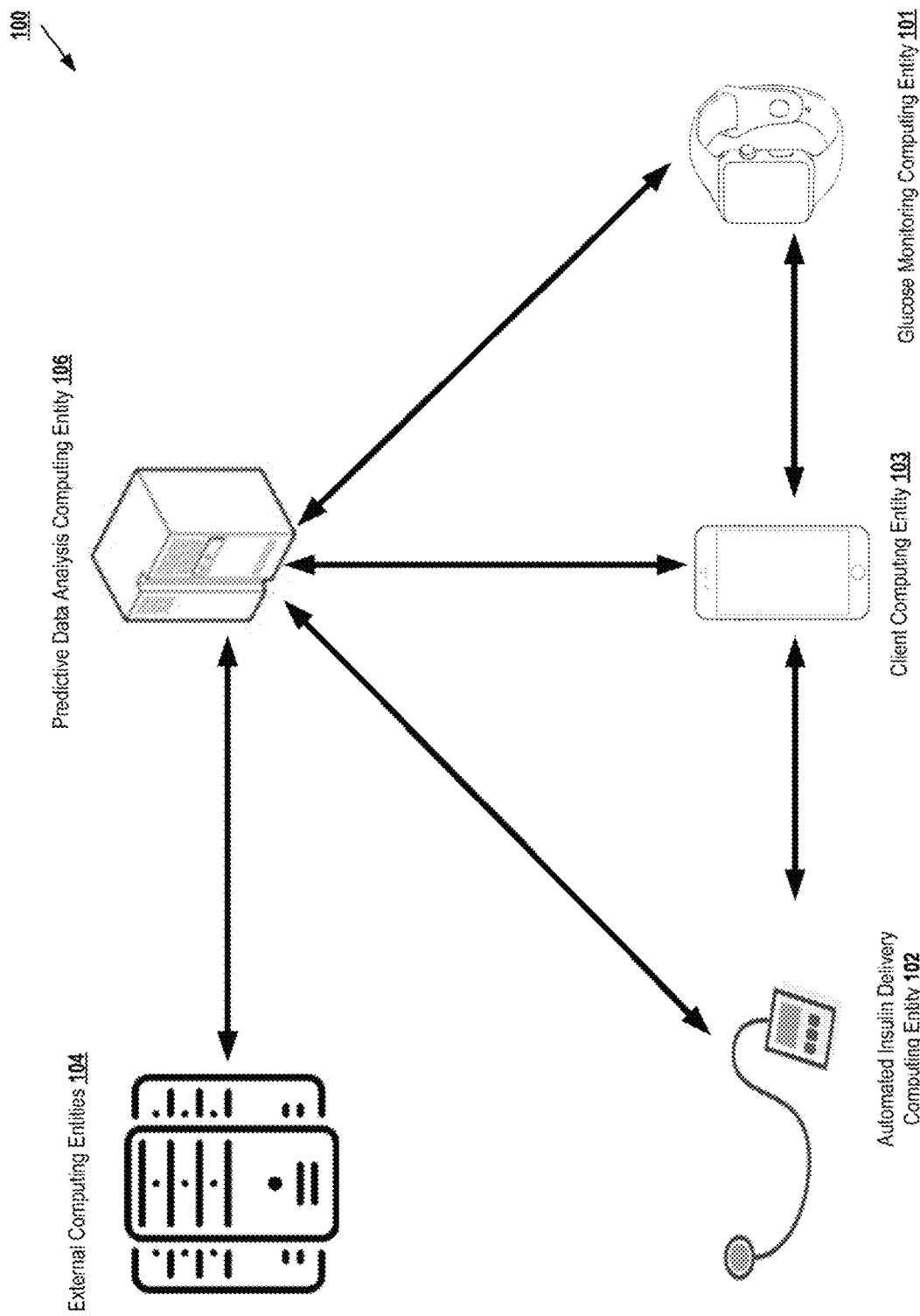

Having thus described the invention in general terms, reference will now be made to the accompanying drawings, which are not necessarily drawn to scale, and wherein:

FIG. 1 provides an exemplary overview of a hardware architecture that can be used to practice embodiments of the present invention.

Figure 2:
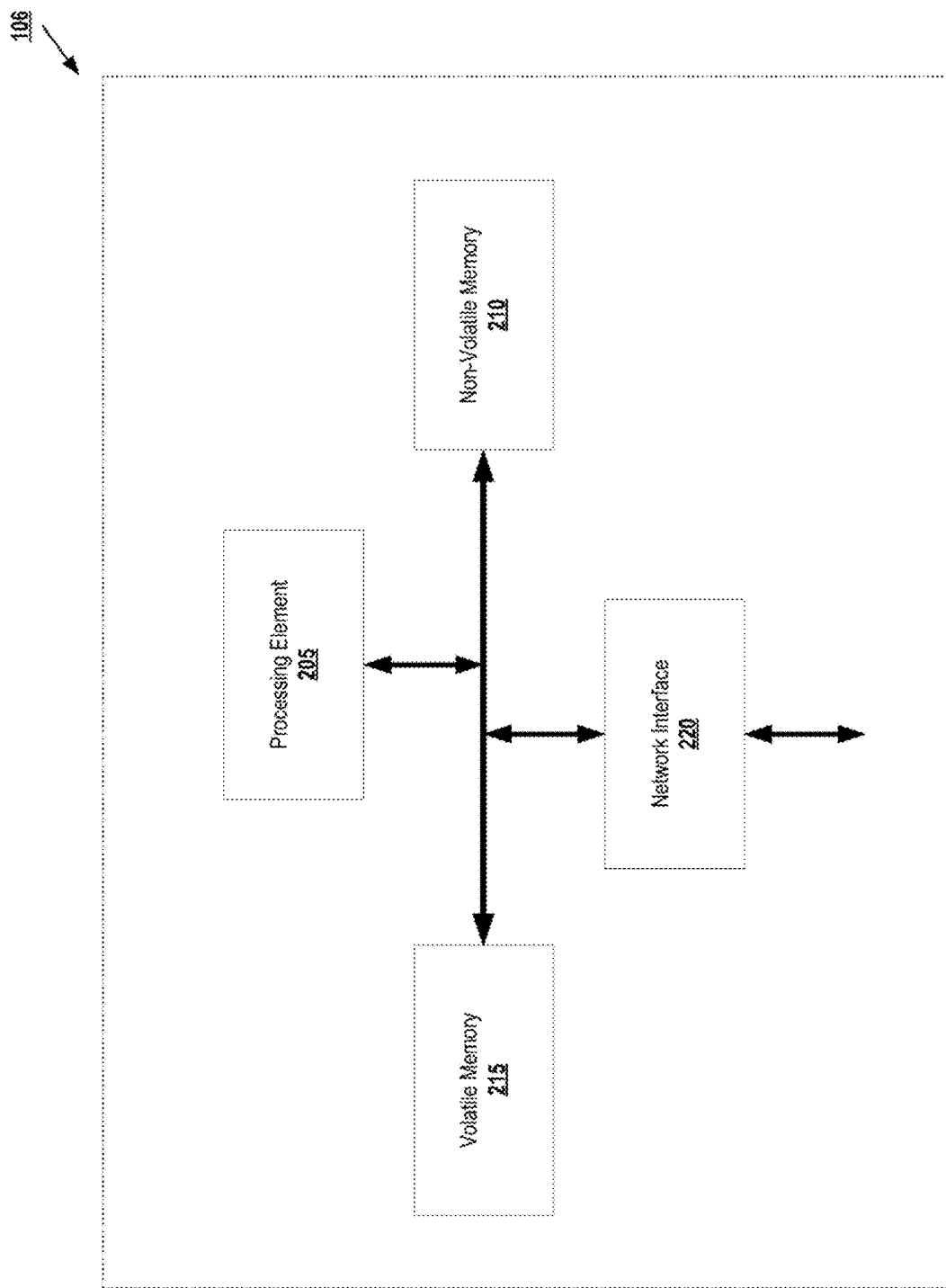

FIG. 2 provides an example predictive data analysis computing entity, in accordance with some embodiments discussed herein.

Figure 3:
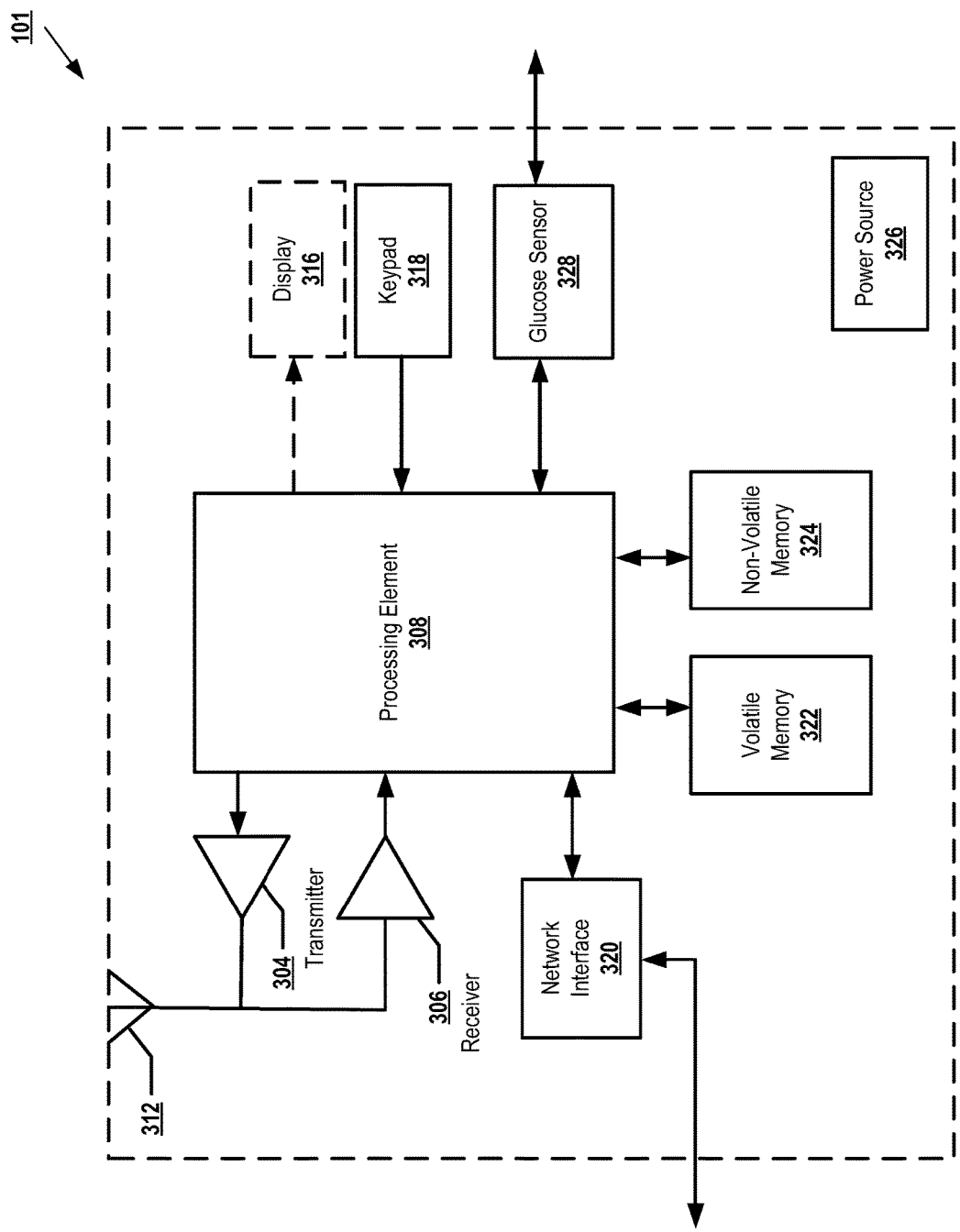

FIG. 3 provides an example glucose monitoring computing entity, in accordance with some embodiments discussed herein.

Figure 4:
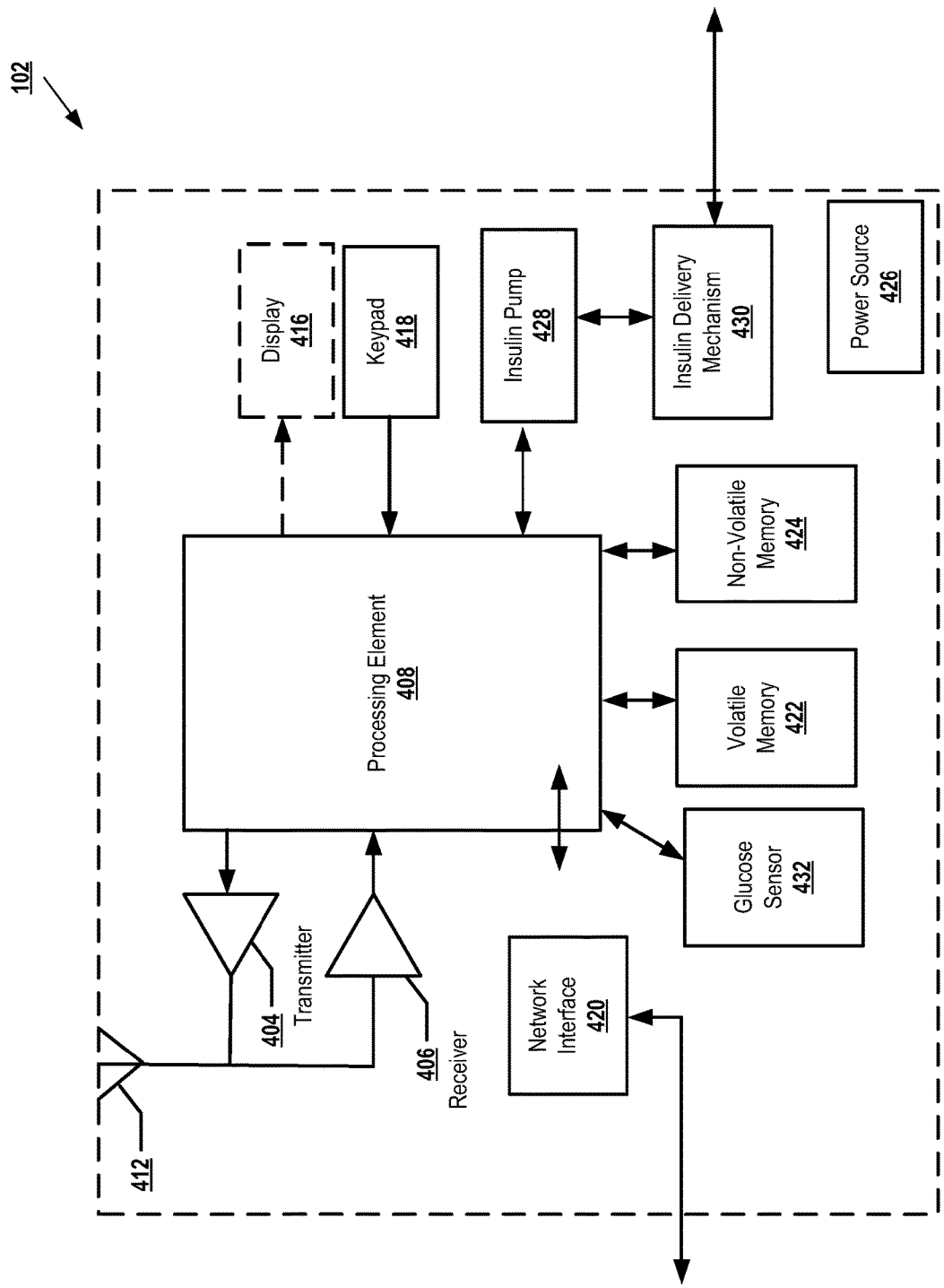

FIG. 4 provides an example automated insulin delivery computing entity, in accordance with some embodiments discussed herein.

Figure 5:
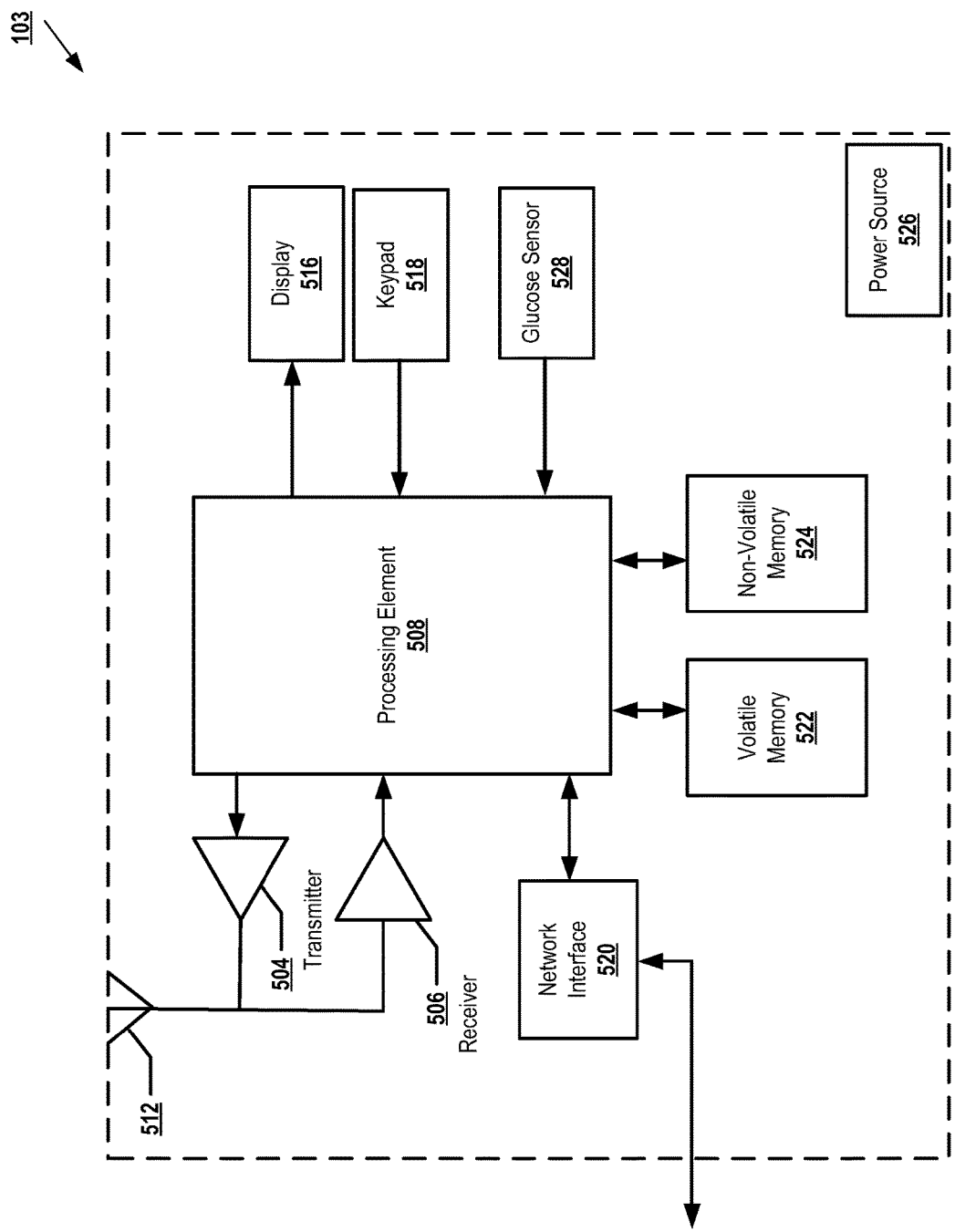

FIG. 5 provides an example client computing entity, in accordance with some embodiments discussed herein.

Figure 6:
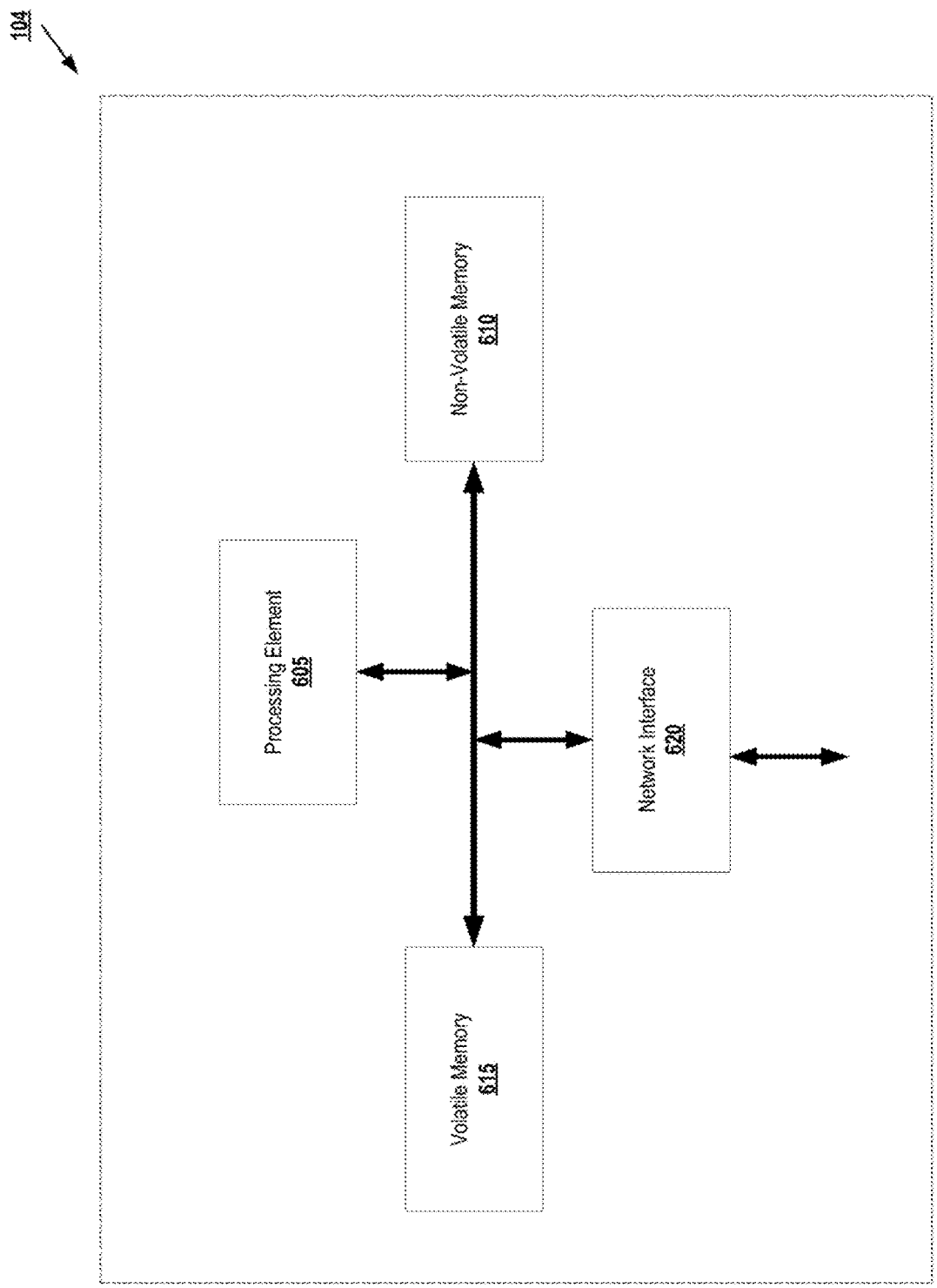

FIG. 6 provides an example external computing entity, in accordance with some embodiments discussed herein.

Figure 7:
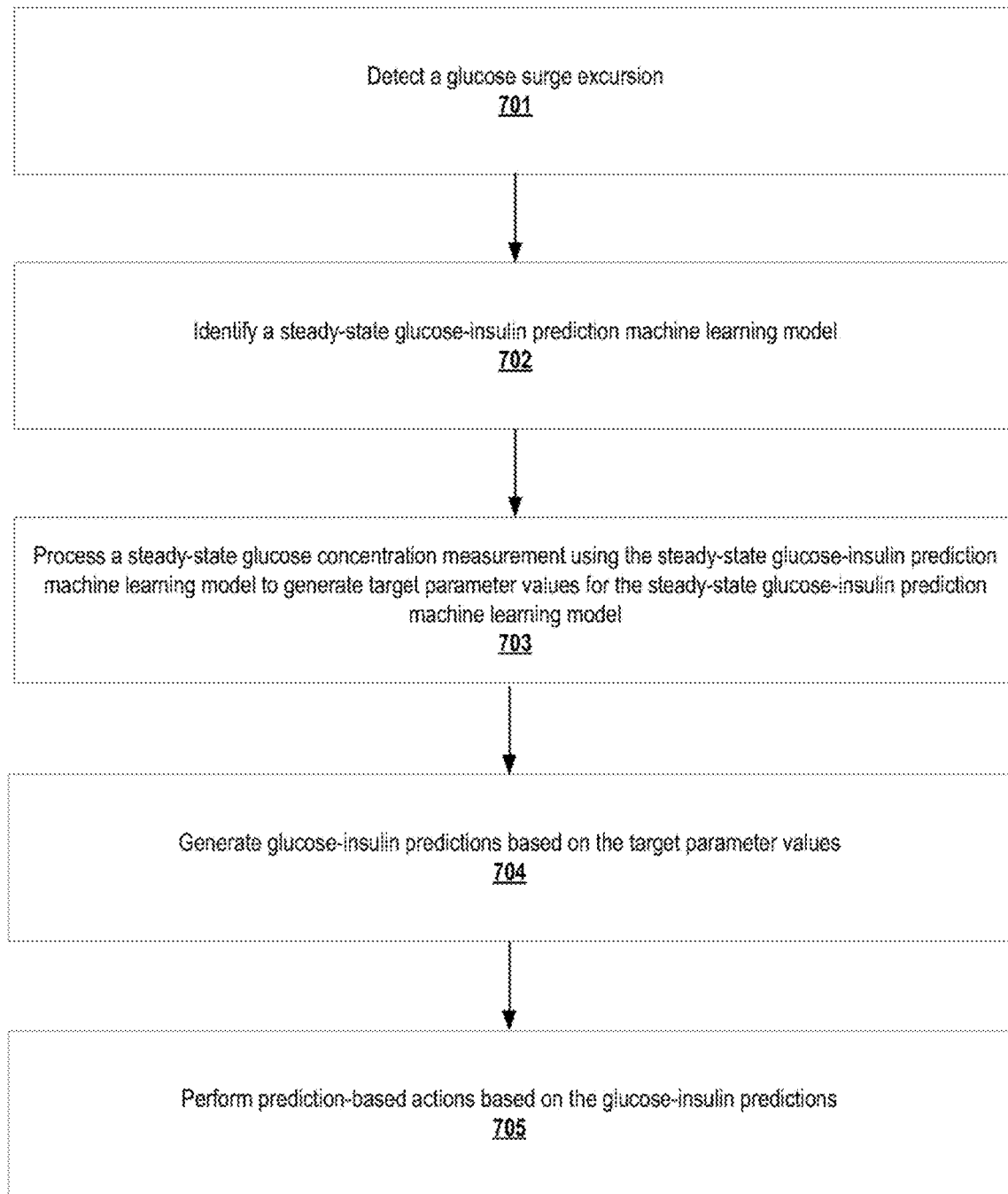

FIG. 7 is a flowchart diagram of an example process for performing predictive monitoring of the glucose-insulin endocrine metabolic regulatory system of a corresponding monitored end-user, in accordance with some embodiments discussed herein.

Figure 8:
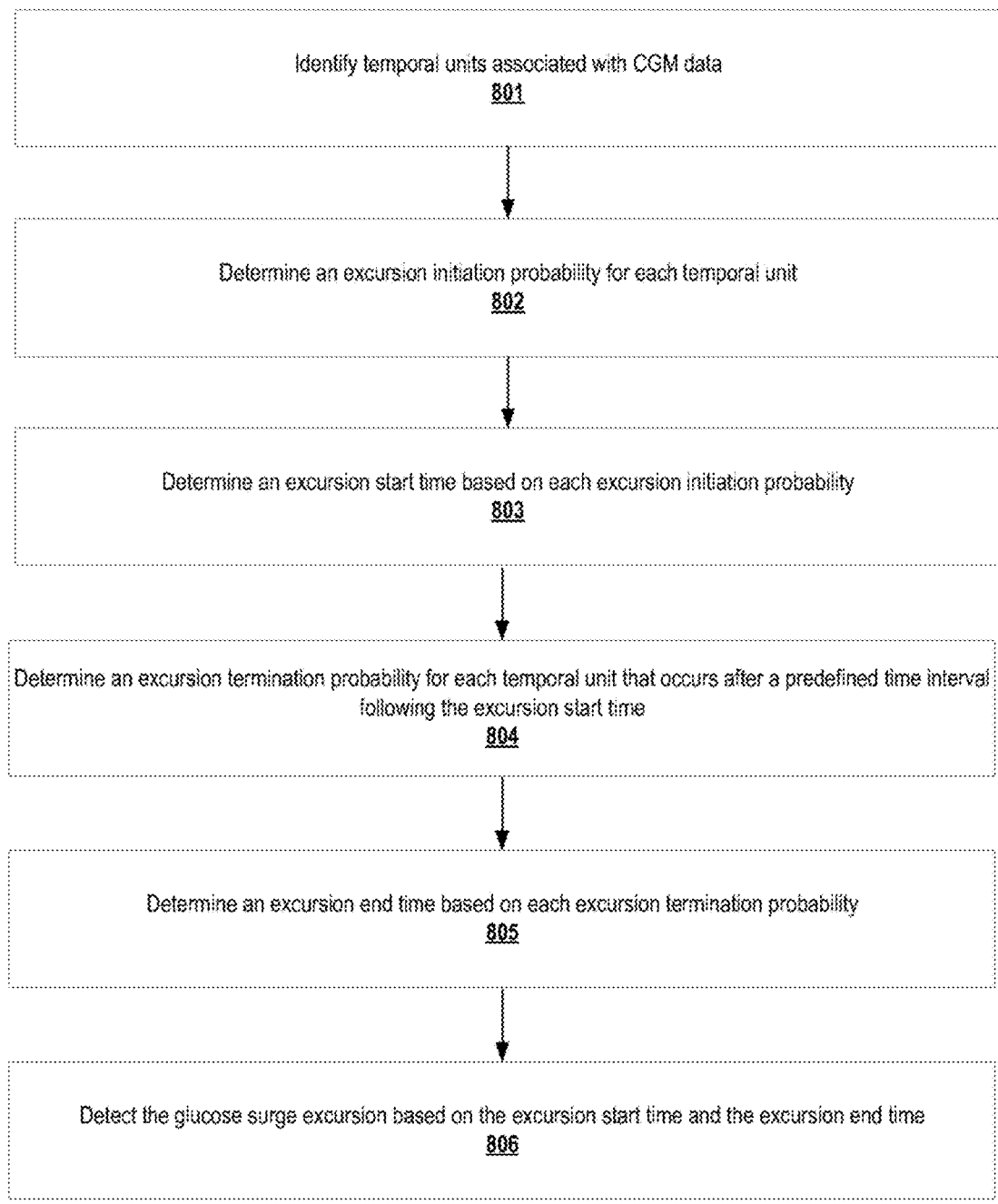

FIG. 8 is a flowchart diagram of an example process for detecting a glucose surge excursion, in accordance with some embodiments discussed herein.

Figure 9:
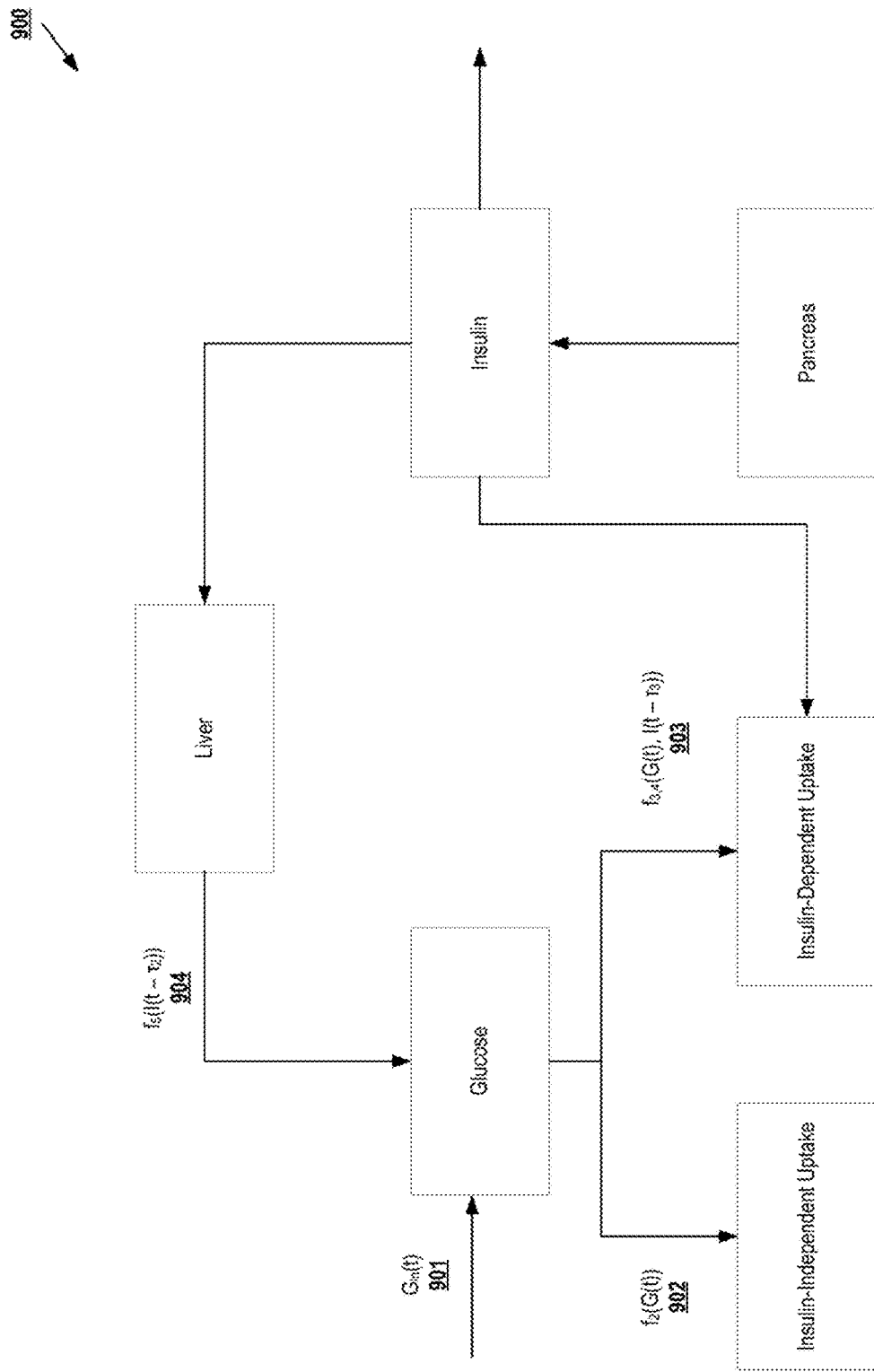

FIG. 9 is a contextual flow diagram of an example process for generating a glucose concentration change prediction using a general hybrid glucose-insulin prediction machine learning model, in accordance with some embodiments discussed herein.

Figure 10:
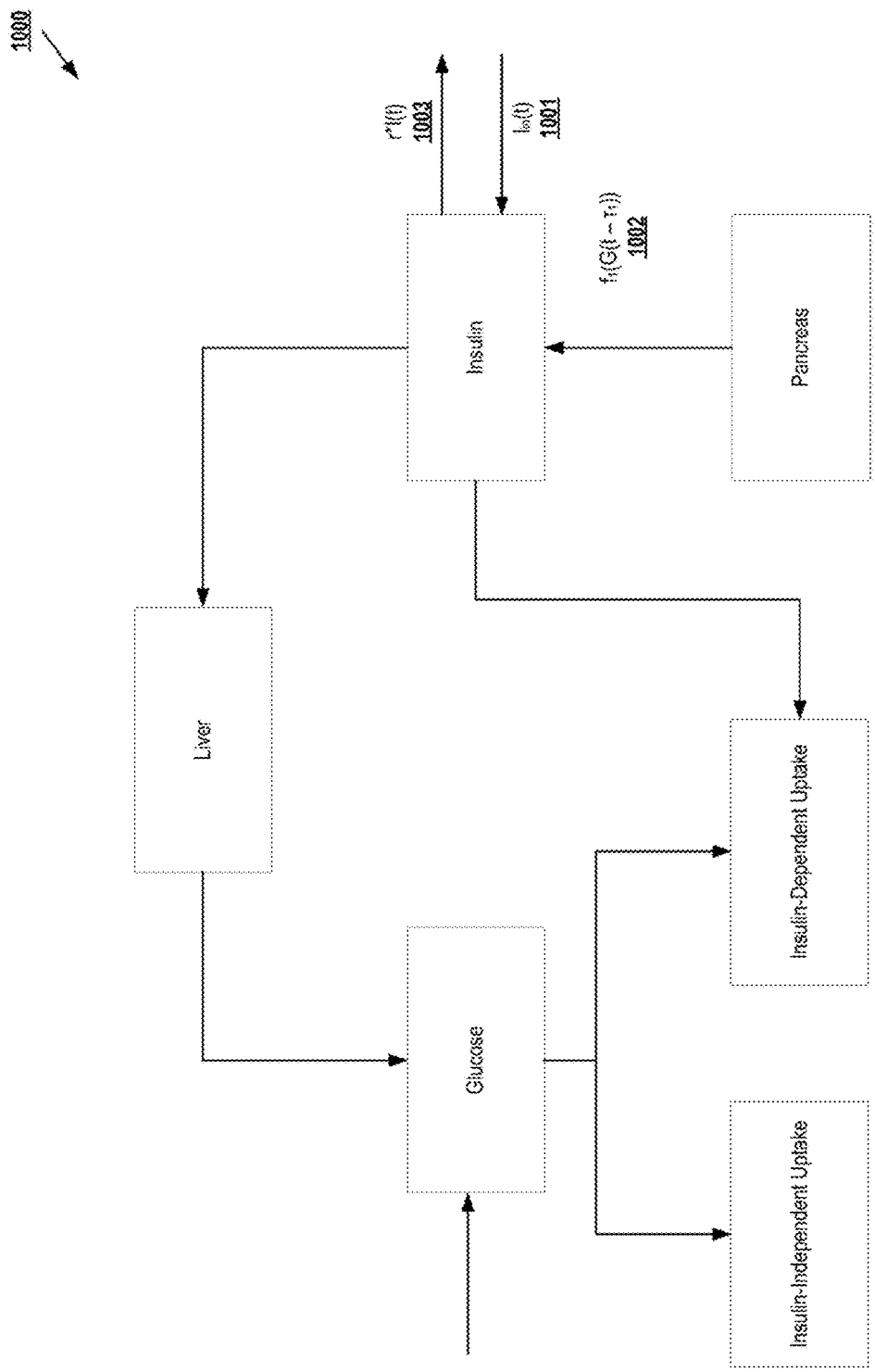

FIG. 10 is a contextual flow diagram of an example process for generating a plasma insulin concentration change prediction using a general hybrid glucose-insulin prediction machine learning model, in accordance with some embodiments discussed herein.

Figure 11:
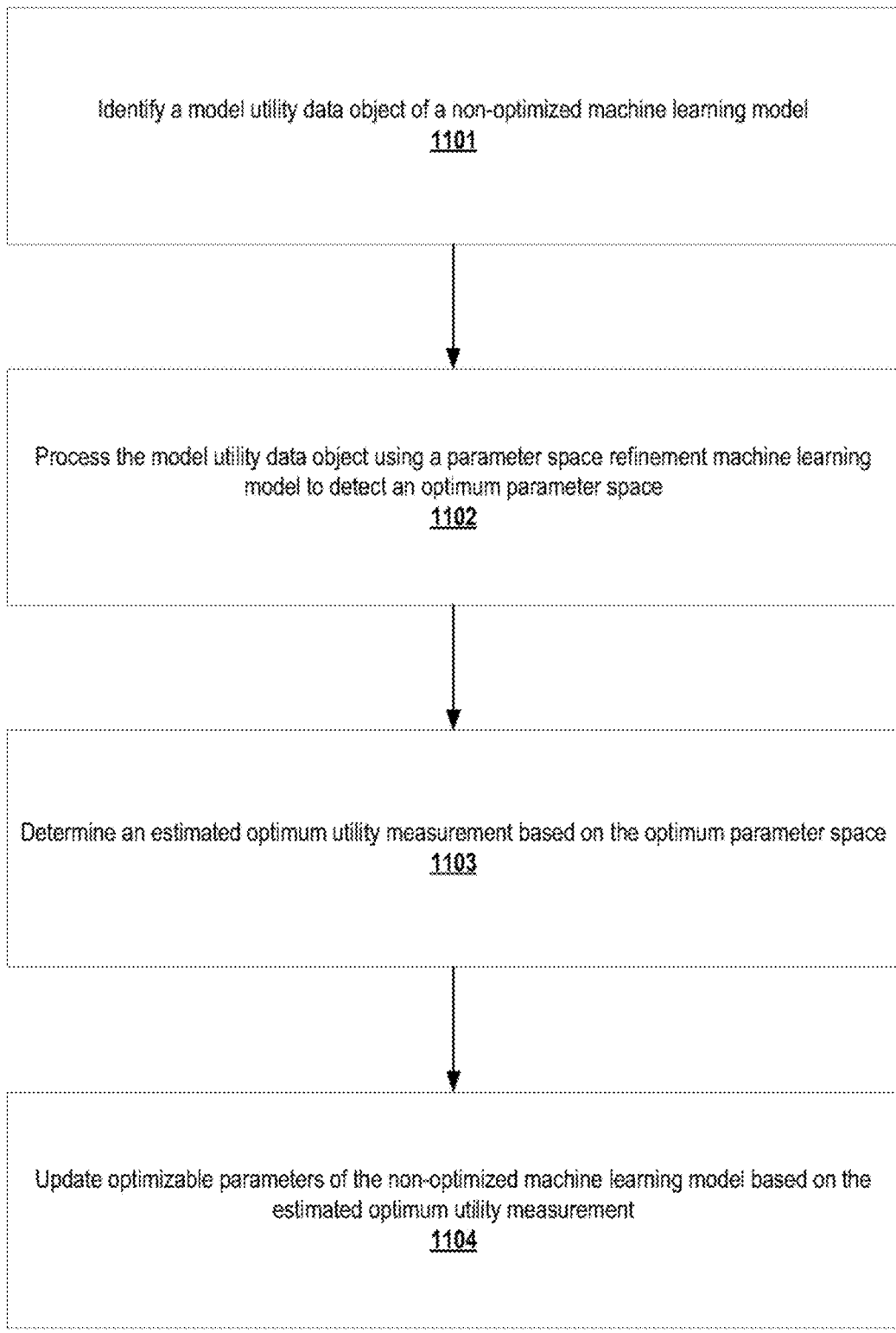

FIG. 11 is a flowchart diagram of an example process for performing parameter optimization for a machine learning model by using a parameter space refinement machine learning model, in accordance with some embodiments discussed herein.

Figure 12:
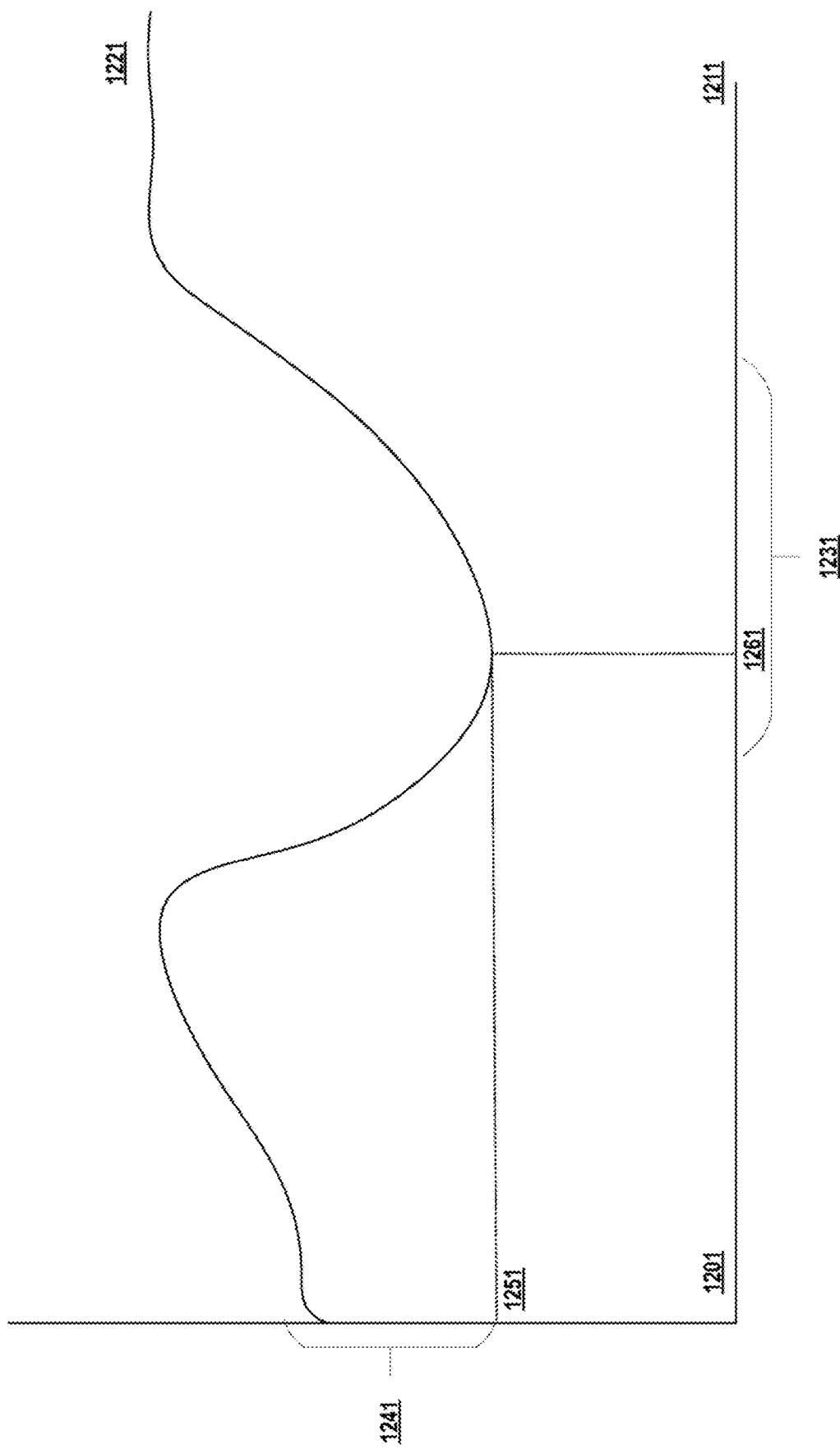

FIG. 12 provides an operational example of detecting an optimum parameter space for a model utility data object, in accordance with some embodiments discussed herein.

Figure 13:
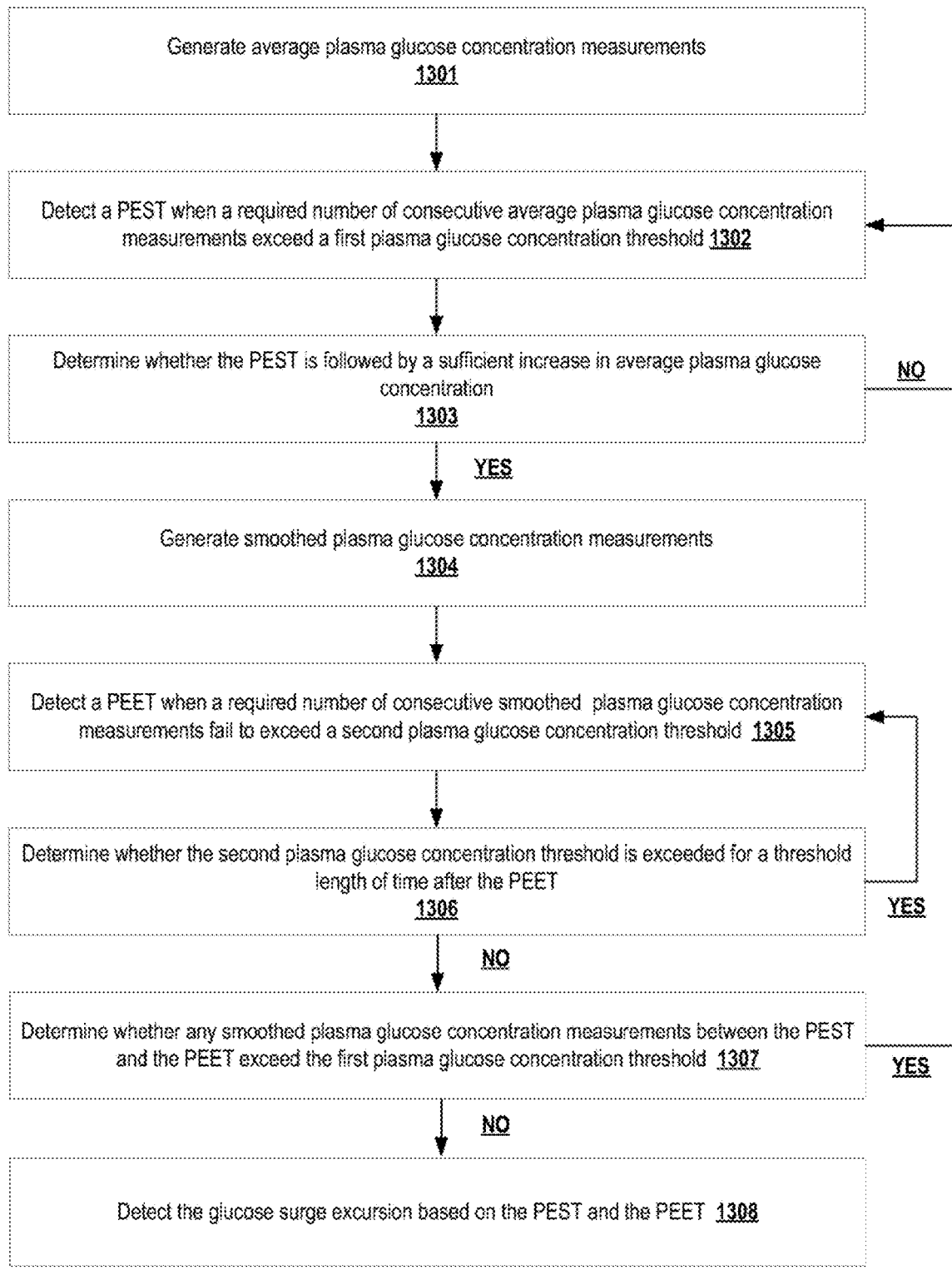

FIG. 13 is a flowchart diagram of an example process for detecting a glucose surge excursion using average glucose concentration measurements, in accordance with some embodiments discussed herein.

Figure 14:
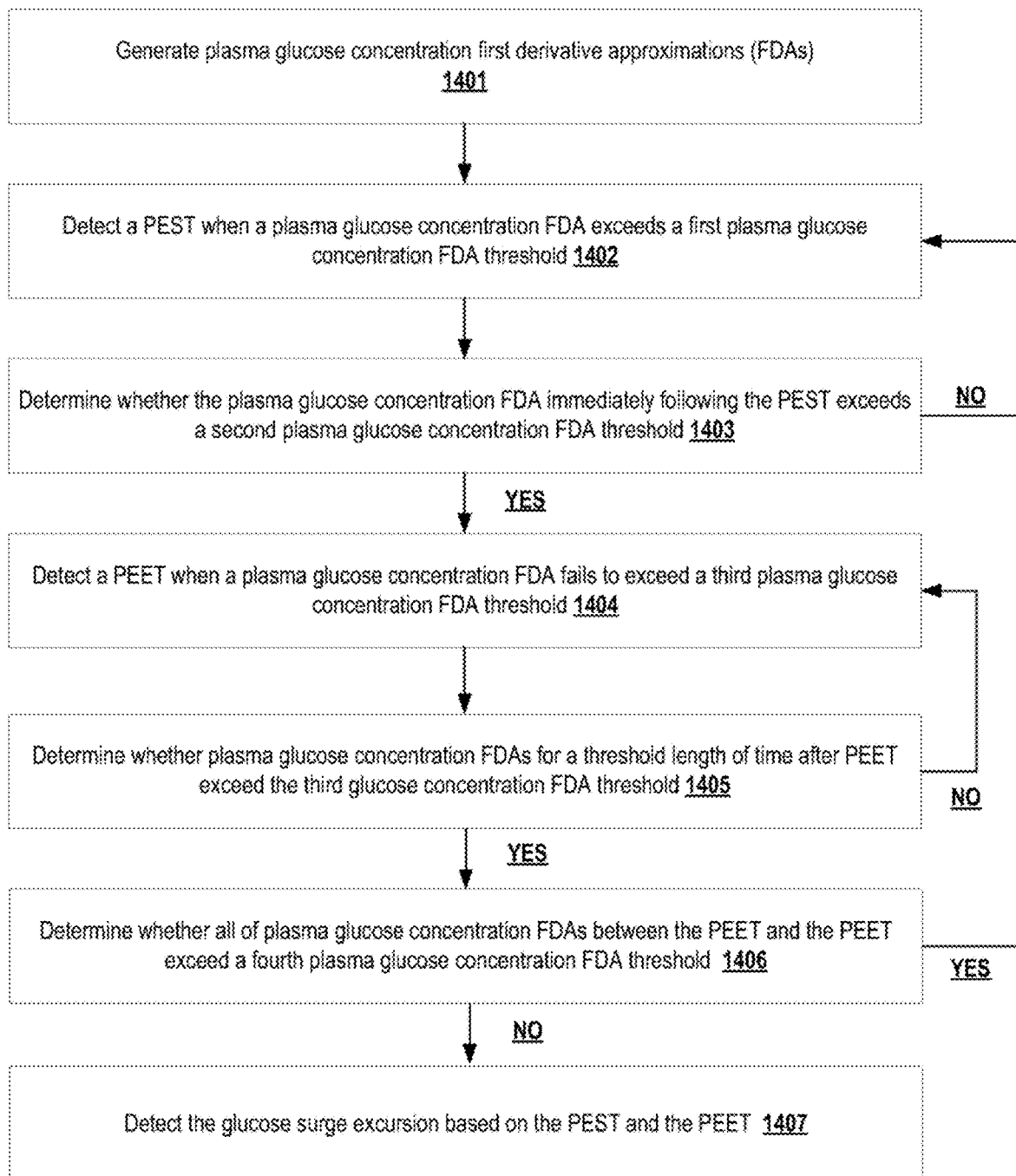

FIG. 14 is a flowchart diagram of an example process for detecting a glucose surge excursion using glucose concentration first derivative approximations, in accordance with some embodiments discussed herein.

Figure 15:
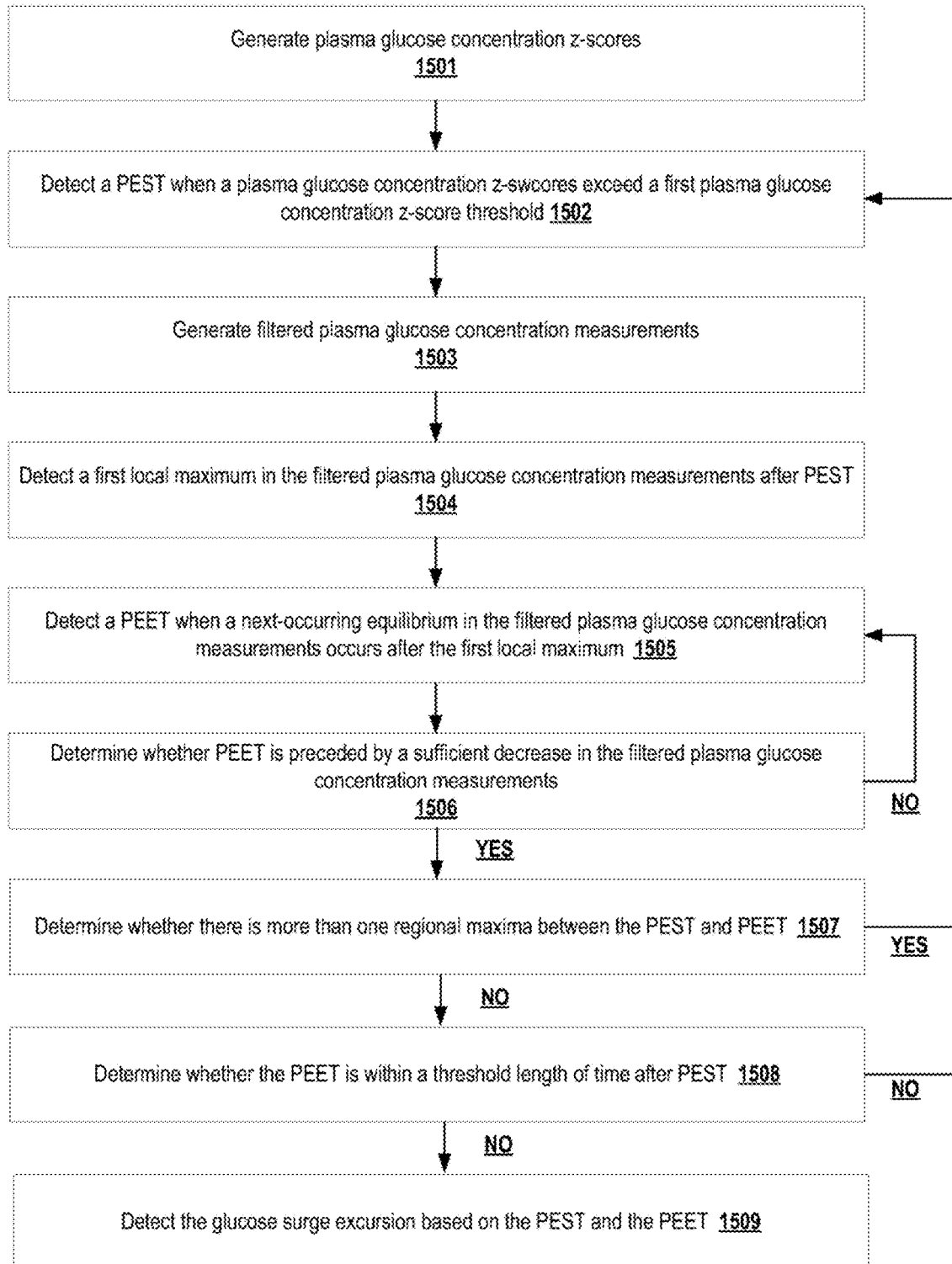

FIG. 15 is a flowchart diagram of an example process for detecting a glucose surge excursion using glucose concentration z-scores, in accordance with some embodiments discussed herein.

Figure 16:
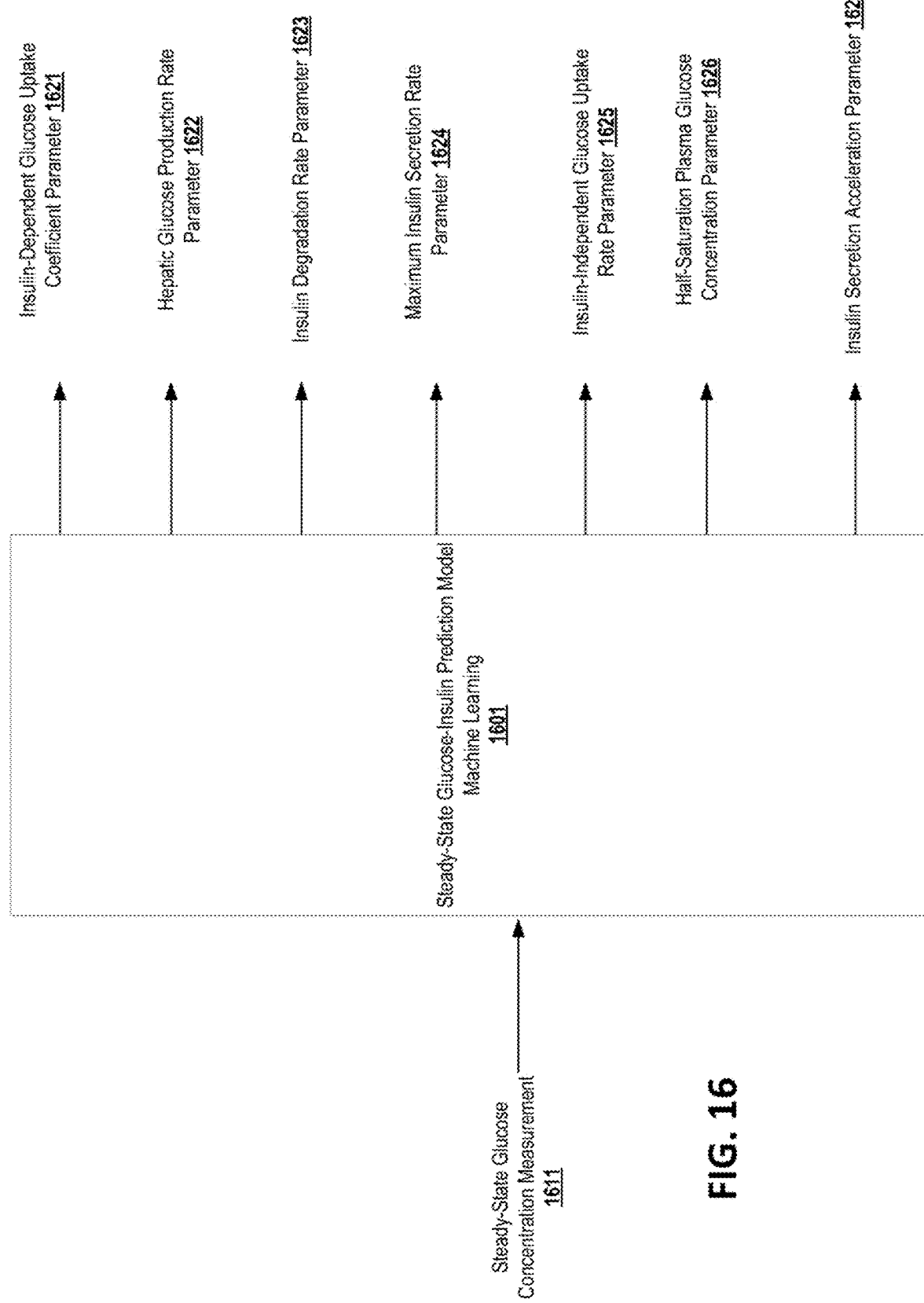

FIG. 16 provides an operational example of a steady-state glucose-insulin prediction machine learning model, in accordance with some embodiments discussed herein.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, one of ordinary skill in the art will recognize that the disclosed concepts can be used to perform other types of data analysis.

I. OVERVIEW

Various embodiments of the present invention make substantial technical improvements to the field of predictive glucose-insulin monitoring by introducing a probabilistic framework for detecting glucose surge excursions that is able to estimate glucose surge excursions based at least in part on statistical properties of glucose concentration measurements, user-initiated actions, and expected maximal lengths of glucose surge excursions. The probabilistic framework provides an efficient and effective means for performing targeted sampling on the glucose monitoring data in order to infer biologically meaningful properties about functioning of the glucose-insulin endocrine metabolic regulatory system. Once glucose surge excursions are determined, data about such glucose surge excursions are supplied to machine learning models that are configured to efficiently and reliably generate glucose-insulin predictions based at least in part on the glucose concentration measurements associated with the noted glucose surge excursions.

Examples of the noted machine learning models used for performing glucose-insulin prediction include steady-state glucose-insulin prediction machine learning models. One important objective behind utilizing the steady-state glucose-insulin prediction machine learning prediction models is that the steady-state glucose-insulin prediction machine learning models have fewer parameters than various other glucose-insulin prediction machine learning models. This in turn means that steady-state glucose-insulin machine learning prediction models are likely to have greater storage efficiency, operational efficiency, and per-parameter optimization accuracy relative to various other glucose-insulin prediction machine learning models.

Furthermore, various embodiments of the present invention introduce techniques for efficient parameter optimization that enable performing quasi-global parameter optimization operations that avoid the computational costs of many existing global parameter optimization techniques yet achieve much of the accuracy and reliability of such global parameter optimization techniques. For example, in some embodiments, a loss function output of a machine learning model is first processed using a parameter space refinement machine learning model (e.g., a parameter space refinement machine learning model that utilizes a convolutional neural network architecture) to identify an optimum parameter space of the loss function output that is estimated to include a global minimum loss value. Thereafter, the identified optimum parameter space is analyzed using a global minima detection technique to identify a minimum loss value for the loss function output.

The parameter optimization concepts discussed herein (including the quasi-global parameter optimization concepts discussed herein) provide powerful tools for performing reliable yet efficient model optimization, a contribution that has major implications for many fields within predictive data analysis. For example, the quasi-global parameter optimization concepts discussed herein are especially conducive to performing model optimization in contexts where local optimization is deemed unreliable (e.g., in the medical context, where the costs of choosing a local optimum rather than a global optimum may be high), but where performing global optimization may be too costly and/or too slow given the system requirements (e.g., in glucose-insulin sensory systems, where expediated processing and feedback may be required or highly desired). As another example, the parameter optimization concepts discussed herein can be utilized to optimize utility functions (e.g., maximize reward functions, minimize loss functions, and/or the like) in the context of training various machine learning models (e.g., neural network machine learning models) that are conducive to optimization-based training techniques.

A key technical advantage of some embodiments of the invention discussed herein is that they enable determining physiologically important measures (e.g., physiologically important measures about functioning of the glucose-insulin endocrine metabolic regulatory system, such as insulin sensitivity measures and beta cell capacity measures) based on continuous glucose monitoring data obtained using minimally invasive methods (e.g., relative to clamp-test-based techniques that are more expensive and more invasive). In doing so, the noted embodiments of the present invention make important technical contributions to the field of physiological monitoring.

II. DEFINITIONS

The term "glucose-insulin prediction" may refer to a data object that describes a conclusion about one or more functional properties of the glucose-insulin endocrine metabolic regulatory system of a corresponding monitored end-user. For example, the glucose-insulin prediction may describe a measure of pancreatic response to accelerate insulin production and insulin secretion in response to increase of glucose concentrations for the corresponding monitored end-user. As another example, the glucose-insulin prediction may describe a maximal measure of insulin production and insulin secretion for the corresponding monitored end-user. As yet another example, the glucose-insulin prediction may describe the combination of an estimated rate of change of the glucose concentration of the corresponding monitored end-user at a particular point in time and an estimated rate of change of the insulin concentration of the corresponding monitored end-user at the particular point in time. As a further example, the glucose-insulin prediction may describe a measure of sensitivity of the liver cells and the muscle/fat cells of the corresponding monitored end-user to performing glucose uptake in response to secretion of insulin by β-cells in pancreas.

The term "glucose surge excursion" may refer to a data object that describes a period of time that is associated with one or more heightened periods of glucose concentration for a corresponding monitored end-user. For example, the glucose surge excursion may describe a period of time that is estimated to include a period of exogenous glucose infusion, such as exogenous glucose infusion through at least one of meal ingestion, oral glucose consumption, continuous enteral nutrition, and constant glucose infusion. As another example, the glucose surge excursion may describe a period of time that is estimated to include a period of hepatic glucose production. As another example, the glucose surge excursion may describe a period of time that is estimated to include both a period of exogenous glucose infusion and a period of hepatic glucose production. As yet another example, the glucose surge excursion may describe a period of heightened glucose concentration for the corresponding monitored end-user, regardless of the source of the noted heightened glucose concentration.

The term "glucose monitoring data" may refer to a data object that describes one or more glucose concentration measurements for a corresponding monitored end-user, where each glucose concentration measurement is associated with a corresponding point in time that is associated with the noted glucose concentration measurement. The glucose monitoring data may be calculated using one or more glucose sensors, where the glucose sensors are configured to record glucose concentration measurements and to transmit (e.g., wirelessly, through a wired transmission medium, and/or the like) the recorded glucose concentration measurements to a computing device configured to store glucose concentration measurements. Examples of glucose sensors may include glucose sensors that are in direct contact with at least one of interstitial fluids, blood, other bodily fluids as well as glucose sensors that are not in direct contact with any of the interstitial fluids, blood, other bodily fluids, or tissues, where the latter category may include glucose sensors that use transmission spectroscopy and glucose sensors that use reflection spectroscopy. In some embodiments, the glucose monitoring data is generated by using one or more glucose sensors that collectively enable continuous glucose monitoring (CGM) for the corresponding monitored end-user. In some embodiments, CGM sensors do not directly measure glucose concentration measurements, but instead measure interstitial glucose concentration measurements. In general, while various embodiments of the present invention discuss glucose concentration measurements, all the concepts of the present invention can be performed using interstitial glucose concentration measurements and/or using a combination of interstitial glucose concentration measurements and glucose concentration measurements.

The term "continuous glucose monitoring (CGM)" may refer to a computer-implemented process that includes recording plasma glucose concentration measurements for a corresponding monitored end-user with a continuous frequency and/or with a quasi-continuous frequency, where recording glucose concentration measurements with quasi-continuous frequency may include recording glucose concentration measurements with a frequency deemed sufficiently high to enable measurement of glucose concentrations with an estimated degree of reliability that is deemed to be equivalent to the estimated degree of reliability of measurement of glucose concentrations with continuous frequency. Accordingly, it is important to note that CGM does not require that readings be instantaneous or absolutely continuous. In some embodiments, CGM devices provide glucose concentration measurements every five to ten minutes. This frequency may be driven by the need for fidelity of control and by the fact that the most patient-friendly place to sample blood is in the periphery and peripheral blood measurements lag portal measurement, as taking samples over five minutes may reduce the probability that no single abnormal reading will cause incorrect insulin dosing. In some embodiments, in micro-dialysis-based CGM, sensors may measure glucose in interstitial fluid, where the glucose levels in the interstitial fluid may lag five or more minutes behind blood glucose levels.

The term "continuous glucose monitoring (CGM) data" may refer to a data object that describes one or more glucose concentration measurements obtained using one or more CGM processes. In some embodiments, CGM may performed by one or more CGM sensors that are configured to record glucose concentration measurements in a continuous manner and/or quasi-continuous manner and to transmit (e.g., wirelessly, through a wired transmission medium, and/or the like) the recorded glucose concentration measurements to a computing device configured to store glucose concentration measurements. Some CGM sensors use a small, disposable sensor inserted just under the skin. A CGM sensor may be calibrated with a traditional finger-stick test and the glucose levels in the interstitial fluid may lag five or more minutes behind blood glucose levels. Some CGM sensors may use non-invasive techniques such as transmission and reflection spectroscopy.

The term "steady-state glucose concentration measurement" may refer to a data object that describes a glucose concentration measurement that is associated with a steady-state time interval associated with a corresponding monitored end-user. In some embodiments, the steady-state glucose concentration measurement describes a measure of statistical distribution of a group of glucose concentration measurements that are deemed to be associated with the steady-state time interval, such as a mean of the group of glucose concentration measurements that are deemed to be associated with the steady-state time interval, a weighted mean of the group of glucose concentration measurements that are deemed to be associated with the steady-state time interval, a median of the group of glucose concentration measurements that are deemed to be associated with the steady-state time interval, a mode of the group of glucose concentration measurements that are deemed to be associated with the steady-state time interval, a maximal value of the group of glucose concentration measurements that are deemed to be associated with the steady-state time interval, a minimal value of the group of glucose concentration measurements that are deemed to be associated with the steady-state time interval, and/or the like. In some embodiments, the steady-state time interval is a singular point in time, and the steady-state glucose concentration measurement describes a glucose concentration measurement associated with the singular point in time.

The term "steady-state time interval" may refer to a data object that describes a time interval within a glucose surge excursion for a corresponding monitored end-user that is estimated to be associated with absence of temporal glucose changes and absence of exogenous glucose infusion. In some embodiments, during the steady-state time interval, all glucose-related derivatives with respect to time (e.g., derivative of glucose concentration with respect to time, derivative of exogenous glucose infusion with respect to time, derivative of hepatic glucose production with respect to time, and/or the like) are deemed to be near-zero values and the rate of exogenous glucose infusion is deemed to be zero. The steady-state time interval may be determined based at least in part on a predefined physiological computational model of the glucose-insulin endocrine metabolic regulatory system and/or may be determined based at least in part on monitoring glucose-related measurements of the corresponding monitored end-user in the past. For example, the steady-state time interval may include at least a portion of a terminal part of a glucose surge excursion, such as a tail end of a glucose surge excursion. In some embodiments, the steady-state time interval includes all of the points in time that satisfy one or more steady-state time interval criteria (e.g., all of the points in time within a detected tail end of a glucose surge excursion). In some embodiments, the steady-state time interval includes only a selected number of points in time that are selected (e.g., randomly or in accordance with one or more selection criteria) from the points in time that satisfy one or more steady-state time interval criteria (e.g., a randomly-selected individual point in time from a detected tail end of a glucose surge excursion).

The term "steady-state glucose-insulin prediction machine learning model" may refer to a data object that describes parameters and/or hyperparameters of a machine learning model that is configured to relate a cross-steady-state parameter for a corresponding monitored end-user to a steady-state glucose concentration measurement of the corresponding monitored end-user. Accordingly, the steady-state glucose-insulin prediction machine learning model may be utilized to generate estimated values for the cross-steady-state parameters based at least in part on the steady-state glucose concentration measurement of the corresponding monitored end-user, for example by determining a combination of estimated values for the cross-steady-state parameters that, when processed in accordance with the operations defined by the steady-state glucose-insulin prediction machine learning model, generates an inferred steady-state glucose concentration measurement that most closely aligns with the steady-state glucose concentration measurement. In some embodiments, the steady-state glucose-insulin prediction machine learning model may be configured to relate the steady-state glucose concentration measurement to at least one of the following cross-steady-state parameter values: (i) an insulin-dependent glucose uptake coefficient parameter value; (ii) a hepatic glucose production rate parameter value; (iii) an insulin degradation rate parameter value; (iv) a maximal insulin secretion rate parameter value; (v) an insulin-independent glucose uptake rate parameter value; (vi) a half-saturation glucose concentration parameter value; and (vii) an insulin secretion acceleration parameter value. The steady-state glucose insulin prediction machine learning model may be determined by removing glucose-insulin temporal derivative factors and an exogenous glucose infusion factor from a glucose-biased glucose-insulin prediction machine learning model.

The term "cross-steady-state parameter" may refer to a data object that describes a functional property of the glucose-insulin endocrine metabolic regulatory system of a corresponding monitored end-user that is deemed to be true across the entirety of a glucose surge excursion, including any portion of the glucose surge excursion that occurs before a corresponding steady-state time interval and any portion of the glucose surge excursion that occurs after the corresponding steady-state time interval. Examples of cross-steady-state parameters include an insulin-dependent glucose uptake coefficient parameter, a hepatic glucose production rate parameter, an insulin degradation rate parameter, a maximal insulin secretion rate parameter, an insulin-independent glucose uptake rate parameter, a half-saturation glucose concentration parameter, and/or an insulin secretion acceleration parameter. In some embodiments, a cross-steady-state parameter describes a functional property of the glucose-insulin endocrine metabolic regulatory system of a corresponding monitored end-user whose value is not a function of the glucose concentration and the plasma insulin concentration.

The term "target parameter" may refer to a data object that describes a cross-steady-state parameter that is in a subset of the cross-steady-state parameters of a corresponding steady-state glucose-insulin prediction machine learning model that is deemed related to generating a corresponding glucose-insulin prediction. For example, if the corresponding glucose-insulin prediction describes a measure of sensitivity of the liver cells and the muscle/fat cells of the corresponding monitored end-user to performing glucose uptake in response to secretion of insulin by β-cells in pancreas, the target parameters may include at least one of the maximal insulin secretion rate parameter, the insulin-independent glucose uptake coefficient parameter, and the insulin secretion acceleration parameter. As another example, if the corresponding glucose-insulin prediction describes a measure of insulin effectiveness rate, the target parameters may include at least one of the maximal insulin secretion rate parameter and the insulin secretion acceleration parameter.

The term "glucose-biased glucose-insulin prediction machine learning model" may refer to a data object that describes parameters and/or hyperparameters of a machine learning model that is configured to relate a group of glucose-concentration-related measurements for a corresponding monitored end-user to desired parameters that describe functional properties of the glucose-insulin endocrine metabolic regulatory system of the corresponding monitored end-user. For example, the glucose-biased glucose-insulin prediction machine learning model may describe a machine learning model that is configured to relate the following: (i) a current glucose concentration; (ii) a delayed glucose concentration; (iii) a derivative of glucose concentration function with respect to time calculated at the current time; (iv) a current exogeneous glucose infusion rate; (v) a derivative of exogeneous glucose infusion rate function with respect to time calculated at the current time; (vi) an insulin-independent glucose uptake coefficient parameter; (vii) a hepatic glucose production rate parameter; (viii) an insulin degradation rate parameter; (ix) a maximal insulin secretion rate parameter; (x) an insulin-independent glucose uptake rate parameter; (xi) a half-saturation glucose concentration parameter value; and (xii) an insulin secretion acceleration parameter value. The glucose-biased glucose-insulin prediction machine learning model may be generated by substituting insulin-related factors with glucose-related factors in a hybrid glucose-insulin prediction machine learning model.

The term "hybrid glucose-insulin prediction machine learning model" may refer to a data object that describes parameters and/or hyperparameters of a machine learning model that is configured to relate a group of glucose-concentration-related measurements and a group of insulin-concentration-related measurements for a corresponding monitored end-user to desired parameters that describe functional properties of the glucose-insulin endocrine metabolic regulatory system of the corresponding monitored end-user. For example, the glucose-biased glucose-insulin prediction machine learning model may describe a machine learning model that is configured to relate a derivative of glucose concentration function with respect to time that is evaluated at a current time to the following: (i) a current glucose concentration; (ii) a current exogeneous glucose infusion rate; (iii) a hepatic glucose production rate parameter; (iv) an insulin-independent glucose uptake coefficient parameter; and (v) a current plasma insulin concentration. As another example, the glucose-biased glucose-insulin prediction machine learning model may describe a machine learning model that is configured to relate a derivative of plasma insulin concentration function with respect to time that is evaluated at a current time to the following: (i) a delayed glucose concentration; (ii) a current plasma insulin concentration; (iii) an insulin degradation rate parameter; (iv) a maximal insulin secretion rate parameter; (v) a half-saturation glucose concentration parameter value; and (vi) an insulin secretion acceleration parameter value. As yet another example, the glucose-biased glucose-insulin prediction machine learning model may describe a machine learning model that is configured to relate a current exogenous glucose infusion rate to the following: (i) a time parameter describing the current time; (ii) a measure of glucose magnitude (e.g., in milligrams) following initiation of an activity that leads to exogenous glucose infusion (e.g., consumption of a meal); (iii) plasma glucose distribution volume (e.g., in deciliters); and (iv) a glucose concentration peak interval parameter, where (ii)-(iv) may be predefined values.

The term "exogenous glucose infusion rate" may refer to a data object that describes the rate at which glucose concentration of a corresponding monitored end-user increases following a particular exogenous glucose infusion event, such as at least one of meal ingestion, oral glucose consumption, continuous enteral nutrition, and constant glucose infusion. Exogenous glucose infusion rate may be calculated based at least in part on a model that relates a current exogenous glucose infusion rate to the following: (i) a time parameter describing the current time; (ii) a measure of glucose magnitude following initiation of an activity that leads to exogenous glucose infusion (e.g., consumption of a meal); (iii) plasma glucose distribution volume; and (iv) a glucose concentration peak interval, where (ii)-(iv) may be predefined values. The exogenous glucose infusion rate may be expressed as milligrams per deciliter times inverse of a minute ($mg/dl*min^{-1}$).

The term "insulin-dependent glucose uptake coefficient parameter" may refer to a data object that describes a coefficient related to the rate at which cells of a corresponding monitored end-user utilize glucose in response to receiving insulin at their insulin receptors. Insulin-dependent glucose uptake includes glucose utilization by insulin receptors of muscle cells, fat cells, and other tissue cells, where the noted insulin receptors receive insulin and in response activate a signaling cascade for GLUT4 translocation, which in turn causes the cells to consume the glucose and convert it to energy. As modeled herein, insulin-dependent glucose uptake is the output of a function of both glucose concentrations and plasma insulin concentrations. The insulin-dependent glucose uptake coefficient parameter may take a value that is expressed as the inverse of atomic mass units per milliliters times inverse of a minute ($(U/ml*min)^{-1}$).

The term "hepatic glucose production rate parameter" may refer to a data object that describes the estimated rate at which liver cells of a corresponding monitored end-user produce and secrete insulin in response to production and insulin secretion of glucagon by α-cells in the liver of the corresponding monitored end-user, where the noted glucagon production and insulin secretion may exert control over metabolic pathways in the liver in a manner that leads to glucose production. The hepatic glucose production rate parameter may take a value that is described as milligrams per deciliter times inverse of a minute ($mg/dl*min^{-1}$).

The term "insulin degradation rate parameter" may refer to a data object that describes the estimated rate at which insulin is cleared by insulin-sensitive tissues of a corresponding monitored end-user. Insulin clearance activities may be performed by liver, kidney, muscle, adipose cells, and other tissues. The insulin degradation rate parameter may be a factor in an insulin degradation rate function that applies the insulin degradation rate parameter to the plasma insulin concentration. The insulin degradation parameter may take a value that is described as the number of insulin molecules that are degraded by insulin-sensitive tissues in each minute ($min^{-1}$).

The term "maximal insulin secretion rate parameter" may refer to a data object that describes the estimated maximal rate at which β-cells in pancreas of a corresponding monitored end-user can produce and secrete insulin in response to elevated glucose concentrations in the bloodstream of the corresponding monitored end-user. The maximal insulin secretion rate parameter may take a value that is expressed as atomic mass units per milliliter times inverse of a minute ($U/ml*min^{-1}$).

The term "insulin-independent glucose uptake rate parameter" may refer to a data object that describes the estimated rate at which cells of a corresponding monitored end-user utilize glucose, where the noted glucose utilization is performed independent of insulin secretion. Insulin-independent glucose utilization is performed by the brain cells and cells of the nervous system as well as through urination. As modeled herein, insulin-independent glucose utilization is a computational model of glucose plasma concentration. The insulin-independent glucose uptake rate parameter may take a value that is expressed as the number of glucose molecules that are utilized using insulin-independent glucose uptake in each minute ($min^{-1}$).

The term "half-saturation glucose concentration parameter" may refer to a data object that describes an estimated measure of glucose concentration at a point in time in which half of a maximal degree of possible glucose uptake has been performed for a corresponding monitored end-user. The half-saturation glucose concentration parameter can be utilized as a measure of glucose uptake capability of a monitored end-user. The half-saturation glucose concentration parameter can take a value that is expressed as milligrams per deciliter (mg/dl).

The term "insulin secretion acceleration parameter" may refer to a data object that describes an estimated measure of the rate at which β-cells of pancreas of a corresponding monitored end-user accelerate insulin production and insulin secretion when the noted β-cells detect heightened levels of glucose concentration in the bloodstream of the corresponding monitored end-user. The insulin secretion acceleration parameter may take the form of an exponential parameter. In some embodiments, the hybrid glucose-insulin prediction machine learning model models insulin secretion by β-cells as a Hill function which includes the insulin secretion acceleration parameter as the Hill coefficient. In some of the noted embodiments, the steady-state glucose-insulin prediction machine learning model inherits the Hill coefficient from the hybrid glucose-insulin prediction machine learning model, as the Hill coefficient survives both the derivation of the glucose-biased glucose-insulin prediction machine learning model from the hybrid glucose-insulin prediction machine learning model as well as the derivation of the steady-state glucose-insulin prediction machine learning model from the glucose-biased glucose-insulin prediction machine learning model.

The term "insulin secretion time delay parameter" may refer to a data object that describes an estimated measure of temporal delay between appearance of heightened glucose concentrations in the bloodstream of a corresponding monitored end-user and a time associated with insulin secretion by β-cells of the pancreas. For example, the insulin secretion time delay parameter may describe the estimated measure of temporal delay between appearance of heightened glucose concentrations in the bloodstream of the corresponding monitored end-user and a time associated with initiation of insulin secretion by β-cells of the pancreas. As another example, the insulin secretion time delay parameter may describe the estimated measure of temporal delay between appearance of heightened glucose concentrations in the bloodstream of the corresponding monitored end-user and a time associated with termination of insulin secretion by β-cells of the pancreas.

The term "glucose concentration peak interval parameter" may refer to a data object that describes an estimated length of a time between the first appearance of the glucose in the bloodstream of a corresponding monitored end-user as a result of a exogenous glucose infusion and peak of glucose in the blood stream of the corresponding monitored end-user as a result of the exogenous glucose infusion. For example, the glucose concentration peak interval parameter may describe a time delay between first appearance of exogenously-infused glucose in the bloodstream of the monitored end-user as a result of a meal ingestion and a peak of meal absorption. The glucose concentration peak interval parameter may take a value that is expressed as minutes (min).

The term "excursion initiation probability" may refer to a data object that describes an estimated likelihood that a corresponding temporal unit is the beginning point of a glucose surge excursion. The excursion initiation probability for a corresponding temporal unit may be determined based at least in part on at least one of statistical distributional properties of the glucose concentration measurement associated with the temporal unit and a user-supplied meal session initiation indicator for the temporal unit (e.g., upon detecting a user-supplied meal session initiation indicator, an excursion imitation probability of one may be determined). For example, the excursion initiation probability for a corresponding temporal unit may increase if a neighboring CGM moving average for the temporal unit exceeds a neighboring CGM moving average threshold. As another example, the excursion initiation probability for a corresponding temporal unit may increase if a CGM first derivative approximation for the temporal unit exceeds a CGM first derivative approximation threshold. As yet another example, the excursion initiation probability for a corresponding temporal unit may increase if a CGM z-score for the temporal unit exceeds a CGM z-score threshold. As a further example, the excursion initiation probability for a corresponding temporal unit may increase if the user-supplied meal session initiation indicator for the temporal unit describes that the temporal unit is associated with initiation of a meal ingestion session.

The term "excursion termination probability" may refer to a data object that describes an estimated likelihood that a corresponding temporal unit is the end point of a glucose surge excursion. The excursion termination probability for a corresponding temporal unit may be determined based at least in part on at least one of statistical distributional properties of the glucose concentration measurement associated with the temporal unit and a user-supplied meal session termination indicator for the temporal unit. For example, the excursion termination probability for a corresponding temporal unit may increase if a neighboring CGM moving average for the temporal unit fails to exceed a neighboring CGM moving average threshold. As another example, the excursion termination probability for a corresponding temporal unit may increase if a CGM first derivative approximation for the temporal unit fails to exceed a CGM first derivative approximation threshold. As yet another example, the excursion termination probability for a corresponding temporal unit may increase if a CGM z-score for the temporal unit fails to exceed a CGM z-score threshold. As a further example, the excursion termination probability for a corresponding temporal unit may increase if the user-supplied meal session termination indicator for the temporal unit describes that the temporal unit is associated with termination of a meal ingestion session.

The term "user-supplied meal session initiation indicator" may refer to a data object that describes whether the temporal unit is associated with a user-initiated action (e.g., pressing of a button on a client computing entity, opening of a meal container with strategically-positioned touch-based sensors that trigger transmission of events to the client computing entity 103 when the meal container has been opened, and/or the like) by a corresponding monitored end-user, where the user-initiated action describes whether the monitored end-user has engaged in a physical activity that is likely to lead to heightened glucose concentrations. In some embodiments, the user-supplied meal session initiation indicator for a corresponding temporal unit describes that the monitored end-user has engaged in a physical activity that is likely to lead to heightened glucose concentrations if the timestamp of the recorded physical activity is within a delay interval of the corresponding temporal unit. In some embodiments, the delay interval may be calculated based at least in part on an at least one of a recorded consumption time, a default consumption time (e.g., an experimentally-determined average consumption time for an individual), and the glucose concentration peak interval for the monitored individual.

The term "user-supplied meal session termination indicator" may refer to a data object that describes whether the temporal unit is associated with a user-initiated action by a corresponding monitored end-user, where the user-initiated action describes whether the monitored end-user has engaged in a physical activity that is likely to lead to termination of a period of heightened glucose concentrations. In some embodiments, the user-supplied meal session termination indicator for a corresponding temporal unit describes that the monitored end-user has ceased engagement in a physical activity that is likely to lead to heightened glucose concentrations if the timestamp of the recorded physical activity is within a delay interval of the corresponding temporal unit. In some embodiments, the delay interval may be calculated based at least in part on at least one of a recorded consumption time, a default consumption time (e.g., an experimentally determined average consumption time for an individual), and the glucose concentration peak interval for the monitored individual. An example of an excursion initiation detection machine learning model is a neural network model.

The term "excursion initiation detection machine learning model" may refer to a data object that describes parameters and/or hyper-parameters of a machine learning model that is configured to process the CGM measurements associated with a corresponding temporal unit to generate an excursion initiation probability for the corresponding temporal unit. In some embodiments, the excursion initiation probability for a temporal unit of the plurality of temporal units is determined by providing CGM measurements associated with the temporal unit to the excursion initiation detection machine learning model. In some embodiments, the excursion initiation detection machine learning model is trained using ground-truth data determined based at least in part on user-supplied meal session initiation indicators.

The term "excursion termination detection machine learning model" may refer to a data object that describes parameters and/or hyper-parameters of a machine learning model that is configured to process the CGM measurements associated with a corresponding temporal unit to generate an excursion termination probability for the corresponding temporal unit. In some embodiments, the excursion termination probability for a temporal unit of the plurality of temporal units is determined by providing CGM measurements associated with the temporal unit to the excursion initiation detection machine learning model. In some embodiments, the excursion initiation detection machine learning model is trained using ground-truth data determined based at least in part on user-supplied meal session termination indicators. An example of an excursion termination detection machine learning model is a neural network model.

The term "model utility data object" may refer to a data object that describes: (i) one or more parameter value combinations, where each parameter value combination includes a candidate value for each optimizable parameter of one or more optimizable parameters of a corresponding machine learning model; and (ii) for each parameter value combination, a utility measurement. For example, the model utility data object may describe a loss function of a machine learning model, as the loss function maps each parameter value combination associated with the machine learning model to a loss value (an example of a utility measurement). As another example, the model utility data object for a steady-state glucose-insulin prediction machine learning model may describe, for each parameter value combination that includes a candidate value for each cross-steady-state parameter of the steady-state glucose-insulin prediction machine learning model, a measure of deviation of an inferred steady-state glucose concentration measurement determined by processing the parameter value combination using the steady-state glucose-insulin prediction machine learning model from a ground-truth steady-state glucose concentration measurement determined based at least in part on glucose monitoring data.

The term "parameter space refinement machine learning model" may refer to a data object that describes parameters and/or hyper-parameters of a machine learning model that is configured to process model utility data objects to identify optimum parameter spaces for the machine learning models that are associated with the noted model utility data objects. For example, the parameter space refinement machine learning model may be a convolutional neural network model that is configured to process an image representation of the model utility data object to determine an optimum image region of the image representation, where the optimum parameter space may be determined based at least in part on the optimum image region. As another example, the parameter space refinement machine learning model may be a recurrent neural network model configured to process the one or more utility measurements in a sequential manner to generate a final hidden state for an ultimate timestep of the recurrent neural network, where the final hidden state is used to generate an encoded representation of the optimum parameter space and the optimum parameter space is determined based at least in part on the encoded representation of the optimum parameter space.

The term "optimum parameter space" may refer to a data object that describes a subset of the parameter space of a machine learning model, where the subset of the parameter space describes, for each optimizable parameter associated with the machine learning model, a subrange of the total range of the optimizable parameter, and where the subset of the parameter space is estimated to include an optimum combination of values for the optimizable parameters associated with the machine learning model (e.g., an optimum parameter value combination that generates a locally optimum utility measurement, an optimum parameter value combination that generates a globally optimum utility measurement, and/or the like). For example, if a machine learning model is associated with a first optimizable parameter that is in turn associated with a total range [0, 1] and a second optimizable parameter that is in turn associated with the total range [10, 20], an example optimum parameter space for the machine learning model may describe parameter value combinations whose first parameter value falls between [0.2, 0.3] and whose second parameter value is [10.2, 10.3]. In the noted example, the described optimum parameter space includes the parameter value combination whose first parameter value is 0.25 and whose second parameter value combination is 10.2, but it does not include the parameter value combination whose first parameter value is 3.1 and whose second parameter value combination is 10.2.

The term "estimated optimum utility measurement" may refer to a data object that describes a utility measurement that is deemed the optimum utility measurement among all of the utility measurements that are associated with parameter value combinations that fall within a corresponding optimum parameter space. Accordingly, an estimated optimum utility measurement should both be associated with a parameter value combination that falls within the corresponding optimum parameter space and be an estimated/exact optimum utility measurement (e.g., a locally minimum loss value, a globally minimum loss value, a locally maximum utility value, a globally maximum utility value, and/or the like) among all of the utility measurements that are associated with parameter value combinations which fall within the optimum parameter space. The set of all utility measurements that are associated with parameter value combinations which fall within the optimum parameter space is referred to herein as an intra-region utility measurement subset, and an individual element of an intra-region utility measurement subset is referred to herein as an intra-region optimum utility measurement. Therefore, the estimated optimum utility measurement may be an intra-region utility measurement that is deemed an estimated/exact optimum value in the intra-region utility measurement subset.

The term "insulin sensitivity prediction" may refer to a data object that describes a conclusion about responsiveness of the insulin-dependent glucose-utilizing cells of a monitored end-user to absorb glucose in response to pancreatic insulin secretion and/or exogenous insulin infusion. In some embodiments, the insulin sensitivity prediction may be determined based at least in part on at least one of the maximal insulin secretion rate parameter value and the insulin secretion acceleration parameter value. In some embodiments, if the maximal insulin secretion rate parameter is higher than an expected amount, a computer system may determine that the insulin-dependent glucose-utilizing cells of the monitored end-user have developed abnormal levels of insulin sensitivity, which in turn may be used to facilitate an automated diagnosis of type-2 diabetes.

The term "beta cell capacity prediction" may refer to a data object that describes a prediction about the capacity of $\beta$-cells in pancreas to synthetize and secrete insulin. In some embodiments, a beta cell capacity prediction may be determined based on the optimized values for at least one of the noted parameters of the steady-state glucose-insulin prediction machine learning model of Equation 15 and/or the steady-state glucose-insulin prediction machine learning model of Equation 16: a, d, or n. In some embodiments, a beta cell capacity prediction may be determined based on an estimated delay factor determined using a glucose-insulin prediction model. In some embodiments, a beta cell capacity measurement may be used to determine an optimal exogenous insulin injection rate for a monitored individual.

The term "machine learning model" may refer to a data object that describes parameters and/or hyper-parameters (e.g., hyper-parameters describing defined operation types) of a model that is configured to process one or more prediction input values (e.g., one or more selected glucose concentration measurements) in accordance with one or more trained parameters of the machine learning models in order to generate a prediction. An example of a machine learning model is a mathematically derived algorithm (MDA). An MDA may comprise any algorithm trained using training data to predict one or more outcome variables. Without limitation, an MDA, as used herein, may comprise machine learning frameworks including neural networks, support vector machines, gradient boosts, Markov models, adaptive Bayesian techniques, and statistical models (e.g., timeseries-based forecast models such as autoregressive models, autoregressive moving average models, and/or an autoregressive integrating moving average models). Additionally and without limitation, an MDA, as used in the singular, may include ensembles using multiple machine learning and/or statistical techniques.

The term "glucose-insulin temporal derivative factor" may refer to a data object that describes a derivative of a glucose-insulin function with respect to time, where a glucose-insulin function is a function describing/estimating a glucose-related feature, an insulin-related feature, and/or a feature related to both glucose and insulin. Examples of glucose-insulin temporal derivative factors include a derivative of a glucose concentration function with respect to time and a derivative of an insulin concentration function with respect to time.

III. COMPUTER PROGRAM PRODUCTS, METHODS, AND COMPUTING ENTITIES

Embodiments of the present invention may be implemented in various ways, including as computer program products that comprise articles of manufacture. Such computer program products may comprise one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may comprise a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media comprise all computer-readable media (including volatile and non-volatile media).

In one embodiment, a non-volatile computer-readable storage medium may comprise a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also comprise a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also comprise read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also comprise conductive-bridging random access memory (CBRAM), phase-change random access memory (PRAM), ferroelectric random-access memory (FeRAM), non-volatile random-access memory (NVRAM), magneto-resistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may comprise random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. EXEMPLARY SYSTEM ARCHITECTURE

The architecture 100 includes a predictive data analysis computing entity 106, a glucose monitoring computing entity 101, an automated insulin delivery computing entity 102, a client computing entity 103, and one or more external computing entities 104. Communication between the noted computing entities may be facilitated using one or more communication networks. Examples of communication networks comprise any wired or wireless communication network including, for example, a wired or wireless local area network (LAN), personal area network (PAN), metropolitan area network (MAN), wide area network (WAN), short-range communication networks (e.g., Bluetooth® networks), or the like, as well as any hardware, software and/or firmware required to implement it (such as, e.g., network routers, and/or the like).

The predictive data analysis computing entity 106 may be configured to receive glucose monitoring data (e.g., CGM data) from the glucose monitoring computing entity 101, process the glucose monitoring data to determine one or more prediction-based actions, and perform the one or more prediction-based actions by interacting with at least one of the glucose monitoring computing entity 101, the automated insulin delivery computing entity 102, and the external computing entities 104.

For example, the predictive data analysis computing entity 106 may communicate glucose-insulin predictions generated based at least in part on the glucose monitoring data to the glucose monitoring computing entity 101 and/or to the external computing entities 104. As another example, the predictive data analysis computing entity 106 may, in response to determining a positive insulin need determination based at least in part on the glucose monitoring data for a monitored end-user, communicate one or more insulin delivery instructions to the automated insulin delivery computing entity 102 that is associated with the monitored end-user. In some embodiments, some or all of the functions of the predictive data analysis computing entity 106 are performed by the glucose monitoring computing entity 101. In some of the noted embodiments, the glucose monitoring computing entity 101 is configured to receive glucose monitoring data (e.g., CGM data) from the glucose monitoring computing entity 101, process the glucose monitoring data to determine one or more prediction-based actions, and perform the one or more prediction-based actions by interacting with at least one of the glucose monitoring computing entity 101, the automated insulin delivery computing entity 102, and the external computing entities 104.

The glucose monitoring computing entity 101 may be configured to record glucose concentration measurements for a monitored end-user and to communicate the glucose concentration measurements to at least one of the predictive data analysis computing entity 106, the glucose monitoring computing entity 101, and the external computing entities 104. In some embodiments, the glucose monitoring computing entity 101 is directly connected to the predictive data analysis computing entity 106. In some embodiments, the glucose monitoring computing entities 101 is configured to transmit the glucose concentration measurements to the glucose monitoring computing entity 101, and the glucose monitoring computing entity 101 is configured to forward the glucose concentration measurements received from the glucose monitoring computing entity 101 to the predictive data analysis computing entity 106.

In some embodiments, the glucose monitoring computing entity 101 includes one or more CGM sensors. Some CGM monitors use a small, disposable sensor inserted just under the skin. The sensor must be calibrated with a traditional finger-stick test and the glucose levels in the interstitial fluid may lag five or more minutes behind blood glucose levels. Other CGM monitors may use non-invasive techniques such as transmission and reflection spectroscopy. In some embodiments, the glucose monitoring computing entity 101 includes a display device that is configured to display a user interface. Such a user interface could include, for example, one or more of a display screen, an audio speaker, or a tactile output. In some embodiments, the user interface allows the user to communicate with the system. For example, in some embodiments, the system may include a keyboard, microphone, or touch screen allowing the user to enter information related to glucose levels such as the type, time, and amount of food consumed or the type, time, intensity of physical activity, medicines used and in what amount, stress level, depression level, energy level, location, or an environmental condition.

The automated insulin delivery computing entity 102 may be configured to receive insulin delivery instructions from the predictive data analysis computing entity 106 and to perform the received insulin delivery instructions by injecting/distributing insulin to the bloodstream of a monitored end-user in amounts specified by the insulin delivery instructions. In some embodiments, the automated insulin delivery computing entity 102 includes one or more insulin pumps, where an insulin pump is a computerized device that is configured to mimic the operation of the pancreas by secreting insulin amounts, as well as tubing mechanisms and an infusion set. In some embodiments, the automated insulin delivery computing entity 102 directly receives insulin delivery instructions from the predictive data analysis computing entity 106. In some embodiments, the predictive data analysis computing entity 106 transmits the insulin delivery instructions to the glucose monitoring computing entity 101, and the glucose monitoring computing entity 101 in turn forwards the insulin delivery instructions to the automated insulin delivery computing entity 102. In some embodiments, the automated insulin delivery computing entity 102 includes a display device that is configured to display a user interface. Such a user interface could include, for example, one or more of: a display screen, an audio speaker, or a tactile output. In some embodiments, the user interface allows the user to communicate with the system. For example, in some embodiments, the system may include a keyboard, microphone, or touch screen allowing the user to enter information related to glucose levels such as the type, time, and amount of food consumed or the type, time, intensity of physical activity, medicines used and in what amount, stress level, depression level, energy level, location, or an environmental condition.

The client computing entity 103 may be configured to enable user display of glucose monitoring data and/or user configuration of predictive management actions performed by the predictive data analysis computing entity 106. Examples of client computing entities 103 include smartphone devices, tablet devices, personal computer devices, and/or the like. The client computing entity 103 may include a short-range communication network receiver (e.g., a Bluetooth® receiver) that is configured to receive glucose monitoring data from the glucose monitoring computing entity 101 and/or to provide insulin delivery instructions to the automated insulin delivery computing entity 102. The client computing entity 103 may further be configured to provide glucose monitoring data received from the glucose monitoring computing entity 101 to the predictive data analysis computing entity 106 and/or to receive insulin delivery instructions from the predictive data analysis computing entity 106 before transmission of the noted insulin delivery instructions to the automated insulin delivery computing entity 102.

In some embodiments, the glucose monitoring computing entity 101 is configured to perform some or all of the functionalities of the predictive data analysis computing entity 106. In some of the noted embodiments, the predictive data analysis computing entity 106 is configured to receive glucose monitoring data (e.g., CGM data) from the glucose monitoring computing entity 101, process the glucose monitoring data to determine one or more prediction-based actions, and perform the one or more prediction-based actions by interacting with at least one of the glucose monitoring computing entity 101, the automated insulin delivery computing entity 102, and the external computing entities 104.

The external computing entities 104 may be configured to receive notification data and/or user interface data generated by the predictive data analysis computing entity 106 and perform corresponding actions based at least in part on the receive data. For example, an external computing entity 104 may be configured to generate one or more physician alerts and/or one or more healthcare provider alerts based at least in part on the notification data provided by the predictive data analysis computing entity 106. As another example, an external computing entity 104 may be configured to generate one or more automated physician appointments, automated medical notes, automated prescription recommendations, and/or the like based at least in part on the notification data received from the predictive data analysis computing entity 106. As yet another example, an external computing entity 104 may be configured to enable an end-user device associated with the external computing entity 104 to display a user interface, where the user interface may have been generated based at least in part on the user interface data provided by the predictive data analysis computing entity 106. Examples of external computing entities 104 include hospital servers, physician servers, laboratory servers, emergency room servers, urgent care centers, research institution servers, and/or the like.

Exemplary Predictive Data Analysis Computing Entity

FIG. 2 provides a schematic of a predictive data analysis computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the predictive data analysis computing entity 106 may also comprise one or more network interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the predictive data analysis computing entity 106 may comprise or be in communication with one or more processing elements 205 (also referred to as processors, processing circuitry, and/or similar terms used herein interchangeably) that communicate with other elements within the predictive data analysis computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, another circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the predictive data analysis computing entity 106 may further comprise or be in communication with non-volatile media (also referred to as non-volatile storage, memory, memory storage, memory circuitry and/or similar terms used herein interchangeably). In one embodiment, the non-volatile storage or memory may comprise one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or information/data that is stored in a computer-readable storage medium using one or more database models, such as a hierarchical database model, network model, relational model, entity-relationship model, object model, document model, semantic model, graph model, and/or the like.

In one embodiment, the predictive data analysis computing entity 106 may further comprise or be in communication with volatile media (also referred to as volatile storage, memory, memory storage, memory circuitry and/or similar terms used herein interchangeably). In one embodiment, the volatile storage or memory may also comprise one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 205 and operating system.

As indicated, in one embodiment, the predictive data analysis computing entity 106 may also comprise one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless client communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE® 802.11 (Wi-Fi), Wi-Fi Direct, 802.16 (WiMAX®), ultra-wideband (UWB), infrared (IR) protocols, near field communication (NFC) protocols, Wibree, Bluetooth® protocols, wireless universal serial bus (USB) protocols, and/or any other wireless protocol.

Although not shown, the predictive data analysis computing entity 106 may comprise or be in communication with one or more input elements, such as a keyboard input, a mouse input, a touch screen/display input, motion input, movement input, audio input, pointing device input, joystick input, keypad input, and/or the like. The predictive data analysis computing entity 106 may also comprise or be in communication with one or more output elements (not shown), such as audio output, video output, screen/display output, motion output, movement output, and/or the like.

Exemplary Glucose Monitoring Computing Entity

FIG. 3 provides an illustrative schematic representative of a glucose monitoring computing entity 101 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Glucose monitoring computing entities 101 can be operated by various parties. As shown in FIG. 3, the glucose monitoring computing entity 101 can comprise an antenna 312, a transmitter 304 (e.g., radio), a receiver 306 (e.g., radio), a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly, a power source 326, and a glucose sensor 328.

The signals provided to and received from the transmitter 304 and the receiver 306, correspondingly, may comprise signaling information/data in accordance with air interface standards of applicable wireless systems. In this regard, the glucose monitoring computing entity 101 may be capable of operating with one or more air interface standards, communication protocols, modulation types, and access types. More particularly, the glucose monitoring computing entity 101 may operate in accordance with any of a number of wireless communication standards and protocols, such as those described above with regard to the predictive data analysis computing entity 106. In a particular embodiment, the glucose monitoring computing entity 101 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX®, UWB, IR, NFC, Bluetooth®, USB, and/or the like. Similarly, the glucose monitoring computing entity 101 may operate in accordance with multiple wired communication standards and protocols, such as those described above with regard to the predictive data analysis computing entity 106 via a network interface 320.

Via these communication standards and protocols, the glucose monitoring computing entity 101 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The glucose monitoring computing entity 101 can also download changes, add-ons, and updates, for instance, to its firmware, software (e.g., including executable instructions, applications, program modules), and operating system.

According to one embodiment, the glucose monitoring computing entity 101 may comprise location determining aspects, devices, modules, functionalities, and/or similar words used herein interchangeably. For example, the glucose monitoring computing entity 101 may comprise outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This information/data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the glucose monitoring computing entity's 102 position in connection with a variety of other systems, including cellular towers, Wi-Fi access points, and/or the like. Similarly, the glucose monitoring computing entity 101 may comprise indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may comprise the iBeacons, Gimbal proximity beacons, Bluetooth® Low Energy (BLE) transmitters, NFC transmitters, and/or the like. These indoor positioning aspects can be used in a variety of settings to determine the location of someone or something to within inches or centimeters.

In some embodiments, the transmitter 304 may include one or more Bluetooth® transmitters. In some embodiments, the receiver 306 may include one or more Bluetooth® receivers. The Bluetooth® transmitters and/or the Bluetooth® receivers may be configured to communicate with at least one of the client computing entity 103 and the predictive data analysis computing entity 106. In some embodiments, the transmitter 304 may include one or more WAN transmitters. In some embodiments, the receiver 306 may include one or more WAN receivers. The WAN transmitters and/or the WAN receivers may be configured to communicate with at least one of the client computing entity 103 and the predictive data analysis computing entity 106.

The power source 326 may include electric circuitry configured to enable powering the glucose monitoring computing entity 101. The power source 326 may include one or more batteries, such as a rechargeable lithium-ion (Li-Ion) battery, that are configured to act as sources of electric power for the glucose monitoring computing entity 101.

The glucose monitoring computing entity 101 may also comprise a user interface (that can optionally comprise a display 316 coupled to a processing element 308) and/or a user input interface (coupled to a processing element 308). For example, the user interface may be a user application, browser, user interface, and/or similar words used herein interchangeably executing on and/or accessible via the glucose monitoring computing entity 101 to interact with and/or cause display of information/data from the predictive data analysis computing entity 106, as described herein. The user input interface can comprise any of a number of devices or interfaces allowing the glucose monitoring computing entity 101 to receive data, such as a keypad 318 (hard or soft), a touch display, voice/speech or motion interfaces, or other input device. In embodiments including a keypad 318, the keypad 318 can comprise (or cause display of) the conventional numeric (0-9) and related keys (#, *), and other keys used for operating the glucose monitoring computing entity 101 and may comprise a full set of alphabetic keys or set of keys that may be activated to provide a full set of alphanumeric keys. In addition to providing input, the user input interface can be used, for example, to activate or deactivate certain functions, such as screen savers and/or sleep modes.

The glucose monitoring computing entity 101 can also comprise volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the glucose monitoring computing entity 101. As indicated, this may comprise a user application that is resident on the entity or accessible through a browser or other user interface for communicating with the predictive data analysis computing entity 106 and/or various other computing entities.

In another embodiment, the glucose monitoring computing entity 101 may comprise one or more components or functionalities that are the same or similar to those of the predictive data analysis computing entity 106, as described in greater detail above. As will be recognized, these architectures and descriptions are provided for exemplary purposes only and are not limiting to the various embodiments.

Exemplary Automated Insulin Delivery Computing Entity

FIG. 4 provides an illustrative schematic representative of an automated insulin delivery computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Automated insulin delivery computing entities 102 can be operated by various parties. As shown in FIG. 4, the automated insulin delivery computing entity 102 can comprise an antenna 412, a transmitter 404 (e.g., radio), a receiver 406 (e.g., radio), a processing element 408 (e.g., CPLDs, microprocessors, multi-core processors, coprocessing entities, ASIPs, microcontrollers, and/or controllers) that provides signals to and receives signals from the transmitter 404 and receiver 406, correspondingly, a power source 426, an insulin pump 428, an insulin delivery mechanism 430, and a glucose sensor 432.

The signals provided to and received from the transmitter 404 and the receiver 406, correspondingly, may comprise signaling information/data in accordance with air interface standards of applicable wireless systems. In this regard, the automated insulin delivery computing entity 102 may be capable of operating with one or more air interface standards, communication protocols, modulation types, and access types. More particularly, the automated insulin delivery computing entity 102 may operate in accordance with any of a number of wireless communication standards and protocols, such as those described above with regard to the predictive data analysis computing entity 106. In a particular embodiment, the automated insulin delivery computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX®, UWB, IR, NFC, Bluetooth®, USB, and/or the like. Similarly, the automated insulin delivery computing entity 102 may operate in accordance with multiple wired communication standards and protocols, such as those described above with regard to the predictive data analysis computing entity 106 via a network interface 420.

Via these communication standards and protocols, the automated insulin delivery computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The automated insulin delivery computing entity 102 can also download changes, add-ons, and updates, for instance, to its firmware, software (e.g., including executable instructions, applications, program modules), and operating system.

According to one embodiment, the automated insulin delivery computing entity 102 may comprise location determining aspects, devices, modules, functionalities, and/or similar words used herein interchangeably. For example, the automated insulin delivery computing entity 102 may comprise outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This information/data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the automated insulin delivery computing entity's 102 position in connection with a variety of other systems, including cellular towers, Wi-Fi access points, and/or the like. Similarly, the automated insulin delivery computing entity 102 may comprise indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may comprise the iBeacons, Gimbal proximity beacons, Bluetooth® Low Energy (BLE) transmitters, NFC transmitters, and/or the like. These indoor positioning aspects can be used in a variety of settings to determine the location of someone or something to within inches or centimeters.

In some embodiments, the transmitter 404 may include one or more Bluetooth® transmitters. In some embodiments, the receiver 406 may include one or more Bluetooth® receivers. The Bluetooth® transmitters and/or the Bluetooth® receivers may be configured to communicate with at least one of the client computing entity 103 and the predictive data analysis computing entity 106. In some embodiments, the transmitter 404 may include one or more WAN transmitters. In some embodiments, the receiver 406 may include one or more WAN receivers. The WAN transmitters and/or the WAN receivers may be configured to communicate with at least one of the client computing entity 103 and the predictive data analysis computing entity 106.

The power source 426 may include electric circuitry configured to enable powering the automated insulin delivery computing entity 102. The power source 426 may include one or more batteries, such as a rechargeable lithium-ion (Li-Ion) battery, that are configured to act as sources of electric power for the automated insulin delivery computing entity 102.

The automated insulin delivery computing entity 102 may also optionally comprise a user interface (that can comprise a display 416 coupled to a processing element 408) and/or a user input interface (coupled to a processing element 408). For example, the user interface may be a user application, browser, user interface, and/or similar words used herein interchangeably executing on and/or accessible via the automated insulin delivery computing entity 102 to interact with and/or cause display of information/data from the predictive data analysis computing entity 106, as described herein. The user input interface can comprise any of a number of devices or interfaces allowing the automated insulin delivery computing entity 102 to receive data, such as a keypad 418 (hard or soft), a touch display, voice/speech or motion interfaces, or other input device. In embodiments including a keypad 418, the keypad 418 can comprise (or cause display of) the conventional numeric (0-9) and related keys (#, *), and other keys used for operating the automated insulin delivery computing entity 102 and may comprise a full set of alphabetic keys or set of keys that may be activated to provide a full set of alphanumeric keys. In addition to providing input, the user input interface can be used, for example, to activate or deactivate certain functions, such as screen savers and/or sleep modes.

The automated insulin delivery computing entity 102 can also comprise volatile storage or memory 422 and/or non-volatile storage or memory 424, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the automated insulin delivery computing entity 102. As indicated, this may comprise a user application that is resident on the entity or accessible through a browser or other user interface for communicating with the predictive data analysis computing entity 106 and/or various other computing entities.

In another embodiment, the automated insulin delivery computing entity 102 may comprise one or more components or functionality that are the same or similar to those of the predictive data analysis computing entity 106, as described in greater detail above. As will be recognized, these architectures and descriptions are provided for exemplary purposes only and are not limiting to the various embodiments.

Exemplary Client Computing Entity

FIG. 5 provides an illustrative schematic representative of a client computing entity 103 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Client computing entities 103 can be operated by various parties. As shown in FIG. 5, the client computing entity 103 can comprise an antenna 512, a transmitter 504 (e.g., radio), a receiver 506 (e.g., radio), a processing element 508 (e.g., CPLDs, microprocessors, multi-core processors, coprocessing entities, ASIPs, microcontrollers, and/or controllers) that provides signals to and receives signals from the transmitter 504 and receiver 506, correspondingly, a glucose sensor 528, and a power source 526.

The signals provided to and received from the transmitter 504 and the receiver 506, correspondingly, may comprise signaling information/data in accordance with air interface standards of applicable wireless systems. In this regard, the client computing entity 103 may be capable of operating with one or more air interface standards, communication protocols, modulation types, and access types. More particularly, the client computing entity 103 may operate in accordance with any number of wireless communication standards and protocols, such as those described above with regard to the predictive data analysis computing entity 106. In a particular embodiment, the client computing entity 103 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX®, UWB, IR, NFC, Bluetooth®, USB, and/or the like. Similarly, the client computing entity 103 may operate in accordance with multiple wired communication standards and protocols, such as those described above with regard to the predictive data analysis computing entity 106 via a network interface 520.

Via these communication standards and protocols, the client computing entity 103 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The client computing entity 103 can also download changes, add-ons, and updates, for instance, to its firmware, software (e.g., including executable instructions, applications, program modules), and operating system.

According to one embodiment, the client computing entity 103 may comprise location determining aspects, devices, modules, functionalities, and/or similar words used herein interchangeably. For example, the client computing entity 103 may comprise outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This information/data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the glucose monitoring computing entity's 102 position in connection with a variety of other systems, including cellular towers, Wi-Fi access points, and/or the like. Similarly, the client computing entity 103 may comprise indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may comprise the iBeacons, Gimbal proximity beacons, Bluetooth® Low Energy (BLE) transmitters, NFC transmitters, and/or the like. These indoor positioning aspects can be used in a variety of settings to determine the location of someone or something to within inches or centimeters.

In some embodiments, the transmitter 504 may include one or more Bluetooth® transmitters. In some embodiments, the receiver 506 may include one or more Bluetooth® receivers. The Bluetooth® transmitters and/or the Bluetooth® receivers may be configured to communicate with at least one of the glucose monitoring computing entity 101 and the automated insulin delivery computing entity 102. In some embodiments, the transmitter 504 may include one or more WAN transmitters. In some embodiments, the receiver 506 may include one or more WAN receivers. The WAN transmitters and/or the WAN receivers may be configured to communicate with the predictive data analysis computing entity 106.

The power source 526 may include electric circuitry configured to enable powering the client computing entity 103. The power source 526 may include one or more batteries, such as a nickel metal-hydride (NiMH) battery, that are configured to act as sources of electric power for the client computing entity 103.

The client computing entity 103 may also comprise a user interface (that can comprise a display 516 coupled to a processing element 508) and/or a user input interface (coupled to a processing element 508). For example, the user interface may be a user application, browser, user interface, and/or similar words used herein interchangeably executing on and/or accessible via the client computing entity 103 to interact with and/or cause display of information/data from the predictive data analysis computing entity 106, as described herein. The user input interface can comprise any of a number of devices or interfaces allowing the client computing entity 103 to receive data, such as a keypad 518 (hard or soft), a touch display, voice/speech or motion interfaces, or other input device. In embodiments including a keypad 518, the keypad 518 can comprise (or cause display of) the conventional numeric (0-9) and related keys (#, *), and other keys used for operating the client computing entity 103 and may comprise a full set of alphabetic keys or set of keys that may be activated to provide a full set of alphanumeric keys. In addition to providing input, the user input interface can be used, for example, to activate or deactivate certain functions, such as screen savers and/or sleep modes.

The client computing entity 103 can also comprise volatile storage or memory 522 and/or non-volatile storage or memory 524, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the client computing entity 103. As indicated, this may comprise a user application that is resident on the entity or accessible through a browser or other user interface for communicating with the predictive data analysis computing entity 106 and/or various other computing entities.

In another embodiment, the client computing entity 103 may comprise one or more components or functionalities that are the same or similar to those of the predictive data analysis computing entity 106, as described in greater detail above. As will be recognized, these architectures and descriptions are provided for exemplary purposes only and are not limiting to the various embodiments.

Exemplary External Computing Entity

FIG. 6 provides a schematic of an external computing entity 104 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the predictive data analysis computing entity 106 may also comprise one or more network interfaces 620 for communicating with various computing entities, such as by communicating data, content, information, and/or similar terms used herein interchangeably that can be transmitted, received, operated on, processed, displayed, stored, and/or the like.

As shown in FIG. 6, in one embodiment, the external computing entity 104 may comprise or be in communication with one or more processing elements 605 (also referred to as processors, processing circuitry, and/or similar terms used herein interchangeably) that communicate with other elements within the external computing entity 104 via a bus, for example. As will be understood, the processing element 605 may be embodied in a number of different ways.

For example, the processing element 605 may be embodied as one or more complex programmable logic devices (CPLDs), microprocessors, multi-core processors, coprocessing entities, application-specific instruction-set processors (ASIPs), microcontrollers, and/or controllers. Further, the processing element 605 may be embodied as one or more other processing devices or circuitry. The term circuitry may refer to an entirely hardware embodiment or a combination of hardware and computer program products. Thus, the processing element 605 may be embodied as integrated circuits, application specific integrated circuits (ASICs), field programmable gate arrays (FPGAs), programmable logic arrays (PLAs), hardware accelerators, another circuitry, and/or the like.

As will therefore be understood, the processing element 605 may be configured for a particular use or configured to execute instructions stored in volatile or non-volatile media or otherwise accessible to the processing element 205. As such, whether configured by hardware or computer program products, or by a combination thereof, the processing element 605 may be capable of performing steps or operations according to embodiments of the present invention when configured accordingly.

In one embodiment, the external computing entity 104 may further comprise or be in communication with non-volatile media (also referred to as non-volatile storage, memory, memory storage, memory circuitry and/or similar terms used herein interchangeably). In one embodiment, the non-volatile storage or memory may comprise one or more non-volatile storage or memory media 610, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or information/data that is stored in a computer-readable storage medium using one or more database models, such as a hierarchical database model, network model, relational model, entity-relationship model, object model, document model, semantic model, graph model, and/or the like.

In one embodiment, the external computing entity 104 may further comprise or be in communication with volatile media (also referred to as volatile storage, memory, memory storage, memory circuitry and/or similar terms used herein interchangeably). In one embodiment, the volatile storage or memory may also comprise one or more volatile storage or memory media 615, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 605 and operating system.

As indicated, in one embodiment, the external computing entity 104 may also comprise one or more network interfaces 620 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless client communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE® 802.11 (Wi-Fi), Wi-Fi Direct, 802.16 (WiMAX®), ultra-wideband (UWB), infrared (IR) protocols, near field communication (NFC) protocols, Wibree, Bluetooth® protocols, wireless universal serial bus (USB) protocols, and/or any other wireless protocol.

Although not shown, the predictive data analysis computing entity 106 may comprise or be in communication with one or more input elements, such as a keyboard input, a mouse input, a touch screen/display input, motion input, movement input, audio input, pointing device input, joystick input, keypad input, and/or the like. The predictive data analysis computing entity 106 may also comprise or be in communication with one or more output elements (not shown), such as audio output, video output, screen/display output, motion output, movement output, and/or the like.

V. EXEMPLARY SYSTEM OPERATIONS

This section describes, inter alia, four sets of concepts: glucose surge excursion detection concepts, glucose-insulin prediction machine learning concepts, parameter optimization concepts, and predictive glucose-insulin management concepts. While various embodiments of the present invention discuss the noted four sets of concepts as connected to each other, a person of ordinary skill in the relevant technology will recognize that any one or more of the noted four sets of concepts can be implemented without the others. For example, the glucose surge excursion detection concepts may be implemented without the parameter optimization concepts and the predictive glucose-insulin management concepts. As yet another example, the parameter optimization concepts may be implemented to optimize parameters of machine learning models other than the glucose-insulin prediction machine learning models discussed herein.

FIG. 7 is a flowchart diagram of an example process 700 for performing predictive monitoring of the glucose-insulin endocrine metabolic regulatory system of a corresponding monitored end-user. Via the various steps/operations of the process 700, the predictive data analysis computing entity 106 can perform predictive glucose-insulin monitoring using glucose monitoring data alone, which in turn increases the network transmission efficiency of performing glucose-insulin monitoring in a distributed manner by reducing the need for transmission of non-glucose-monitoring data to the predictive data analysis computing entity 106 in order to enable performing distributed glucose-insulin monitoring.

A. Glucose Surge Excursion Detection

The process 700 begins at step/operation 701 when the predictive data analysis computing entity 106 detects a glucose surge excursion based at least in part on the glucose monitoring data. In some embodiments, to determine a glucose surge excursion, the predictive data analysis computing entity 106 analyzes the glucose concentration measurements described by the glucose monitoring data to identify continuous subsets of the noted glucose concentration measurements that collectively describe a period of heightened glucose concentrations. In some embodiments, to determine a glucose surge excursion, the predictive data analysis computing entity 106 utilizes data that describe that the monitored end-user has engaged in activities that are likely to induce heightened glucose concentrations through exogenous glucose infusion into the bloodstream of the monitored end-user. Examples of such excursion-inducing activities include meal ingestion, oral glucose consumption, continuous enteral nutrition, and constant glucose infusion.

In some embodiments, the glucose surge excursion determined at step/operation 701 describes a period of time that is associated with one or more heightened periods of glucose concentration for a corresponding monitored end-user. For example, the glucose surge excursion may describe a period of time that is estimated to include a period of exogenous glucose infusion, such as exogenous glucose infusion through at least one of meal ingestion, oral glucose consumption, continuous enteral nutrition, and constant glucose infusion. As another example, the glucose surge excursion may describe a period of time that is estimated to include a period of hepatic glucose production. As another example, the glucose surge excursion may describe a period of time that is estimated to include both a period of exogenous glucose infusion and a period of hepatic glucose production. As yet another example, the glucose surge excursion may describe a period of heightened glucose concentration for the corresponding monitored end-user, regardless of the source of the noted heightened glucose concentration.

In some embodiments, the glucose monitoring data utilized at step/operation 701 one or more glucose concentration measurements for a corresponding monitored end-user, where each glucose concentration measurement is associated with a corresponding point in time that is associated with the noted glucose concentration measurement. The glucose monitoring data may be calculated using one or more glucose sensors, where the glucose sensors are configured to record glucose concentration measurements and to transmit (e.g., wirelessly, through a wired transmission medium, and/or the like) the recorded glucose concentration measurements to a computing device configured to store glucose concentration measurements. Examples of glucose sensors may include glucose sensors that are in direct contact with at least one of interstitial fluids, blood, other bodily fluids as well as glucose sensors that are not in direct contact with any of the interstitial fluids, blood, other bodily fluids, or tissues, where the latter category may include glucose sensors that use transmission spectroscopy and glucose sensors that use reflection spectroscopy.

In some embodiments, the glucose monitoring data are generated by using one or more glucose sensors that collectively enable CGM for the corresponding monitored end-user. In some embodiments, GGM is a process that is configured to record glucose concentration measurements for a corresponding monitored end-user with a continuous frequency and/or with a quasi-continuous frequency, where recording glucose concentration measurements with quasi-continuous frequency may include recording glucose concentration measurements with a frequency deemed sufficiently high to enable measurement of glucose concentrations with an estimated degree of reliability that is deemed to be equivalent to the estimated degree of reliability of measurement of glucose concentrations with continuous frequency. Accordingly, it is important to note that CGM does not require that readings be instantaneous or absolutely continuous. In some embodiments, CGM devices provide glucose concentration measurements every five to ten minutes. This frequency may be driven by the need for fidelity of control and by the fact that the most patient-friendly place to sample blood is in the periphery and peripheral blood measurements lag portal measurement, as taking samples over five minutes may reduce the probability that no single abnormal reading will cause incorrect insulin dosing. In some embodiments, in microdialysis-based CGM, sensors may measure glucose in interstitial fluid, where the glucose levels in the interstitial fluid may lag five or more minutes behind blood glucose levels.

In some embodiments, step/operation 701 may be performed based at least in part on CGM data in accordance with the process 701A depicted in FIG. 8. The process 701A depicted in FIG. 8 begins at step/operation 801 when the predictive data analysis computing entity 106 identifies a plurality of temporal units associated with the CGM data. The plurality of temporal units may correspond to discretized units of time, where each discretized unit of time may be associated with one or more corresponding glucose concentration measurements. For example, if the CGM data includes continuous recordings of glucose concentration measurements, the plurality of temporal units may be determined by subdividing the temporal range of the continuous range into one or more temporal subranges (e.g., one or more temporal subranges of equal magnitude, such as one or more minute-long temporal subranges). As another example, if the CGM data include quasi-continuous recordings of glucose concentration measurements (e.g., one glucose concentration measurement for every five minutes of a monitoring time interval), each temporal subrange may correspond to n periodic glucose concentration measurements (e.g., where the value of n may be one).

At step/operation 802, the predictive data analysis computing entity 106 determines an excursion initiation probability for each temporal unit of the plurality of temporal units. The excursion initiation probability may describe an estimated likelihood that a corresponding temporal unit is the beginning point of a glucose surge excursion. The excursion initiation probability for a corresponding temporal unit may be determined based at least in part on at least one of statistical distribution properties of the glucose concentration measurement associated with the temporal unit and a user-supplied meal session initiation indicator for the temporal unit. For example, the excursion initiation probability for a corresponding temporal unit may increase if a neighboring CGM moving average for the temporal unit exceeds a neighboring CGM moving average threshold. As another example, the excursion initiation probability for a corresponding temporal unit may increase if a CGM first derivative approximation for the temporal unit exceeds a CGM first derivative approximation threshold. As yet another example, the excursion initiation probability for a corresponding temporal unit may increase if a CGM z-score for the temporal unit exceeds a CGM z-score threshold. As a further example, the excursion initiation probability for a corresponding temporal unit may increase if the user-supplied meal session initiation indicator for the temporal unit describes that the temporal unit is associated with initiation of a meal ingestion session.

In some embodiments, the user-supplied meal session initiation indicator for a corresponding temporal unit describes whether the temporal unit is associated with a user-initiated action (e.g., pressing of a button on the client computing entity 103, opening of a meal container with strategically-positioned touch-based sensors that trigger transmission of events to the client computing entity 103 when the meal container has been opened, and/or the like) by the monitored end-user, where the user-initiated action describes whether the monitored end-user has engaged in a physical activity that is likely to lead to heightened glucose concentrations. In some embodiments, the user-supplied meal session indicator for a corresponding temporal unit describes that the monitored end-user has engaged in a physical activity that is likely to lead to heightened glucose concentrations if the timestamp of the recorded physical activity is within a delay interval of the corresponding temporal unit. In some embodiments, the delay interval may be calculated based at least in part on an at least one of a recorded consumption time, a default consumption time (e.g., an experimentally-determined average consumption time for an individual), and the glucose concentration peak interval for the monitored individual.

In some embodiments, determining an excursion initiation probability for a corresponding temporal unit is determined based at least in part on at least one of (e.g., based at least in part on all of): (i) whether a neighboring CGM moving average for the temporal unit exceeds a neighboring CGM moving average threshold, (ii) whether a CGM first derivative approximation for the temporal unit exceeds a CGM first derivative approximation threshold, or (iii) whether a CGM z-score for the temporal unit exceeds a CGM z-score threshold. In some embodiments, the neighboring CGM moving average threshold is around (e.g., is equal to) 130 milligrams per deciliter. In some embodiments, the CGM first derivative approximation threshold is around (e.g., is equal to) 2.5 milligrams per deciliter per minute. In some embodiments, the CGM z-score threshold is around (e.g., is equal to) 1.0. In some embodiments, the neighboring CGM moving average for a temporal unit is determined based at least in part on the CGM measurements of the temporal unit and six temporal units preceding the temporal unit.

In some embodiments, the excursion initiation probability for a temporal unit of the plurality of temporal units is determined by providing CGM measurements associated with the temporal unit to an excursion initiation detection machine learning model. The excursion initiation detection machine learning model may be a machine learning model that is configured to process the CGM measurements associated with a corresponding temporal unit to generate the excursion initiation probability for the corresponding temporal unit. In some embodiments, the excursion initiation detection machine learning model is trained using ground-truth data determined based at least in part on user-supplied meal session initiation indicators. An example of an excursion initiation detection machine learning model is a neural network model.

At step/operation 803, the predictive data analysis computing entity 106 determines an excursion start time from the plurality of temporal units based at least in part on each excursion initiation probability for a temporal unit of the plurality of temporal units. In some embodiments, the predictive data analysis computing entity 106 selects the temporal unit having the largest excursion initiation probability as the excursion start time. In some embodiments, the predictive data analysis computing entity 106 selects the earliest temporal unit whose excursion initiation probability exceeds an excursion initiation probability threshold as the excursion start time. In some of the noted embodiments, the excursion initiation probability threshold may be determined based at least in part on a measure of statistical distribution of the excursion initiation probabilities determined at step/operation 802, such as based at least in part on a mean, a weighted mean, a median, and/or the like of the excursion initiation probabilities determined at step/operation 802.

In some embodiments, to select the excursion start time, the predictive data analysis computing entity 106 adjusts the excursion initiation probability for the temporal unit (e.g., the excursion initiation probability determined based at least in part on at least one of the statistical distribution properties of the glucose concentration measurement associated with the temporal unit and a user-supplied meal session initiation indicator for the temporal unit) by an adjustment factor that rewards precedence of the temporal unit in an ordering of the plurality of temporal units and penalizes latency of the temporal unit in the ordering of the plurality of temporal units. The goal of this order-based adjustment operation may be to capture larger glucose surge excursions which begin at earlier points. In some of the noted embodiments, subsequent to generating order-adjusted excursion initiation probabilities for the plurality of temporal units, the predictive data analysis computing entity 106 selects the temporal unit having the largest order-adjusted excursion initiation probability as the excursion start time.

At step/operation 804, the predictive data analysis computing entity 106 determines an excursion termination probability for each temporal unit of the plurality of temporal units that occur after a predefined time interval following the excursion start time. In some embodiments, the predefined time interval is determined based at least in part on an experimentally-established minimum time interval for a glucose surge excursion and/or based at least in part on a lower-bound of the time that it may take a healthy individual to perform insulin secretion and glucose utilization after the first appearance of heightened glucose concentration in the bloodstream of the noted healthy individual.

In some embodiments, an excursion termination probability may describe an estimated likelihood that a corresponding temporal unit is the end point of a glucose surge excursion. The excursion termination probability for a corresponding temporal unit may be determined based at least in part on at least one of statistical distributional properties of the glucose concentration measurement associated with the temporal unit and a user-supplied meal session termination indicator for the temporal unit. For example, the excursion termination probability for a corresponding temporal unit may increase if a neighboring CGM moving average for the temporal unit fails to exceed a neighboring CGM moving average threshold. As another example, the excursion termination probability for a corresponding temporal unit may increase if a CGM first derivative approximation for the temporal unit fails to exceed a CGM first derivative approximation threshold. As yet another example, the excursion termination probability for a corresponding temporal unit may increase if a CGM z-score for the temporal unit fails to exceed a CGM z-score threshold. As a further example, the excursion termination probability for a corresponding temporal unit may increase if the user-supplied meal session termination indicator for the temporal unit describes that the temporal unit is associated with termination of a meal ingestion session.

In some embodiments, the user-supplied meal session termination indicator may describe whether a corresponding temporal unit is associated with a user-initiated action (e.g., pressing of a button on a client computing entity, opening of a meal container with strategically-positioned touch-based sensors that trigger transmission of events to the client computing entity 103 when the meal container has been opened, and/or the like) by a corresponding monitored end-user, where the user-initiated action describes whether the monitored end-user has engaged in a physical activity that is likely to lead to heightened glucose concentrations. In some embodiments, the user-supplied meal session initiation indicator for a corresponding temporal unit describes that the monitored end-user has engaged in a physical activity that is likely to lead to heightened glucose concentrations if the timestamp of the recorded physical activity is within a delay interval of the corresponding temporal unit. In some embodiments, the delay interval may be calculated based at least in part on an at least one of a recorded consumption time, a default consumption time (e.g., an experimentally-determined average consumption time for an individual), and the glucose concentration peak interval for the monitored individual.

In some embodiments, determining an excursion termination probability for a corresponding temporal unit is determined based at least in part on at least one of (e.g., based at least in part on all of): (i) whether a neighboring CGM moving average for the temporal unit fails to exceed a neighboring CGM moving average threshold, (ii) whether a CGM first derivative approximation for the temporal unit fails to exceed a CGM first derivative approximation threshold, or (iii) whether a CGM z-score for the temporal unit fails to exceed a CGM z-score threshold. In some embodiments, the neighboring CGM moving average threshold is around (e.g., is equal to) 130 milligrams per deciliter. In some embodiments, the CGM first derivative approximation threshold is around (e.g., is equal to) 2.5 milligrams per deciliter per minute. In some embodiments, the CGM z-score threshold is around (e.g., is equal to) 1.0. In some embodiments, the neighboring CGM moving average for a temporal unit is determined based at least in part on the CGM measurements of the temporal unit and six temporal units preceding the temporal unit.

In some embodiments, the excursion termination probability for a temporal unit of the plurality of temporal units is determined by providing CGM measurements associated with the temporal unit to an excursion termination detection machine learning model. The excursion termination detection machine learning model may be a machine learning model that is configured to process the CGM measurements associated with a corresponding temporal unit to generate the excursion termination probability for the corresponding temporal unit. In some embodiments, the excursion termination detection machine learning model is trained using ground-truth data determined based at least in part on user-supplied meal session termination indicators provided by the monitored end-user. An example of an excursion termination detection machine learning model is a neural network model.

At step/operation 805, the predictive data analysis computing entity 106 determines an excursion end time based at least in part on each excursion termination probability for a temporal unit in the selected subset. In some embodiments, the predictive data analysis computing entity 106 determines the temporal unit in the selected subset that has the highest excursion termination probability as the excursion end time.

In some embodiments, the predictive data analysis computing entity 106 first determines one or more potential excursion end times of the of plurality of temporal units in the selected subset (i.e., the selected subset of the plurality of temporal units that occur after a predefined time interval following the excursion start time) based at least in part on each excursion termination probability for a temporal unit in the selected subset. Afterward, the predictive data analysis computing entity 106 determines an excursion probability for each potential excursion end time of the one or more potential excursion end times. Next, the predictive data analysis computing entity 106 determines the excursion end time as the potential excursion end time having the highest excursion probability.

In some embodiments, to determine the potential excursion end times, the predictive data analysis computing entity 106 selects n temporal units in the selected subset that have the largest excursion termination probabilities as the potential excursion end times, where the value of n may be determined based at least in part on a count of the temporal units that fall within the selected subset of the plurality of temporal units that occur after a predefined time interval following the excursion start time. In some embodiments, the predictive data analysis computing entity 106 selects the latest temporal unit in the selected subset whose excursion termination probability exceeds an excursion termination probability threshold as the excursion start time. In some of the noted embodiments, the excursion termination probability threshold may be determined based at least in part on a measure of statistical distribution of the excursion termination probabilities determined at step/operation 804, such as based at least in part on a mean, a weighted mean, a median, and/or the like of the excursion termination probabilities determined at step/operation 804.

In some embodiments, to determine the potential excursion end times, the predictive data analysis computing entity 106 adjusts each excursion termination probability for a temporal unit in the selected subset (e.g., the excursion termination probability determined based at least in part on at least one of the statistical distribution properties of the glucose concentration measurement associated with the temporal unit in the selected subset and a user-supplied meal session termination indicator for the temporal unit in the selected subset) by an adjustment factor that rewards latency of the temporal unit in an ordering of the plurality of temporal units in the selected subset and penalizes precedence of the temporal unit in the ordering of the plurality of temporal units in the selected subset. The goal of this order-based adjustment operation may be to capture larger glucose surge excursions which end at later points. In some of the noted embodiments, subsequent to generating order-adjusted excursion termination probabilities for the plurality of temporal units in the selected subset, the predictive data analysis computing entity 106 selects n temporal units having the largest order-adjusted excursion termination probabilities as the excursion end-times.

In some embodiments, the predictive data analysis computing entity 106 determines an excursion probability for each potential excursion end time of the plurality of excursion end times. The excursion probability for a potential excursion end time may describe an estimated likelihood that the interval between a given excursion start time and the potential excursion end time corresponds to a glucose surge excursion. In some embodiments, the excursion probability for a potential excursion end time is determined based at least in part on a measure of temporal deviation between the given excursion start time and the potential excursion end time. For example, if the temporal measure of deviation between the glucose concentration measurement for the given excursion start time and the glucose concentration measurement for the potential excursion end time exceeds a threshold temporal measure of deviation (e.g., an experimentally-established threshold measure of temporal deviation that is configured to reflect a maximum expected time interval of a glucose surge excursion), the excursion probability for the potential excursion end time may be reduced or be set to zero.

In some embodiments, the excursion probability for a potential excursion end time is determined based at least in part on whether the glucose concentration measurements whose respective temporal units fall within the temporal interval bounded by the excursion start time and the potential excursion end time include a minimum point of the glucose concentration measurements for the plurality of temporal units and/or a maximal point of the glucose concentration measurements for the plurality of temporal units. For example, if the glucose concentration measurements whose respective temporal units fall within the temporal interval bounded by the excursion start time and the potential excursion end time include a minimum point of the glucose concentration measurements for the plurality of temporal units and/or a maximal point of the glucose concentration measurements for the plurality of temporal units, the excursion probability for the potential excursion end time may be increased accordingly.

At step/operation 806, the predictive data analysis computing entity 106 detects the glucose surge excursion based at least in part on the excursion start time and the excursion end time. In some embodiments, the predictive data analysis computing entity 106 adopts a time interval in between and excluding the excursion start time and the excursion end time as the glucose surge excursion. In some embodiments, the predictive data analysis computing entity 106 adopts a time interval between and excluding the excursion start time and the excursion end time as the glucose surge excursion.

Returning to FIG. 7, in some embodiments, step/operation 701 may include processing glucose concentration measurements before detecting glucose surge excursions based at least in part on the preprocessed glucose concentration measurements. Preprocessing may serve a variety of functions including but not limited to interpolation between glucose concentration measurements recorded at discrete points in time and attenuation of signal noise. Preprocessing may include applying functions such as moving averages, low-pass filters, and convolution using a kernel function.

Some embodiments identify a potential excursion start time (PEST) in the glucose signal and subsequently determine whether the PEST exhibits any criteria that would disqualify it from being an actual excursion start time. If the PEST exhibits any disqualifying characteristics, processing then identifies a subsequent PEST in the glucose readings and checks for disqualifying criteria. Similarly, some embodiments identify a potential excursion end time (PEET) in the glucose signal and subsequently determine whether the PEET exhibits any criteria that would disqualify it from being an actual excursion end time. If the PEET exhibits any disqualifying characteristics, processing then identifies a subsequent PEET in the glucose signal and checks for disqualifying criteria. After processing identifies a start time and end time for an excursion, some embodiments determine whether the excursion, as a whole, exhibits any disqualifying characteristics. If the excursion exhibits disqualifying characteristics, processing may exclude the excursion from the one or more excursions to which model parameters are adjusted and determines the next subsequent PEST in the glucose signal.

In some embodiments, glucose surge excursions are time periods during which glucose readings are indicative of a glucose challenge. Glucose challenges include any stimuli that would cause an increase in glucose levels. Examples of glucose challenges would include carbohydrate consumption, the injection of glucose or other carbohydrates into the body and internal processes such as glycogen breakdown and gluconeogenesis. There are multiple ways of identifying the start time and end time of an excursion. In some embodiments, processing may detect a PEST or start time when unaltered ("raw") or preprocessed glucose readings exceed a threshold that is greater than normal. Some embodiments may use thresholds between 50 mg/dl and 250 mg/dl. Similarly, in some embodiments, processing may detect a PEET or excursion end time when raw or preprocessed glucose readings fall below a threshold level that is within some margin of variation above a normal glucose concentration. Accordingly, some embodiments may use, by way of non-limiting example, thresholds between 50 mg/dl and 250 mg/dl. Some embodiments may include a criterion that multiple or consecutive glucose readings fall above or below a threshold before recording a start time or end time, respectively. As with criteria for start times and end times, criteria for disqualifying a potential excursion (bounded by a PEST and a PEET) may likewise comprise thresholds for raw or preprocessed glucose readings.

In some embodiments, step/operation 701 may be performed in accordance with the process 701B depicted in FIG. 13. The process 701B depicted in FIG. 13 begins at step/operation 1301 when the predictive data analysis computing entity 106 generates average glucose concentration measurements based at least in part on the glucose concentration measurements described by CGM data. In some embodiments, to generate the average glucose concentration measurements, the predictive data analysis computing entity 106 applies a moving average function to the glucose concentration measurements described by CGM data.

At step/operation 1302, the predictive data analysis computing entity 106 detects a PEST when a required number of consecutive average glucose concentration measurements exceed a first glucose concentration threshold. In some embodiments, the predictive data analysis computing entity 106 detects a PEST when three consecutive average glucose concentration measurements exceed the first glucose concentration threshold. In some embodiments, the predictive data analysis computing entity 106 detects a PEST when four consecutive average glucose concentration measurements exceed the first glucose concentration threshold. An example of the first glucose concentration threshold is 130 milligrams per deciliter.

At step/operation 1303, the predictive data analysis computing entity 106 determines whether the PEST detected in step/operation 1302 is followed by a sufficient increase in average glucose concentration measurements. In some embodiments, to determine whether the PEST detected in step/operation 1302 is followed by a sufficient increase in average glucose concentration measurements, the predictive data analysis computing entity 106 detects whether at least one of a ceiling number of (e.g., three, four, and/or the like) average glucose concentration measurements that immediately follow the average glucose concentration measurement of the PEST deviates from the average glucose concentration measurement of the PEET by a threshold deviation amount. An example of the threshold deviation amount is 30 milligrams per deciliter.

If the predictive data analysis computing entity 106 determines that the PEST detected in step/operation 1302 is not followed by a sufficient increase in average glucose concentration measurements, the predictive data analysis computing entity 106 returns to step/operation 1302 to detect a new PEST. However, the predictive data analysis computing entity 106 determines that the PEST detected in step/operation 1302 is followed by a sufficient increase in average glucose concentration measurements, the predictive data analysis computing entity 106 proceeds to step/operation 1304 to generate smoothed glucose concentration measurements by applying a smoothing function to the average glucose concentration measurements.

At step/operation 1305, the predictive data analysis computing entity 106 detects a PEET when a required number of consecutive average glucose concentration measurements fail to exceed a second glucose concentration threshold. In some embodiments, the predictive data analysis computing entity 106 detects a PEET when three of four consecutive average glucose concentration measurements fail to exceed the second glucose concentration threshold. An example of the second glucose concentration threshold is 100 milligrams per deciliter.

At step/operation 1306, the predictive data analysis computing entity 106 determines whether the second glucose concentration threshold is exceeded for a threshold length of time after the PEET. In some embodiments, to determine the second glucose concentration threshold is exceeded for the threshold length of time after the PEET, the predictive data analysis computing entity 106 analyzes the smoothed glucose concentration measurements associated with temporal units that fall within the threshold length of time after the PEET, and determines whether any of the noted analyzed smoothed second glucose concentration measurements exceed the second glucose concentration threshold. An example of the threshold length of time is four hours.

If the predictive data analysis computing entity 106 determines that the second glucose concentration threshold is exceeded for the threshold length of time after the PEET, the predictive data analysis computing entity 106 returns to step/operation 1305 to detect a new PEET. However, if the predictive data analysis computing entity 106 determines that the second glucose concentration threshold is not exceeded for the threshold length of time after the PEET, the predictive data analysis computing entity 106 proceeds to step/operation 1307 to determine whether any smoothed second glucose concentration measurements associated with temporal units that fall between the PEST and the PEET exceed the first glucose concentration threshold.

If the predictive data analysis computing entity 106 determines that at least one of the smoothed second glucose concentration measurements associated with temporal units that fall between the PEST and the PEET exceeds the first glucose concentration threshold, the predictive data analysis computing entity 106 returns to step/operation 1302 to detect a new PEST. However, if the predictive data analysis computing entity 106 determines that none of the smoothed second glucose concentration measurements associated with temporal units that fall between the PEST and the PEET exceeds the first glucose concentration threshold, the predictive data analysis computing entity 106 proceeds to step/operation 1308 to adopt the time interval between the PEST and the PEET as the glucose surge excursion. The process depicted in FIG. 13 may be performed repeatedly (i.e., continuously) and/or periodically (e.g., every five to ten minutes) using the CGM data.

Returning to FIG. 4, in some embodiments, step/operation 701 may include identifying excursion start times and/or excursion end times using derivatives or derivative approximations of the raw glucose readings. Glucose readings representing glucose concentration at discrete times do not lend themselves to true derivatives. However, some embodiments may use methods of approximating derivatives. Some methods estimate slope using the difference between sequential glucose readings and the amount of time between the readings. Some methods may fit a continuous mathematical function to glucose readings and then determine a derivative of that function. Using similar methods, second and higher order derivatives or derivative approximations may also be used to identify PEST, PEET, and/or be used in criteria that could disqualify PEST, PEET, or a potential excursion.

In some embodiments, step/operation 701 may be performed in accordance with the process 701C depicted in FIG. 14. The process 701C depicted in FIG. 14 begins at step/operation 1401 when the predictive data analysis computing entity 106 generates glucose concentration first derivative approximations (FDAs) based at least in part on the generates glucose concentration measurements described by the CGM data. In some embodiments, to generate the glucose concentration FDAs, the predictive data analysis computing entity 106 applies an FDA function to the generates glucose concentration measurements described by the CGM data. While various embodiments of the present invention are described with reference to FDAs, a person of ordinary skill in the relevant technology will recognize that derivatives of any derivative order may be used.

At step/operation 1402, the predictive data analysis computing entity 106 detects a PEST when a glucose concentration FDA exceeds a first glucose concentration FDA threshold. In some embodiments, the predictive data analysis computing entity 106 detects a PEST when a threshold number of (e.g., three or four) glucose concentration FDAs exceed the first glucose concentration FDA threshold. An example of the first glucose concentration FDA threshold is 0.3 milligrams per deciliter per minute.

At step/operation 1403, the predictive data analysis computing entity 106 determines whether a glucose concentration FDA that immediately follows the glucose concentration FDA of the PEST exceeds a second glucose concentration FDA threshold. In some embodiments, the predictive data analysis computing entity 106 determines whether a threshold number of (e.g., three or four) glucose concentration FDA that immediately follow the glucose concentration FDA of the PEST exceeds the second glucose concentration FDA threshold. An example of the second glucose concentration FDA threshold is 2.5 milligrams per deciliter per minute.

If the predictive data analysis computing entity 106 determines that the glucose concentration FDA that immediately follows the glucose concentration FDA of the PEST fails to exceed the second glucose concentration FDA threshold, the predictive data analysis computing entity 106 returns to step/operation 1402 to detect a new PEST.

However, if the predictive data analysis computing entity 106 determines that the glucose concentration FDA that immediately follows the glucose concentration FDA of the PEST exceeds the second glucose concentration FDA threshold, the predictive data analysis computing entity 106 proceeds to step/operation 1404 to detect a PEET when a glucose concentration FDA fails to exceed a third glucose concentration FDA threshold. In some embodiments, the predictive data analysis computing entity 106 proceeds to step/operation 1404 to detect a PEET when a threshold number of (e.g., three or four) glucose concentration FDAs fail to exceed the third glucose concentration FDA threshold. An example of the third glucose concentration FDA threshold is 0.15 milligrams per deciliter per minute.

At step/operation 1405, the predictive data analysis computing entity 106 determines whether glucose concentration FDAs for a threshold length of time after PEET exceed the third glucose concentration FDA threshold. In some embodiments, to determine whether glucose concentration FDAs for the threshold length of time after PEET exceed the third glucose concentration FDA threshold, the predictive data analysis computing entity 106 analyzes glucose concentration FDAs that are associated with temporal units that fall within the threshold length of time after the PEET, and determines whether the analyzed glucose concentration FDAs include at least one glucose concentration FDA that fails to exceed the third glucose concentration FDA threshold. An example of the threshold length of time is four hours.

If the predictive data analysis computing entity 106 determines that at least one glucose concentration FDA for the threshold length of time after PEET fails to exceed the third glucose concentration FDA threshold, the predictive data analysis computing entity 106 returns to step/operation 1404 to detect a new PEET. However, if the predictive data analysis computing entity 106 determines that all of the glucose concentration FDA for the threshold length of time after PEET exceed the third glucose concentration FDA threshold, the predictive data analysis computing entity 106 proceed to step/operation 1406 to determine whether all of the glucose concentration FDAs that are associated with temporal units that fall between PEST and PEET exceed a fourth glucose concentration FDA threshold. An example of the fourth glucose concentration FDA threshold is 3.0 milligrams per deciliter per minute.

If the predictive data analysis computing entity 106 determines that at least one of the glucose concentration FDAs that are associated with temporal units that fall between PEST and PEET fails to exceed the fourth glucose concentration FDA threshold, the predictive data analysis computing entity 106 returns to step/operation 1402 to adopt a new PEST. However, if the predictive data analysis computing entity 106 determines that all of the glucose concentration FDAs that are associated with temporal units that fall between PEST and PEET exceed the fourth glucose concentration FDA threshold, the predictive data analysis computing entity 106 proceeds to step/operation 1407 to adopt the time interval between the PEST and the PEET as the glucose surge excursion. The process depicted in FIG. 14 may be performed repeatedly (i.e., continuously) and/or periodically (e.g., every five to ten minutes) using the CGM data.

Returning to FIG. 4, in some embodiments, step/operation 701 may include identifying excursion start times and/or excursion end times using z-scores. z-scores (or "standard scores") refer to the number of standard deviations that separate an individual value from a mean value. z-scores may be a useful form of preprocessing because they are not influenced by the particular units of measure in which the input value is expressed.

In some embodiments, step/operation 701 may be performed in accordance with the process 701D depicted in FIG. 15. The process 701D depicted in FIG. 15 begins at step/operation 1501 when the predictive data analysis computing entity 106 generates glucose concentration z-scores. In some embodiments, to generate the glucose concentration z-scores, the predictive data analysis computing entity 106 first applies a kernelling method to the glucose concentration measurements described by the CGM data to generate transformed glucose concentration measurements. Afterward, the predictive data analysis computing entity 106 may determine the glucose concentration z-scores based at least in part on the transformed glucose concentration measurements.

In some embodiments, kernelling methods may comprise convolution. Convolution may refer to an operator describing how a first function modifies the outputs of a second function. Convolution may also refer to the process of generating the operator. In some embodiments, preprocessing may involve generating a derivative approximation of the glucose concentration signal and convolving the derivative approximation with some function giving the convolution $G^{GGGG}$ defined by $GG^{GGG}(G)=(GG*G)=\Sigma_{G=0}^{G}[GG(G) G(G-G)]$ where GG is the derivative approximation of the glucose signal, G is some function that the derivative approximation of the glucose concentration signal is to be convolved with, and G is an integer value from 0 to G for GG and from G–G to G for G.

At step/operation 1502, the predictive data analysis computing entity 106 detects a PEST when a glucose concentration z-score exceeds a first glucose concentration z-score threshold. In some embodiments, the predictive data analysis computing entity 106 detects a PEST when a threshold number of (e.g., three or four) glucose concentration z-scores exceed the first glucose concentration z-score threshold. An example of the first glucose concentration z-score threshold is 1.0.

At step/operation 1503, the predictive data analysis computing entity 106 generates filtered glucose concentration measurements. In some embodiments, to generate the filtered glucose concentration measurements, the predictive data analysis computing entity 106 applies a low-pass filter function to the glucose concentration measurements described by the CGM data.

At step/operation 1504, the predictive data analysis computing entity 106 determines a first local maximum in the filtered glucose concentration measurements that occur after PEST. In some embodiments, to determine the first local maximum in the filtered glucose concentration measurements, the predictive data analysis computing entity 106 identifies the filtered glucose concentration measurements associated with temporal units that occur after the PEST, and detects the first local maximum of those filtered glucose concentration measurements (e.g., using a gradient-descent-based local maximum detection technique).

A local maximum may be a measurement that is greater than both the immediately preceding measurement and the next subsequent measurement. Likewise, a local minimum may be a measurement that is less than both the preceding measurement and the next subsequent measurement. Some embodiments may comprise criteria involving local maxima or minima in a preprocessed glucose signal instead of or in addition to local maxima or minima in the raw glucose concentration measurement signal.

At step/operation 1505, the predictive data analysis computing entity 106 detects a PEET when a next-occurring equilibrium in the filtered glucose concentration measurements occurs after the first local maximum. In other words, the predictive data analysis computing entity 106 identifies the first equilibrium point after the first local maximum identified at step/operation 1504. An equilibrium point may indicate, by way of non-limiting example, that the readings have returned to a constant or approximately constant value. An equilibrium may occur at a single glucose concentration measurement or it be determined relative to a time period comprising multiple glucose concentration measurements. In some embodiments, an equilibrium may occur when differences between each of one or more of the glucose concentration measurements and a measure of statistical distribution (e.g., a mean, a median, a mode, and/or the like) of the glucose concentration measurements is each less than a threshold difference. In some embodiments, a point x* is an equilibrium point for the differential equation $dx/dt=f(x)$ if $f(x^*)=0$ for all G In some embodiments, an equilibrium point may be a fixed point for the difference equation $x_{k+1}=f(x_k)$ if: $f(k, x^*)=x^*$, for k of integer values of zero or greater. In some embodiments, an equilibrium point ($x_{k+1}$: $=x^*$) may satisfy if $|f(x_k)-f(x_{k+1})|\leq\varepsilon$ for some $\varepsilon>0$.

At step/operation 1506, the predictive data analysis computing entity 106 determines whether the PEET is followed by a sufficient decrease in filtered glucose concentration measurements. In some embodiments, to determine whether the PEET detected in step/operation 1504 is followed by a sufficient decrease in filtered glucose concentration measurements, the predictive data analysis computing entity 106 detects whether at least one of a ceiling number of (e.g., three, four, and/or the like) filtered glucose concentration measurements that immediately follow the filtered glucose concentration measurements of the PEET deviate from the filtered glucose concentration measurement of the PEET by a threshold deviation amount. An example of the threshold deviation amount is 7 milligrams per deciliter. In some embodiments, determining whether the PEET is followed by a sufficient decrease in filtered glucose concentration measurements includes determining whether the absolute value of a slope of a line connecting the first-occurring and last-occurring glucose readings in a first 20-minute interval immediately preceding PEET exceeds a threshold slope value.

If the predictive data analysis computing entity 106 determines that the PEET is not followed by a sufficient decrease in filtered glucose concentration measurements, the predictive data analysis computing entity 106 returns to step/operation 1504 to detect a new PEET. The predictive data analysis computing entity 106 may reset PEET to a previous time at step 1504. For example, some embodiments may reset PEET to be 5 minutes or one glucose reading earlier than the previous PEET.

However, if the predictive data analysis computing entity 106 determines that the PEET is followed by a sufficient decrease in filtered glucose concentration measurements, the predictive data analysis computing entity 106 proceeds to step/operation 1507 to determine whether there is more than one regional maximum between the PEST and the PEET. A regional maximum may be a measurement that is the greatest in a group of consecutive measurements. Likewise, a regional minimum may be a measurement that is the least in a group of consecutive measurement. Some embodiments may comprise criteria involving regional maxima or minima in a preprocessed glucose concentration measurement signal instead of or in addition to local maxima or minima in the raw glucose concentration measurement signal.

If the predictive data analysis computing entity 106 determines that there is more than one regional maximum between the PEST and the PEET, the predictive data analysis computing entity 106 returns to step/operation 1502 to detect a new PEST. However, if the predictive data analysis computing entity 106 determines that there is one regional maximum between the PEST and the PEET, the predictive data analysis computing entity 106 proceeds to step/operation 1508 to determine whether the PEET is within a threshold length of the PEST. An example of the threshold length of time is four hours.

In some embodiments, glucose surge excursions may be expected to last no more than a maximum amount of time. If glucose levels remain elevated for longer than this maximum amount of time, the elevation may be due to reasons other than a glucose challenge. Accordingly, some embodiments may comprise a criterion that certain characteristics of a glucose concentration measurement signal or preprocessed glucose concentration measurement signal exhibit certain characteristics within a maximum amount of time after the PEST in order to qualify as a glucose surge excursion. Correspondingly, in some embodiments, excursions may be expected to last longer than a minimum amount of time and these embodiments may comprise a criterion that certain characteristics of a glucose concentration measurement signal or preprocessed glucose concentration measurement signal exhibit certain characteristics at no less than a minimum amount of time after the PEST in order to qualify as a glucose surge excursion.

If the predictive data analysis computing entity 106 determines that the PEET is not within the threshold length of the PEST, the predictive data analysis computing entity 106 returns to step/operation 1502 to detect a new PEST. However, if the predictive data analysis computing entity 106 determines that the PEET is within the threshold length of the PEST, the predictive data analysis computing entity 106 proceeds to step/operation 1509 to adopt the time interval between the PEST and the PEET as the glucose surge excursion. The process depicted in FIG. 15 may be performed repeatedly (i.e., continuously) and/or periodically (e.g., every five to ten minutes) using the CGM data.

B. Steady-State Glucose-Insulin Prediction Models

At step/operation 702, the predictive data analysis computing entity 106 identifies a steady-state glucose-insulin prediction model. The steady-state glucose-insulin prediction model may be a machine learning model that is configured to relate cross-steady-state parameters for a corresponding monitored end-user to a steady-state glucose concentration measurement of the corresponding monitored end-user. Accordingly, the steady-state glucose-insulin prediction machine learning model may be utilized to generate estimated values for the cross-steady-state parameters based at least in part on the steady-state glucose concentration measurement of the corresponding monitored end-user, for example by determining a combination of estimated values for the cross-steady-state parameters that, when processed in accordance with the operations defined by the steady-state glucose-insulin prediction machine learning model, generates an inferred steady-state glucose concentration measurement that most closely aligns with the steady-state glucose concentration measurement.

An operational example of a steady-state glucose-insulin prediction machine learning model 1601 is depicted in FIG. 16. As depicted in FIG. 16, the steady-state glucose-insulin prediction machine learning model 1601 is configured to process a steady-state glucose concentration measurement 1611 (e.g., a steady-state glucose concentration measurement 1611 determined using CGM data, a steady-state glucose concentration measurement 1611 determined by performing a glucose surge excursion detection operation on glucose measurement data, a steady-state glucose concentration measurement 1611 determined by performing a glucose surge excursion detection operation on CGM data, and/or the like) in order to generate: (i) an insulin-dependent glucose uptake coefficient parameter 1621, (ii) a hepatic glucose production rate parameter 1622, (iii) an insulin degradation rate parameter 1623, (iv) a maximum insulin secretion rate parameter 1624, (v) an insulin-independent glucose uptake rate parameter 1625, (vi) a half-saturation glucose concentration parameter 1626, and (vii) an insulin secretion acceleration parameter 1627. The exemplary parameters 1621-1627 of the steady-state glucose-insulin prediction machine learning model 1601 are described throughout this document, including in the rest of the present subsection of the present section. Exemplary techniques for determining optimized values for the parameters 1621-1627 based at least in part on the steady-state glucose concentration measurement 1611 are described in subsection C of the present section.

In some embodiments, the steady-state glucose-insulin prediction machine learning model is generated by removing glucose-insulin temporal derivative factors and an exogenous glucose infusion rate factor from a glucose-biased glucose-insulin prediction machine learning model. In some of the noted embodiments, the noted glucose-biased glucose-insulin prediction machine learning model is generated by substituting insulin-related factors with glucose-related factors in a hybrid glucose-insulin prediction machine learning model. In some embodiments, the hybrid glucose-insulin prediction machine learning model is configured to estimate insulin secretion magnitude using a delayed Hill model, the delayed Hill model is associated with a Hill coefficient parameter, and an insulin secretion acceleration parameter value of the steady-state glucose-insulin prediction machine learning model is determined based at least in part on the noted Hill coefficient parameter.

The hybrid glucose-insulin prediction machine learning model may be a machine learning model that is configured to relate a group of glucose-concentration-related measurements and a group of insulin-concentration-related measurements for a corresponding monitored end-user to desired parameters that describe functional properties of the glucose-insulin endocrine metabolic regulatory system of the corresponding monitored end-user. For example, the glucose-biased glucose-insulin prediction machine learning model may describe a machine learning model that is configured to relate a derivative of glucose concentration function with respect to time that is evaluated at a current time to the following: (i) a current glucose concentration; (ii) a current exogenous glucose infusion rate; (iii) a hepatic glucose production rate parameter; (iv) an insulin-independent glucose uptake coefficient parameter; and (v) a current plasma insulin concentration. As another example, the glucose-biased glucose-insulin prediction machine learning model may describe a machine learning model that is configured to relate a derivative of plasma insulin concentration function with respect to time that is evaluated at a current time to the following: (i) a delayed glucose concentration; (ii) a current plasma insulin concentration; (iii) an insulin degradation rate parameter; (iv) a maximal insulin secretion rate parameter; (v) a half-saturation glucose concentration parameter value; and (vi) an insulin secretion acceleration parameter value. As yet another example, the glucose-biased glucose-insulin prediction machine learning model may describe a machine learning model that is configured to relate a current exogenous glucose infusion rate to the following: (i) a time parameter describing the current time; (ii) a measure of glucose magnitude (e.g., in milligrams) following initiation of an activity that leads to exogenous glucose infusion (e.g., consumption of a meal); (iii) plasma glucose distribution volume (e.g., in deciliters); and (iv) a glucose concentration peak interval parameter, where (ii)-(iv) may be predefined values.

In some embodiments, the general form of a hybrid glucose-insulin prediction machine learning model is described by the combination of the below Equations 1-2, which are described below with reference to the processes 900-1000 of the contextual flow diagrams of FIGS. 9-10.

$$G'(t) = G_{in}(t) - f_2(G(t)) - f_{3,4}(G(t), I(t-\tau_3)) + f_5(I(t-\tau_2)) \quad \text{Equation 1}$$

$$I'(t) = I_{in}(t) + f_1(G(t-\tau_1)) - r(I(t)) \quad \text{Equation 2}$$

As depicted in FIG. 9, the process 900 includes receiving the output value $G_{in}$ (t) at step/operation 901. The $G_{in}(x)$ function is configured to return the exogenous glucose infusion rate at a time x. Accordingly, the output value $G_{in}$ (t) is the (actual or estimated) exogenous glucose infusion rate at a current time t. The $G_{in}$ (t) may be expressed using the mass concentration/time unit, the molar concentration/time unit, or an equivalent unit. The exogenous glucose infusion rate may describe the rate at which glucose concentration of a corresponding monitored end-user increases following an exogenous glucose infusion event, such as at least one of meal ingestion, oral glucose consumption, continuous enteral nutrition, and constant glucose infusion. Exogenous glucose infusion rate may be calculated based at least in part on a model that relates a current exogenous glucose infusion rate to the following: (i) a time parameter describing the current time; (ii) a measure of glucose magnitude following initiation of an activity that leads to exogenous glucose infusion (e.g., consumption of a meal); (iii) plasma glucose distribution volume; and (iv) a glucose concentration peak interval, where (ii)-(iv) may be predefined values.

As further depicted in FIG. 9, the process 900 further includes adjusting $G_{in}$ (t) by the output value $f_2(G$ (t)) at step/operation 902. The $f_2(G)$ function is configured to return the insulin-independent glucose uptake that is caused by the glucose concentration G. Accordingly, the output value $f_2(G$ (t)) is the (actual or estimated) insulin-independent glucose uptake that is triggered by a current glucose concentration. In some embodiments, the $f_2(x)$ function is either: (i) bounded, of sigmoidal shape, and satisfies $G_2(0)=0$, & $G_2(G)$, $G'_2(G)>0$ for $G>0$; or (ii) of the form GG(G) where G>0 is a constant.

As further depicted in FIG. 9, the process 900 further includes adjusting the output of the step/operation 902 by the output value $f_{3,4}(G$ (t), $I(t-\tau_3))$ at step/operation 903. The $f_{3,4}(G,I)$ function is configured to return the insulin-dependent glucose uptake that is caused by both the glucose concentration G and the plasma insulin concentration I. Accordingly, the output value $f_{3,4}(G$ (t), $I(t-\tau_3))$ is the (actual or estimated) insulin-dependent glucose uptake that is caused by both a current glucose concentration and a delayed plasma insulin concentration that is returned by the function I(x). The $f_{3,4}(G,I)$ function may be a compound function generated by multiplying the functions $f_3(G)$ and $f_4(I)$. In some embodiments, $G_3(G)$ satisfies $G_3(0)=0$ and $0<G_3(G)\leq GG$, and $G'_3(G)>0$ for $G>0$, where G>0 is a constant. In some embodiments, $f_4(x)$ is either. (i) bounded, of sigmoidal shape, and satisfies $G_4(0)>0$, & $G_4(G)>0$ for $G>0$; or (ii) the identity function I(x). The delay factor $\tau_3$ may be configured to capture an expected delay between pancreatic insulin secretion and reception of secreted insulin by insulin receptors of insulin-dependent glucose-utilizing cells (e.g., fat/muscle cells).

As further depicted in FIG. 9, the process 900 includes adjusting the output of the step/operation 903 by the output of $f_5(I(t-\tau_2))$ at step/operation 904 to generate the change in glucose concentration at a current time t (i.e., G'(G)). The $f_5(I)$ function is configured to return the hepatic glucose production triggered by the plasma insulin concentration I. Accordingly, the output value $f_5(I(t-\tau_2))$ describes hepatic glucose production triggered by a delayed plasma insulin concentration that is returned by the function I(x). In some embodiments, $f_5(x)$ and $|G'(G)|$ are both bounded and $G_5(I)$ satisfies $G_5(0)>0$, $G_5(G)>0$, $G'_5(G)<0$ for $G>0$, and $G_5(G) \to G$ as $G \to \infty$, where $G \geq 0$ is a constant. The delay factor $\tau_2$ may be configured to capture an expected delay between reduced insulin levels and hepatic glucose production.

As depicted in FIG. 10, the process 1000 includes receiving the output value $I_{in}$ (t) at step/operation 1001. The $I_{in}(x)$ function is configured to return the exogenous insulin infusion rate at a time x. Accordingly, the output value $I_{in}$ (t) is the (actual or estimated) exogenous insulin infusion rate at a current time t. Examples of exogenous infusion rate include exogenous insulin infusion using a needle, exogenous insulin infusion using the automated insulin delivery computing entity 102, and/or the like.

As further depicted in FIG. 10, the process 1000 further includes adjusting the output value $I_{in}(t)$ by the output value $f_1(G(t-\tau_1))$ at step/operation 1002. The $f_1(G)$ function is configured to return the glucose-stimulated pancreatic insulin secretion rate that is caused by the glucose concentration G. Accordingly, the output value $f_1(G(t-\tau_1))$ is the (actual or estimated) glucose-stimulated pancreatic insulin secretion rate that is triggered by delayed glucose concentration measurement. In some embodiments, the $f_2(x)$ function is bounded, is of sigmoidal shape, and satisfies $G_1$ $(0) \geq 0$, $G_1$ (G), $G'_1$ (G)>0 for $G>0$. The delay factor $\tau_1$ may be configured to capture an expected delay between appearance of glucose in bloodstream and pancreatic insulin secretion in response to the noted appearance.

As further depicted in FIG. 10, the process 1000 further includes adjusting the output of the step/operation 1002 by the output of $r(I(t))$ at step/operation 1003 to generate the change in plasma insulin concentration at a current time t (i.e., G(G)). $r(I(t))$ is the insulin degradation rate caused by the current plasma insulin concentration measurement. In some embodiments, $r(I(t))$ either: (i) assumes Michael-Menten kinetics, i.e., $G(G(G)=(G(G)*G_1)/(G(G)+G_2)$ for some constants $G_1$, $G_2>0$; or (ii) satisfies $G*0=0$, $G*\infty=\infty$, and $[G(G(G))]'>0$.

The generalized hybrid glucose-insulin prediction model described by the Equations 1-2 as well as the FIGS. 9-10 can take many analytical forms. An example analytical form is generated by modifying the generalized hybrid glucose-insulin prediction model in accordance with the computational models that are depicted in Equations 3-8:

$$f_1(G(t-\tau)) = d\frac{G^n(t-\tau)}{\alpha^n + G^n(t-\tau)}$$ Equation 3

$$f_2(G(t)) = eG(t)$$ Equation 4

$$f_3(G(t)) = aG(t)$$ Equation 5

$$f_4(G(t)) = I(t)$$ Equation 6

$$f_5(I(t)) = b$$ Equation 7

$$G_{in}(t) = \frac{M}{V_G \cdot BW \cdot \theta^2} te^{-t/\theta}$$ Equation 8

Example functional designations for the various parameters of the computational models of the Equations 3-8 are described below as well as in the below Table 1.

TABLE 1

| Symbol | Description (units) |
| --- | --- |
| t | time (min) |
| G | plasma glucose concentration (mg/dl) |
| I | plasma insulin concentration (µU/ml) |
| $G_{in}$ | glucose appearance rate following a meal (mg/dl · min$^{-1}$) |
| a | insulin-dependent glucose uptake coefficient ((µU/ml · min)$^{-1}$) |
| b | hepatic glucose production rate (mg/dl · min$^{-1}$) |
| c | insulin degradation rate (min$^{-1}$) |
| d | maximum insulin secretion rate (µU/mlml · min$^{-1}$) |
| e | glucose effectiveness-insulin-independent glucose uptake rate (min$^{-1}$) |
| $\alpha_1$ | half-saturation plasma glucose concentration value (mg/dl) |
| n | Hill exponent-pancreatic response to accelerate insulin secretion (unitless) |
| τ | time delay of insulin secretion stimulated by plasma glucose (min) |
| M | measure of the magnitude of glucose following a meal (mg) |
| $V_G$ | plasma glucose distribution volume (dl) |
| θ | time between the first appearance of glucose in the bloodstream following a meal and peak of meal-absorption (mins) | a is the insulin-dependent glucose uptake coefficient parameter, which may describe a coefficient related to the rate at which cells of a corresponding monitored end-user utilize glucose in response to receiving insulin at their insulin receptors. Insulin-dependent glucose uptake includes glucose utilization by insulin receptors of muscle cells, fat cells, and other tissue cells, where the noted insulin receptors receive insulin and in response activate a signaling cascade for GLUT4 translocation, which in turn causes the cells to consume the glucose and convert it to energy. As modeled herein, insulin-dependent glucose uptake is the output of a function of both glucose concentrations and plasma insulin concentrations. The insulin-dependent glucose uptake coefficient parameter may take a value that is expressed as the inverse of atomic mass units per milliliters times inverse of a minute ((U/ml*min)$^{-1}$).

b is the hepatic glucose production rate parameter, which may describe the estimated rate at which liver cells of a corresponding monitored end-user produce and secrete insulin in response to production and insulin secretion of glucagon by α-cells in the liver of the corresponding monitored end-user, where the noted glucagon production and insulin secretion may exert control over metabolic pathways in the liver in a manner that leads to glucose production. The hepatic glucose production rate parameter may take a value that is described as milligrams per deciliter times inverse of a minute (mg/dl*min$^{-1}$).

c is the insulin degradation rate parameter, which may describe the estimated rate at which insulin is cleared by insulin-sensitive tissues of a corresponding monitored end-user. Insulin clearance activities may be performed by liver, kidney, muscle, adipose cells, and other tissues. The insulin degradation rate parameter may be a factor in an insulin degradation rate function that applies the insulin degradation rate parameter to the plasma insulin concentration. The insulin degradation parameter may take a value that is described as the number of insulin molecules that are degraded by insulin-sensitive tissues in each minute (min$^{-1}$).

d is the maximum insulin secretion rate parameter, which may describe the estimated maximal rate at which β-cells in pancreas of a corresponding monitored end-user can produce and secrete insulin in response to elevated glucose concentrations in the bloodstream of the corresponding monitored end-user. The maximal insulin secretion rate parameter may take a value that is expressed atomic mass units per milliliter times inverse of a minute (U/ml*min$^{-1}$).

e is the insulin-independent glucose uptake rate parameter, which may describe the estimated rate at which cells of a corresponding monitored end-user utilize glucose, where the noted glucose utilization is performed independent of insulin secretion and reception processes. Insulin-independent glucose utilization is performed by the brain cells and cells of the nervous system as well as through urination. As modeled herein, insulin-independent glucose utilization is a computational model of glucose plasma concentration. The insulin-independent glucose uptake rate parameter may take a value that is expressed as the number of glucose molecules that are utilized using insulin-independent glucose uptake in each minute (min$^{-1}$).

α is the half-saturation glucose concentration parameter, which may describe an estimated measure of glucose concentration at a point in time in which half of a maximal degree of possible glucose uptake has been performed for a corresponding monitored end-user. The half-saturation glucose concentration parameter can be utilized as a measure of glucose uptake capability of a monitored end-user. The half-saturation glucose concentration parameter can take a value that is expressed as milligrams per deciliter (mg/dl).

n is the half-saturation glucose concentration parameter, which may describe an estimated measure of the rate at which β-cells of pancreas of a corresponding monitored end-user accelerate insulin production and insulin secretion when the noted β-cells detect heightened levels of glucose concentration in the bloodstream of the corresponding monitored end-user. The insulin secretion acceleration parameter may take the form of an exponential parameter. In some embodiments, the hybrid glucose-insulin prediction machine learning model models insulin secretion by β-cells as a Hill function (e.g., the Hill function $$\frac{G \cdot G^G(G-G)}{G^G + G^G(G-G)}$$

which includes the insulin secretion acceleration parameter as the Hill coefficient. In some of the noted embodiments, the steady-state glucose-insulin prediction machine learning model inherits the Hill coefficient from the hybrid glucose-insulin prediction machine learning model, as the Hill coefficient survives both the derivation of the glucose-biased glucose-insulin prediction machine learning model from the hybrid glucose-insulin prediction machine learning model as well as the derivation of the steady-state glucose-insulin prediction machine learning model from the glucose-biased glucose-insulin prediction machine learning model.

G is the insulin secretion delay parameter, which may describe an estimated measure of temporal delay between appearance of heightened glucose concentrations in the bloodstream of a corresponding monitored end-user and a time associated with insulin secretion by β-cells of the pancreas. For example, the insulin secretion time delay parameter may describe the estimated measure of temporal delay between appearance of heightened glucose concentrations in the bloodstream of the corresponding monitored end-user and a time associated with initiation of insulin secretion by β-cells of the pancreas. As another example, the insulin secretion time delay parameter may describe the estimated measure of temporal delay between appearance of heightened glucose concentrations in the bloodstream of the corresponding monitored end-user and a time associated with termination of insulin secretion by β-cells of the pancreas.

θ is the glucose concentration peak interval parameter, which may describe an estimated length of a time between the first appearance of the glucose in the bloodstream of a corresponding monitored end-user as a result of a exogenous glucose infusion and peak of glucose in the blood stream of the corresponding monitored end-user as a result of the exogenous glucose infusion. For example, the glucose concentration peak interval parameter may describe a time delay between first appearance of exogenously-infused glucose in the bloodstream of the monitored end-user as a result of a meal ingestion and a peak of meal absorption. The glucose concentration peak interval parameter may take a value that is expressed as minutes (min).

$V_G$ is the glucose concentration and M is the magnitude of glucose following an exogenous glucose ingestion session. In some embodiments, both $V_G$ and M are predefined values, and thus are not determined through optimization.

To derive the glucose-biased glucose-insulin prediction machine learning model, the predictive data analysis computing entity 106 first combines the models of Equations 3-7 into the computational model of Equations 1-2 to obtain models described by the Equations 9-10:

$$G'(t) = b - eG(t) - aG(t)I(t) + G_{in}(t) \quad \text{Equation 9}$$

$$I'(t) = d \frac{G^n(t-\tau_1)}{\alpha_1^n + G^n(t-\tau_1)} - cI(t) \quad \text{Equation 10}$$

Afterward, the predictive data analysis computing entity 106 differentiates the computational model of Equation 9 with respect to t to get the computational model of Equation 11:

$$G''(t) = -eG'(t) - a[G'(t)I(t) + G(t)I'(t)] + G'_{in}(t) \quad \text{Equation 11}$$

Next, the predictive data analysis computing entity 106 modifies the computational model of Equation 11 by substituting the right-hand-side of the computational model of Equation 10 for the G'(G) in order to generate the computational model of Equation 12:

$$\begin{aligned}G''(t) &= -eG'(t) - a[G'(t)I(t) + G(t)I'(t)] \\ &= -eG'(t) - aG'(t)I(t) - aG(t)I'(t) + G'_{in}(t) \\ &= -eG'(t) - aG'(t)I(t) - aG(t)\left[d\frac{G^n(t-\tau_1)}{a_1^n + G^n(t-\tau_1)} - cI(t)\right] + G'_{in}(t) \\ &= -eG'(t) - adG(t)\frac{G^n(t-\tau_1)}{a_1^n + G^n(t-\tau_1)} - aI(t)[G'(t) - cG(t)] + G'_{in}(t).\end{aligned} \quad \text{Equation 12}$$

Then, the predictive data analysis computing entity 106 modifies the computational model of Equation 9 by rearranging the noted model to obtain the computational model of Equation 13:

$$aI(t) = \frac{b - eG(t) + G_{in}(t) - G'(t)}{G(t)} \quad \text{Equation 13}$$

Subsequently, the predictive data analysis computing entity 106 modifies the computational model of Equation 12 by setting G'(t)=H(t), which enables the predictive data analysis computing entity 106 to generate an equivalent model that only uses first-order differential equations, and thus is more conducive to efficient numerical operations. An example of such a numerically-simplified equivalent model is depicted in the computational model of Equation 14:

$$H'(t) = G'_{in}(t) - eH(t) - adG(t)\frac{G^n(t-\tau_1)}{a_1^n + G^n(t-\tau_1)} + (b - eG(t) + G_{in}(t) - H(t))\left(\frac{cG(t) - H(t)}{G(t)}\right) \quad \text{Equation 14}$$

The computational model of Equation 14 is an example of a glucose-biased glucose-insulin prediction machine learning model. In some embodiments, the glucose-biased glucose-insulin prediction machine learning model is a machine learning model that is configured to relate a group of glucose-concentration-related measurements for a corresponding monitored end-user to desired parameters that describe functional properties of the glucose-insulin endocrine metabolic regulatory system of the corresponding monitored end-user. For example, the glucose-biased glucose-insulin prediction machine learning model may describe a machine learning model that is configured to relate the following: (i) a current glucose concentration; (ii) a delayed glucose concentration; (iii) a derivative of glucose concentration function with respect to time calculated at the current time; (iv) a current exogeneous glucose infusion rate; (v) a derivative of exogeneous glucose infusion rate function with respect to time calculated at the current time; (vi) an insulin-independent glucose uptake coefficient parameter; (vii) a hepatic glucose production rate parameter; (viii) an insulin degradation rate parameter, (ix) a maximal insulin secretion rate parameter; (x) an insulin-independent glucose uptake rate parameter; (xi) a half-saturation glucose concentration parameter value; and (xii) an insulin secretion acceleration parameter value. The glucose-biased glucose-insulin prediction machine learning model may be generated by substituting insulin-related factors with glucose-related factors in a hybrid glucose-insulin prediction machine learning model.

To obtain the steady-state glucose-insulin prediction machine learning model, the predictive data analysis computing entity 106 can utilize the assumption that, at a steady-state time interval of the glucose surge excursion, all time derivative factors of the glucose-biased glucose-insulin prediction machine learning model are zero and there is an absence of external stimuli (which implies that, for example, $G_{in}(t)=0$). In some embodiments, the steady-state time interval may describe a time interval within a glucose surge excursion for a corresponding monitored end-user that is estimated to be associated with absence of temporal glucose changes and absence of exogenous glucose infusion. In some embodiments, during the steady-state time interval, all glucose-related derivatives with respect to time (e.g., derivative of glucose concentration with respect to time, derivative of exogenous glucose infusion with respect to time, derivative of hepatic glucose production with respect to time, and/or the like) are deemed to be near-zero values and the rate of exogenous glucose infusion is deemed to be zero.

In some embodiments, the steady-state time interval may be determined based at least in part on a predefined physiological computational model of the glucose-insulin endocrine metabolic regulatory system and/or may be determined based at least in part on monitoring glucose-related measurements of the corresponding monitored end-user in the past. For example, the steady-state time interval may include at least a portion of a terminal part of a glucose surge excursion, such as a tail end of a glucose surge excursion. In some embodiments, the steady-state time interval includes all of the points in time that satisfy one or more steady-state time interval criteria (e.g., all of the points in time within a detected tail end of a glucose surge excursion). In some embodiments, the steady-state time interval includes only a selected number of points in time that are selected (e.g., randomly or in accordance with one or more selection criteria) from the points in time that satisfy one or more steady-state time interval criteria (e.g., a randomly-selected individual point in time from a detected tail end of a glucose surge excursion).

Accordingly, in some embodiments, by modifying the model of Equation 14 in accordance with the noted steady-state assumption, the predictive data analysis computing entity 106 can generate the model of Equation 15, which in turn can be rearranged to generate the models of Equation 16:

$$0 = -ad\frac{G_*^{n+1}}{\alpha_1^n + G_*^n} + c(b - eG_*) \quad \text{Equation 15}$$

$$b = ad\frac{G_*^{n+1}}{c(\alpha_1^n + G_*^n)} + eG_* \quad \text{Equation 16}$$

The models of Equations 15-16 are examples of steady-state glucose-insulin prediction machine learning models. In the depicted models of Equations 15-16, a, b, c, d, e, n, and α are the cross-steady-state parameters. A cross-steady-state parameter may be a data object that describes a functional property of the glucose-insulin endocrine metabolic regulatory system of a corresponding monitored end-user that is deemed to be true across the entirety of a glucose surge excursion (and/or across multiple glucose surge excursions), including any portion of the glucose surge excursion that occurs before a corresponding steady-state time interval and any portion of the glucose surge excursion that occurs after the corresponding steady-state time interval. Examples of cross-steady-state parameters include an insulin-dependent glucose uptake coefficient parameter, a hepatic glucose production rate parameter, an insulin degradation rate parameter, a maximal insulin secretion rate parameter, an insulin-independent glucose uptake rate parameter, a half-saturation glucose concentration parameter, and/or an insulin secretion acceleration parameter. In some embodiments, a cross-steady-state parameter describes a functional property of the glucose-insulin endocrine metabolic regulatory system of a corresponding monitored end-user whose value is not a function of the glucose concentration and the plasma insulin concentration.

In the depicted models of Equations 15-16, $G_*$ is the steady-state glucose concentration measurement, which may describe a glucose concentration measurement that is associated with the steady-state time interval introduced above. In some embodiments, the steady-state glucose concentration measurement describes a measure of statistical distribution of a group of glucose concentration measurements that are deemed to be associated with the steady-state time interval, such as a mean of the group of glucose concentration measurements that are deemed to be associated with the steady-state time interval, a weighted mean of the group of glucose concentration measurements that are deemed to be associated with the steady-state time interval, a median of the group of glucose concentration measurements that are deemed to be associated with the steady-state time interval, a mode of the group of glucose concentration measurements that are deemed to be associated with the steady-state time interval, a maximal value of the group of glucose concentration measurements that are deemed to be associated with the steady-state time interval, a minimum value of the group of glucose concentration measurements that are deemed to be associated with the steady-state time interval, and/or the like. In some embodiments, the steady-state time interval is a singular point in time, and the steady-state glucose concentration measurement describes a glucose concentration measurement associated with the singular point in time.

One important objective behind deriving the steady-state glucose-insulin prediction machine learning prediction models is that the steady-state glucose-insulin prediction machine learning models have fewer parameters than both the hybrid glucose-insulin machine learning prediction models and glucose-biased glucose-insulin machine learning prediction models. The same is true of the relationship between the glucose-biased glucose-insulin machine learning prediction models and the hybrid glucose-insulin machine learning prediction models, where the glucose-biased glucose-insulin machine learning prediction models have fewer parameters than the hybrid glucose-insulin machine learning prediction models. This in turn means that steady-state glucose-insulin machine learning prediction models are likely to have greater storage efficiency, operational efficiency, and per-parameter optimization accuracy relative to both glucose-biased glucose-insulin machine learning prediction models and the hybrid glucose-insulin machine learning prediction models. This further means that glucose-biased glucose-insulin machine learning prediction models are likely to have greater storage efficiency, operational efficiency, and per-parameter optimization accuracy relative to hybrid glucose-insulin machine learning prediction models.

Moreover, by removing the need for receiving insulin sensor data from insulin sensors in order to perform predictive monitoring of the glucose-insulin endocrine metabolic regulatory system of a corresponding monitored end-user, steady-state glucose-insulin machine learning prediction models and glucose-biased glucose-insulin machine learning prediction models have greater network transmission efficiency and network reliability, as they reduce the need for network transmissions between predictive data analysis computing entities and insulin sensory devices and reduce the risk that network failures associated with network transmissions between predictive data analysis computing entities and insulin sensory devices undermine security and reliability of distributed glucose-insulin monitoring systems.

C. Parameter Optimization Techniques

At step/operation 703, the predictive data analysis computing entity 106 processes a steady-state glucose concentration measurement using the steady-state glucose-insulin prediction machine learning model to generate one or more target parameter values for the steady-state glucose-insulin prediction machine learning model. To do so, the predictive data analysis computing entity 106 may first determine the steady-state glucose concentration measurement based at least in part on the glucose monitoring data. In some embodiments, the steady-state glucose concentration measurement is associated with a steady-state time interval within the glucose surge excursion, and the steady-state time interval is estimated to be associated with absence of temporal glucose changes and with absence of exogenous glucose infusion. Afterward, the predictive data analysis computing entity 106 may determine a combination of optimum values for the cross-steady-state parameters of the steady-state glucose concentration measurement in a manner that, when supplied to the steady-state glucose concentration measurement, generates an inferred steady-state glucose concentration measurement that has the least amount of deviation from the determined steady-state glucose concentration measurement relative to other inferred steady-state glucose concentration measurements generated by non-optimum combination of values for the cross-steady-state parameters of the steady-state glucose concentration measurement. Thereafter, the predictive data analysis computing entity 106 generates the target parameter values based at least in part on the combination of optimum cross-steady-state parameter values.

In some embodiments, a target parameter describes a cross-steady-state parameter that is in a subset of the cross-steady-state parameters of a corresponding steady-state glucose-insulin prediction machine learning model that is deemed related to generating a corresponding glucose-insulin prediction. For example, if the corresponding glucose-insulin prediction describes a measure of sensitivity of the liver cells and the muscle/fat cells of the corresponding monitored end-user to performing glucose uptake in response to secretion of insulin by β-cells in pancreas, the target parameters may include the maximal insulin secretion rate parameter, the insulin-independent glucose uptake coefficient parameter, and the insulin secretion acceleration parameter. As another example, if the corresponding glucose-insulin prediction describes a measure of insulin effectiveness rate, the target parameters may include the maximal insulin secretion rate parameter and the insulin secretion acceleration parameter.

In some embodiments, with respect to the steady-state glucose-insulin machine learning model of Equation 16, the target parameters may include d and n, as the noted cross-steady-state parameters and/or a combination of them can provide insights about insulin secretion, which in turn provides therapeutic insights about the insulin secretion capacity of pancreatic β-cells as well as the insulin sensitivity of insulin-dependent glucose-utilizing cells such as liver and fat/muscle cells and/or the beta cell capacity of beta cells of pancreas to synthetize and secrete insulin.

Step/operation 703 may be performed in accordance with any parameter optimization method, including local optimizations methods such as gradient descent as well as global optimization methods that utilize complete traversals of the parameter space. FIG. 11 provides a flowchart diagram of an example process 1100 for performing parameter optimization that can be used to generate optimum values for cross-steady-state parameters of a steady-state glucose-insulin prediction machine learning model.

The process 1100 and the related quasi-global optimization methods discussed herein provide a powerful tool for performing optimization in a manner that avoids reliability pitfalls of various efficient local optimization methods as well as the efficiency pitfalls of various reliable global optimization methods. While various embodiments of the present invention discuss the process 1100 and the related quasi-global optimization methods discussed herein in the context of performing cross-steady-state parameter optimization in relation to a steady-state glucose-insulin prediction machine learning model, a person of ordinary skill in the relevant technology will recognize that the process 1100 and the related quasi-global optimization methods discussed herein have applications far beyond performing cross-steady-state parameter optimization in relation to a steady-state glucose-insulin prediction machine learning model, as the noted concepts can be used to efficiently and reliably performing any optimization tasks. For example, the process 1100 and the related quasi-global optimization methods discussed herein can be utilized to optimize utility functions (e.g., maximize reward functions, minimize loss functions, and/or the like) in the context of training various machine learning models (e.g., neural network machine learning models) that are conducive to optimization-based training techniques.

The process 1100 begins at step/operation 1101 when the predictive data analysis computing entity 106 identifies a model utility data object for a non-optimized machine learning model (e.g., a non-optimized steady-state glucose-insulin prediction machine learning model). The model utility data object may be a data object that describes: (i) one or more parameter value combinations, where each parameter value combination includes a candidate value for each optimizable parameter of one or more optimizable parameters of a corresponding machine learning model (e.g., for each cross-steady-state parameter of a steady-state glucose-insulin prediction machine learning model); and (ii) for each parameter value combination, a utility measurement.

For example, the model utility data object may describe a loss function of a machine learning model, as the loss function maps each parameter value combination associated with the machine learning model to a loss value (an example of a utility measurement). As another example, the model utility data object for a steady-state glucose-insulin prediction machine learning model may describe, for each parameter value combination that includes a candidate value for each cross-steady-state parameter of the steady-state glucose-insulin prediction machine learning model, a measure of deviation of an inferred steady-state glucose concentration measurement determined by processing the parameter value combination using the steady-state glucose-insulin prediction machine learning model from a ground-truth steady-state glucose concentration measurement determined based at least in part on glucose monitoring data.

An operational example of a model utility data object 1201 is depicted in FIG. 12. As depicted in FIG. 9, the model utility data object 1201 is associated with a machine learning model that is in turn (for ease of illustration) associated with only one optimizable parameter 1211. The model utility data object 1201 includes a graph element 1221 that includes, at each of its points, a utility measure (whose range is described by the vertical coordinate of the model utility data object 1201) for the candidate value of the optimizable parameter 1211 (where the range of the optimizable parameter 1211 is described by the horizontal coordinate of the model utility data object 1201).

At step/operation 1102, the predictive data analysis computing entity 106 processes the model utility data object using a parameter space refinement machine learning model in order to generate an optimum parameter space for the non-optimized machine learning model. In some embodiments, step/operation 1102 performs machine learning analysis to reduce/refine the parameter space of the model utility data object, which in turn reduces the space within which future optimization operations (e.g., future global optimization operations) are performed, and thus in turn reduces the computational complexity of optimization-based predictive data analysis operations (e.g., optimization-based training operations).

The parameter space refinement machine learning model may be a machine learning model that is configured to process model utility data objects to identify optimum parameter spaces for the machine learning models that are associated with the noted model utility data objects. For example, the parameter space refinement machine learning model may be a convolutional neural network model that is configured to process an image representation of the model utility data object to determine an optimum image region of the image representation, where the optimum parameter space may be determined based at least in part on the optimum image region.

As another example, the parameter space refinement machine learning model may be a recurrent neural network model configured to process the one or more utility measurements in a sequential manner to generate a final hidden state for an ultimate timestep of the recurrent neural network, where the final hidden state is used to generate an encoded representation of the optimum parameter space. In some of the noted embodiments, the optimum parameter space is determined based at least in part on the encoded representation of the optimum parameter space.

As a further example, the parameter space refinement machine learning model may be an encoder model (e.g., an autoencoder model, a variational autoencoder model, and/or the like) that is configured to process the model utility data object to generate an encoded representation of the optimum parameter space, where the optimum parameter space is determined based at least in part on the encoded representation of the optimum parameter space.

As yet another example, the parameter space refinement machine learning model may be an attention-based machine learning model that is configured to process the model utility data object to generate an attention vector over the parameter space of the machine learning model, where the optimum parameter space is determined based at least in part on the noted attention vector over the parameter space of the machine learning model.

The optimum parameter space may be a subset of the parameter space of a machine learning model, where the subset of the parameter space describes, for each optimizable parameter associated with the machine learning model, a subrange of the total range of the optimizable parameter, and where the subset of the parameter space is estimated to include an optimum combination of values for the optimizable parameters associated with the machine learning model (e.g., an optimum parameter value combination that generates a locally optimum utility measurement, an optimum parameter value combination that generates a globally optimum utility measurement, and/or the like).

For example, if a machine learning model is associated with a first optimizable parameter that is in turn associated with a total range [0, 1] and a second optimizable parameter that is in turn associated with the total range [10, 20], an example optimum parameter space for the machine learning model may describe parameter value combinations whose first parameter value falls between [0.2, 0.3] and whose second parameter value is [10.2, 10.3]. In the noted example, the described optimum parameter space includes the parameter value combination whose first parameter value is 0.25 and whose second parameter value combination is 10.2, but it does not include the parameter value combination whose first parameter value is 3.1 and whose second parameter value combination is 10.2.

In the context of optimizing the cross-steady-state parameters of a steady-state glucose-insulin prediction machine learning model, the optimum parameter space may describe a subrange of the total range of each of the cross-steady-state parameters. For example, the optimum parameter space may include a subrange for a, a subrange for b, a subrange for c, a subrange for d, a subrange for e, a subrange for n, and a subrange for a.

An operational example of an optimum parameter space 1231 is presented in FIG. 12. As depicted in FIG. 12, the optimum parameter space 1231 describes a subrange of the sole optimizable parameter of the model utility data object 1201, which is the optimizable parameter 1211. As discussed above, the optimum parameter space 1231 may be generated by processing the model utility data object 1201 using a parameter space refinement machine learning model. For example, in some embodiments, the predictive data analysis computing entity 106 may process an image representation of the model utility data object 1201 using a convolutional neural network model that is configured to identify an image region of the noted image representation of the model utility data object 1201.

Returning to FIG. 11, at step/operation 1103, the predictive data analysis computing entity 106 determines an estimated optimum utility measurement from each intra-region optimum utility measurement. The estimated optimum utility measurement may describe a utility measurement that is deemed the optimum utility measurement among all of the utility measurements that are associated with parameter value combinations that fall within a corresponding optimum parameter space. Accordingly, an estimated optimum utility measurement should both be associated with a parameter value combination that falls within the corresponding optimum parameter space and be an estimated/exact optimum utility measurement (e.g., a locally minimum loss value, a globally minimum loss value, a locally maximum utility value, a globally maximum utility value, and/or the like) among all of the utility measurements that are associated with parameter value combinations which fall within the optimum parameter space. The set of all utility measurements that are associated with parameter value combinations which fall within the optimum parameter space is referred to herein as an intra-region utility measurement subset, and an individual element of an intra-region utility measurement subset is referred to herein as an intra-region optimum utility measurement. Therefore, the estimated optimum utility measurement may be an intra-region utility measurement that is deemed an estimated/exact optimum value in the intra-region utility measurement subset.

In the context of optimizing the cross-steady-state parameters of a steady-state glucose-insulin machine learning model, each utility measurement for a parameter value combination may correspond to a measure of deviation between an inferred steady-state glucose concentration measurement determined using the parameter value combination and a ground-truth glucose concentration measurement determined based at least in part on the glucose monitoring data. Thus, in some embodiments, optimizing this utility measure includes minimizing this utility measure, e.g., finding a parameter value combination that falls within the optimum parameter space and that generates a utility measurement that is lower than the utility measurement for other parameter value combinations that also fall within the optimum parameter space.

In some embodiments, the intra-region optimum utility measurement is an intra-region global optimum utility measurement for the intra-region utility measurement subset that is determined by applying a global optimization routine to the optimum parameter space (as opposed to the totality of the model utility data object). For example, in some embodiments, the intra-region global optimum utility measurement is determined using a holistic traversal of the intra-region utility measurement subset. In some embodiments, when step/operation 803 includes performing global optimization on the optimum parameter space, the disclosed optimization technique is referred to herein as a quasi-global optimization technique.

In some embodiments, the intra-region optimum utility measurement is an intra-region local optimum utility measurement for the intra-region utility measurement subset that is determined by applying a local optimization routine to the optimum parameter space (as opposed to the totality of the model utility data object). For example, in some embodiments, the intra-region global optimum utility measurement is determined using a gradient-descent-based traversal of the intra-region utility measurement subset. In some embodiments, when step/operation 803 includes performing local optimization on the optimum parameter space, the disclosed optimization technique is referred to herein an expediated local optimization technique.

An operational example of an intra-region utility measurement subset 1241 and an estimated optimum utility measurement 1251 is depicted in FIG. 12. As depicted in FIG. 12, the intra-region utility measurement 1241 includes a collection of the utility measurements (in the case of a model utility data object that describes a continuous utility function, an interval of the utility measurements) that corresponds to parameter value combinations that fall within the optimum parameter space 1231. As further depicted in FIG. 12, the estimated optimum utility measurement 1251 is the minimum point of the intra-region utility measurement subset 1241.

Returning to FIG. 11, at step/operation 1104, the predictive data analysis computing entity 106 updates the non-optimized learning model in accordance with a parameter value combination of the one or more parameter value combinations that is associated with the estimated global optimum utility measurement to generate an optimized machine learning model. In some embodiments, to generate the optimized machine learning model, the predictive data analysis computing entity 106 adopts the parameter value combination (e.g., the parameter value combination 1261 in FIG. 12) that is associated with the estimated global optimum utility measurement as the optimum parameter value for the non-optimized machine learning model.

In the context of optimizing the cross-steady-state parameters of a steady-state glucose-insulin machine learning model, the predictive data analysis computing entity 106 may identify a combination of values for the steady-state parameters that correspond to the estimated global optimum utility measurement as the combination of steady-state parameters that best predict the ground-truth steady-state glucose concentration measurement. The predictive data analysis computing entity 106 then selects target parameter values from the optimized steady-state parameter values.

D. Predictive Glucose-Insulin Management

Returning to FIG. 7, at step/operation 704, the predictive data analysis computing entity 106 generates one or more glucose-insulin predictions based at least in part on the target parameter values. A glucose-insulin prediction may describe a conclusion about one or more functional properties of the glucose-insulin endocrine metabolic regulatory system of a corresponding monitored end-user. For example, the predictive data analysis computing entity 106 may determine an insulin sensitivity prediction based at least in part on at least one of the maximal insulin secretion rate parameter value and the insulin secretion acceleration parameter value. In some embodiments, if the maximal insulin secretion rate parameter is higher than an expected amount, a computer system may determine that the insulin-dependent glucose-utilizing cells of the monitored end-user have developed abnormal levels of insulin sensitivity, which in turn may be used to facilitate an automated diagnosis of type-2 diabetes. As another example, the predictive data analysis computing entity 106 may detect a potential liver problem based at least in part on an abnormally hepatic glucose production parameter. As yet another example, the predictive data analysis computing entity 106 may detect a potential nervous system problem if the insulin-independent glucose uptake rate parameter is abnormally low.

An example of a glucose-insulin prediction is a beta cell capacity prediction about the capacity of β-cells in pancreas to synthetize and secrete insulin. In some embodiments, a beta cell capacity prediction may be determined based on the optimized values for at least one of the noted parameters of the steady-state glucose-insulin prediction machine learning model of Equation 15 and/or the steady-state glucose-insulin prediction machine learning model of Equation 16: a, d, or n. In some embodiments, a beta cell capacity prediction may be determined based on an estimated delay factor determined using a glucose-insulin prediction model described in Subsection B of the present section. In some embodiments, a beta cell capacity measurement may be used to determine an optimal exogenous insulin injection rate for a monitored individual.

At step/operation 705, the predictive data analysis computing entity 106 performs one or more prediction-based actions based at least in part on the glucose-insulin predictions. For example, the predictive data analysis computing entity 106 may be configured to generate one or more physician alerts and/or one or more healthcare provider alerts based at least in part on the glucose-insulin predictions. As another example, the predictive data analysis computing entity 106 may be configured to generate one or more automated physician appointments, automated medical notes, automated prescription recommendations, and/or the like based at least in part on the glucose-insulin predictions. As yet another example, the predictive data analysis computing entity 106 may be configured to enable an end-user device to display a user interface, where the user interface has been generated based at least in part on the glucose-insulin predictions.

In some embodiments, generating the one or more glucose-insulin predictions comprises generating an insulin sensitivity prediction based at least in part on at least one of the maximal insulin secretion rate parameter value and the insulin secretion acceleration parameter value; and determining, based at least in part on the insulin sensitivity measure, an exogenous insulin need determination. In some of the noted embodiments, performing the one or more prediction-based actions comprises, in response to determining a positive exogenous insulin need determination, generating one or more automated medical alarms. In some of the noted embodiments, performing the one or more prediction-based actions comprises, in response to determining a positive exogenous insulin need determination, the predictive data analysis computing entity 106 causes the automated insulin delivery computing entity 102 to perform an automated exogenous insulin injection into the bloodstream of the corresponding monitored end-user. In some of the noted embodiments, performing the one or more prediction-based actions comprises, in response to determining a positive exogenous insulin need determination, causing an automated medical response such as arrangement of ambulance services for the corresponding monitored end-user.

VI. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
   receiving, by one or more processors and from a continuous glucose monitoring (CGM) device, CGM data for an end-user;
   determining, by the one or more processors, an excursion start time of the CGM data based at least in part on a plurality of excursion initiation probabilities for a plurality of temporal units associated with the CGM data;
   determining, by the one or more processors, an excursion end time based at least in part on a plurality of excursion termination probabilities for a subset of the plurality of temporal units that occur after a predefined time interval following the excursion start time, wherein each excursion termination probability of the plurality of excursion termination probabilities is adjusted by an adjustment factor configured to:
     (a) reward a latency of a corresponding temporal unit in an ordering of the subset of the plurality of temporal units, and
     (b) penalize a precedence of the corresponding temporal unit in the ordering of the subset of the plurality of temporal units;
   identifying, by the one or more processors, a time interval within the CGM data that corresponds to a glucose surge excursion based at least in part on the excursion start time and the excursion end time, wherein the time interval excludes the excursion start time and the excursion end time;
   determining, by the one or more processors and based at least in part on a machine learning model that is trained using ground-truth data corresponding to the glucose surge excursion, one or more glucose-insulin predictions based at least in part on the glucose surge excursion; and
   based at least in part on the one or more glucose-insulin predictions, performing an automated exogenous insulin injection into the end-user with an automated insulin delivery computing entity.

2. The computer-implemented method of claim 1, wherein:
   one or more of the plurality of excursion initiation probabilities are determined based at least in part on one or more of (i) a first comparison between a neighboring CGM moving average and a neighboring CGM moving average threshold, (ii) a first comparison between a CGM first derivative approximation and a CGM first derivative approximation threshold, or (iii) a first comparison between a CGM z-score and a CGM z-score threshold;
   one or more of the plurality of excursion termination probabilities are determined based at least in part on one or more of (i) a second comparison between the neighboring CGM moving average and the neighboring CGM moving average threshold, (ii) a second comparison between the CGM first derivative approximation and the CGM first derivative approximation threshold, or (iii) a second comparison between the CGM z-score and the CGM z-score threshold; and
   the neighboring CGM moving average threshold is determined based at least in part on a CGM measurement for a temporal unit of the plurality of temporal units and one or more CGM measurements for one or more temporal units of the plurality of temporal units preceding the temporal unit.

3. The computer-implemented method of claim 1, wherein one or more of the plurality of excursion initiation probabilities are determined based at least in part on one or more user-supplied meal session initiation indicators.

4. The computer-implemented method of claim 1, wherein one or more of the plurality of excursion termination probabilities are determined based at least in part on one or more user-supplied meal session termination indicators.

5. The computer-implemented method of claim 1, wherein:
   the plurality of excursion initiation probabilities is determined by providing CGM measurements to the machine learning model,
   the machine learning model is configured to process the CGM measurements to generate the plurality of excursion initiation probabilities, and
   the machine learning model is trained using the ground-truth data, wherein the ground-truth data is determined based at least in part on one or more user-supplied meal session initiation indicators.

6. The computer-implemented method of claim 1, wherein:
the plurality of excursion termination probabilities is determined by providing CGM measurements associated with the subset of the plurality of temporal units to the machine learning model,
the machine learning model is configured to process the CGM measurements to generate the plurality of excursion termination probabilities, and
the machine learning model is trained using the ground-truth data, wherein the ground-truth data is determined based at least in part on one or more user-supplied meal session termination indicators.

7. The computer-implemented method of claim 1, wherein the one or more glucose-insulin predictions comprise an insulin sensitivity prediction.

8. The computer-implemented method of claim 2, wherein the neighboring CGM moving average threshold is 2.5 milligrams per deciliter per minute, the CGM first derivative approximation threshold is 2.5 milligrams per deciliter per minute, the CGM z-score threshold is 1.0, or any combination thereof.

9. The computer-implemented method of claim 1, wherein the machine learning model comprises a steady-state glucose-insulin prediction machine learning model, a glucose-biased glucose-insulin predication machine learning model, a hybrid glucose-insulin predication machine learning model, an excursion termination detection machine learning model, a parameter space refinement machine learning model, or any combination thereof.

10. The computer-implemented method of claim 1, wherein the machine learning model is configured using one or more quasi-global parameter optimization operations.

11. The computer-implemented method of claim 1, wherein determining the excursion end time comprises:
determining one or more potential excursion end times based at least in part on the plurality of excursion initiation probabilities;
determining an excursion probability for a potential excursion end time of the one or more potential excursion end times, wherein the excursion probability is based at least in part on a temporal deviation between the excursion start time and the potential excursion end time; and
determining the excursion end time based at least in part on the excursion probability.

12. A system comprising one or more memories, one or more processors communicatively coupled to the one or more memories, and an automated insulin delivery computing entity, the one or more processors configured to:
receive, from a continuous glucose monitoring (CGM) device, CGM data for an end-user;
determine an excursion start time of the CGM data based at least in part on a plurality of excursion initiation probabilities for a plurality of temporal units associated with the CGM data;
determine an excursion end time based at least in part on a plurality of excursion termination probabilities for a subset of the plurality of temporal units that occur after a predefined time interval following the excursion start time, wherein each excursion termination probability of the plurality of excursion termination probabilities is adjusted by an adjustment factor configured to:
(a) reward a latency of a corresponding temporal unit in an ordering of the subset of the plurality of temporal units, and
(b) penalize a precedence of the corresponding temporal unit in the ordering of the subset of the plurality of temporal units;
identify a time interval within the CGM data that corresponds to a glucose surge excursion based at least in part on the excursion start time and the excursion end time, wherein the time interval excludes the excursion start time and the excursion end time;
determine, based at least in part on a machine learning model that is trained using ground-truth data corresponding to the glucose surge excursion, one or more glucose-insulin predictions based at least in part on the glucose surge excursion; and
based at least in part on the one or more glucose-insulin predictions, perform an automated exogenous insulin injection into the end-user with the automated insulin delivery computing entity.

13. The system of claim 12, wherein one or more of the plurality of excursion initiation probabilities are determined based at least in part on one or more user-supplied meal session initiation indicators.

14. The system of claim 12, wherein one or more of the plurality of excursion termination probabilities are determined based at least in part on one or more user-supplied meal session termination indicators.

15. The system of claim 12, wherein:
the plurality of excursion initiation probabilities is determined by providing CGM measurements to the machine learning model,
the machine learning model is configured to process the CGM measurements to generate the plurality of excursion initiation probabilities, and
the machine learning model is trained using the ground-truth data, wherein the ground-truth data is determined based at least in part on one or more user-supplied meal session initiation indicators.

* * * * *

UNITED STATES PATENT AND TRADEMARK OFFICE
CERTIFICATE OF CORRECTION

| | | |
|---|---|---|
| PATENT NO. | : 12,207,950 B2 | Page 1 of 1 |
| APPLICATION NO. | : 16/985745 | |
| DATED | : January 28, 2025 | |
| INVENTOR(S) | : Steven Catani et al. | |

It is certified that error appears in the above-identified patent and that said Letters Patent is hereby corrected as shown below:

In the Claims

In Column 65, Line 26, Claim 9, delete "predication" and insert -- prediction --, therefor.

In Column 65, Line 27, Claim 9, delete "predication" and insert -- prediction --, therefor.

Signed and Sealed this
Fifteenth Day of April, 2025

Coke Morgan Stewart
*Acting Director of the United States Patent and Trademark Office*